(12) United States Patent
Moshos et al.

(10) Patent No.: US 10,059,680 B2
(45) Date of Patent: Aug. 28, 2018

(54) THIADIAZOLYL-OXIMINOACETIC ACID DERIVATIVE COMPOUNDS

(71) Applicant: Merck Sharp & Dohme Corp., Rahway, NJ (US)

(72) Inventors: Kristos Adrian Moshos, Belmont, MA (US); Valdas Jurkauskas, Cambridge, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/536,545

(22) PCT Filed: Dec. 18, 2015

(86) PCT No.: PCT/US2015/066839
§ 371 (c)(1),
(2) Date: Jun. 15, 2017

(87) PCT Pub. No.: WO2016/100897
PCT Pub. Date: Jun. 23, 2016

(65) Prior Publication Data
US 2017/0369459 A1 Dec. 28, 2017

Related U.S. Application Data

(60) Provisional application No. 62/093,775, filed on Dec. 18, 2014, provisional application No. 62/097,861, filed on Dec. 30, 2014.

(51) Int. Cl.
*C07D 285/08* (2006.01)
*A61K 31/4196* (2006.01)

(52) U.S. Cl.
CPC ........ *C07D 285/08* (2013.01); *A61K 31/4196* (2013.01)

(58) Field of Classification Search
CPC .................................................. C07D 285/08
See application file for complete search history.

(56) References Cited

U.S. PATENT DOCUMENTS

| | | | |
|---|---|---|---|
| 7,129,232 B2 | 10/2006 | Ohki et al. | |
| 2005/0096306 A1 | 5/2005 | Yamanaka et al. | |
| 2007/0037786 A1 | 2/2007 | Ohki et al. | |
| 2012/0264727 A1* | 10/2012 | Cho | C07D 501/60 514/203 |
| 2016/0176897 A1 | 6/2016 | Moshos et al. | |
| 2017/0129906 A1 | 5/2017 | Moshos et al. | |

FOREIGN PATENT DOCUMENTS

| | | |
|---|---|---|
| EP | 0064582 | 12/1985 |
| JP | 1135778 | 5/1989 |
| WO | WO2016025813 | 2/2016 |
| WO | WO2016025839 | 2/2016 |
| WO | WO2016095860 | 6/2016 |
| WO | WO2016100897 | 6/2016 |
| WO | WO2016109259 | 7/2016 |

OTHER PUBLICATIONS

Ayoko Toda, et al, Synthesis and SAR of novel parenteral anti-pseudonmonal cephalosporins: Discovery of FR 264205, Bioorganic and Medicinal Chemistry Letters, 2008, pp. 4849-4852, vol. 18, WO.
PCT International Search Report and Written Opinion for PCT/US2015/066839 dated Feb. 26,2016; 8 pages.

* cited by examiner

*Primary Examiner* — Valerie Rodriguez-Garcia
(74) *Attorney, Agent, or Firm* — J. Eric Thies; John C. Todaro

(57) ABSTRACT

Thiadiazolyl-oximinoacetic acid derivatives have been synthesized, which are useful in the manufacture of cephalosporin antibiotic compounds. Compound (1) (TATD) is commercially available (CAS No. 76028-96-1). It has now been discovered that the thiadiazolyl-oximinoacetic acid derivative compound (1) (TATD) can be prepared from dimethyl malonate (SM 1, CAS No. 108-59-8) according to methods described herein. The methods provide products having desirable purity.

14 Claims, 14 Drawing Sheets

*Biorg. Med. Chem. Lett.* 18 (2008) 4849-4852

FIGURE 5

==== HPLC Analysis Report ====

Test Item            : C%, C(%,w/w), Identification
Notebook ID          : IAR-PT-C11030405-C14502B(IV)-10
Vail #               : 15
Injection Volume     : 10 uL
Method File Name     : C11030405-003.02-Method 2-LC811.lcm
Data Acquired        : 2/13/2014 09:20:55

System Configuration
<<Instrument>>
Instrument Name      : LC811
<<Column>>
Column Name          : Waters Xbridge Shield RP18
Column ID            : SLC145
Length               : 150 mm
Internal Diameter    : 3.0

<Chromatogram>

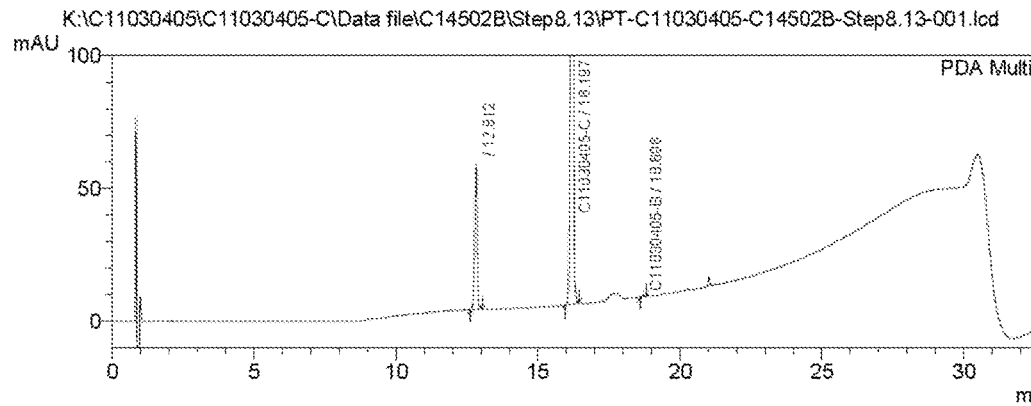

<Results>

Peak Table
Ch1 220nm 4nm

| Peak # | Name | Ret. Time | Area | Height | Area % | Resolution | Tailing Factor (10%) |
|---|---|---|---|---|---|---|---|
| 1 |  | 12.812 | 319388 | 54167 | 5.354 | 0.000 | 0.889 |
| 2 | C11030405-C | 16.197 | 5643192 | 1350949 | 94.599 | 25.163 | 1.099 |
| 3 | C11030405-B | 18.696 | 2790 | 679 | 0.047 | 23.370 | 1.031 |
| Total |  |  | 5965370 | 1405794 | 100.000 |  |  |

FIGURE 6

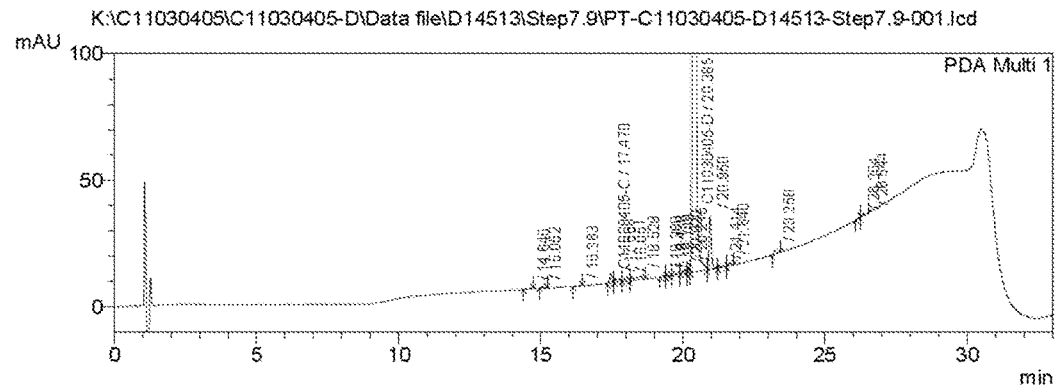

==== HPLC Analysis Report ====

Test Item : Purity,Assay
Notebook ID : IAR-PT-C11030405-D14513-35
Vail # : 15
Injection Volume : 10 uL
Method File Name : C11030405-004.02-Method 2-LC801.lcm
Data Acquired : 2/18/2014 04:24:37

System Configuration
<<Instrument>>
Instrument Name : LC801
<<Column>>
Column Name : Waters Xbridge Shield RP18
Column ID : SLC156
Length : 150 mm
Internal Diameter : 3.0

<Chromatogram>

<Results>

Peak Table
Ch1 220nm 4nm

| Peak # | Name | Ret. Time | Area | Height | Area % | Resolution | Tailing Factor (10%) |
|---|---|---|---|---|---|---|---|
| 1 | | 14.646 | 1791 | 209 | 0.036 | 0.000 | 0.779 |
| 2 | | 15.052 | 3339 | 612 | 0.067 | 2.378 | 1.342 |
| 3 | | 16.363 | 2039 | 179 | 0.041 | 6.926 | 0.859 |
| 4 | C11030405-C | 17.470 | 20530 | 3703 | 0.413 | 5.899 | 1.297 |
| 5 | | 17.660 | 12897 | 1416 | 0.259 | 0.880 | 0.000 |
| 6 | | 18.051 | 10900 | 1005 | 0.219 | 1.330 | 0.000 |
| 7 | | 18.529 | 26500 | 1506 | 0.533 | 1.042 | 0.000 |
| 8 | | 19.308 | 3572 | 627 | 0.072 | 2.019 | 0.000 |
| 9 | | 19.478 | 2644 | 477 | 0.053 | 1.118 | 0.000 |
| 10 | | 19.749 | 4459 | 574 | 0.090 | 1.578 | 1.466 |
| 11 | | 20.020 | 10124 | 1573 | 0.203 | 1.490 | 0.000 |
| 12 | | 20.215 | 11785 | 2301 | 0.237 | 1.165 | 0.000 |
| 13 | C11030405-D | 20.385 | 4713747 | 805969 | 94.727 | 1.064 | 1.233 |
| 14 | | 20.950 | 125355 | 20894 | 2.519 | 3.682 | 1.139 |
| 15 | | 21.414 | 2647 | 254 | 0.053 | 2.449 | 0.000 |
| 16 | | 21.640 | 6285 | 1030 | 0.126 | 1.177 | 1.248 |
| 17 | | 23.258 | 10898 | 1639 | 0.219 | 9.573 | 1.196 |
| 18 | | 26.264 | 3893 | 101 | 0.078 | 16.068 | 0.000 |
| 19 | | 26.544 | 2730 | -22 | 0.055 | 0.000 | 0.000 |
| Total | | | 4976125 | 844048 | 100.000 | | |

FIGURE 13A

| Angle | Gross Intensity | Rel. Intensity |
|---|---|---|
| 7.480 | 26763 | 36.1 % |
| 7.865 | 71070 | 99.9 % |
| 10.243 | 2731 | 1.8 % |
| 11.503 | 26338 | 35.9 % |
| 14.143 | 13831 | 17.8 % |
| 14.662 | 9827 | 11.9 % |
| 15.075 | 8244 | 9.5 % |
| 15.717 | 23198 | 30.9 % |
| 16.215 | 15608 | 19.9 % |
| 17.259 | 35171 | 48.0 % |
| 17.827 | 4213 | 3.4 % |
| 18.331 | 5418 | 5.1 % |
| 18.900 | 5805 | 5.7 % |
| 19.284 | 3321 | 2.2 % |
| 19.883 | 11600 | 14.2 % |
| 20.666 | 9151 | 10.8 % |
| 21.323 | 4072 | 3.6 % |
| 22.647 | 7600 | 8.7 % |
| 23.200 | 49092 | 68.5 % |
| 23.508 | 9521 | 11.5 % |
| 23.898 | 5524 | 5.8 % |
| 25.189 | 2426 | 1.4 % |
| 25.731 | 5964 | 6.6 % |
| 25.918 | 7909 | 9.4 % |
| 26.298 | 3235 | 2.7 % |
| 26.854 | 3821 | 3.7 % |
| 28.661 | 2447 | 1.7 % |
| 29.262 | 3383 | 2.9 % |
| 29.875 | 9667 | 11.9 % |
| 30.506 | 2377 | 1.3 % |
| 31.259 | 6070 | 6.5 % |

FIGURE 13B

| | | |
|---|---|---|
| 31.747 | 4072 | 3.6 % |
| 32.163 | 3742 | 3.2 % |
| 32.439 | 2981 | 2.1 % |
| 33.222 | 3680 | 3.1 % |
| 33.840 | 2837 | 2.0 % |
| 34.752 | 2652 | 1.7 % |
| 35.158 | 4656 | 4.6 % |
| 36.569 | 3175 | 2.4 % |
| 37.060 | 2596 | 1.6 % |
| 38.117 | 2485 | 1.5 % |
| 41.569 | 2096 | 1.2 % |
| 42.059 | 2746 | 2.1 % |
| 42.474 | 2736 | 2.0 % |
| 43.212 | 2912 | 2.2 % |
| 45.121 | 2373 | 1.6 % |
| 46.485 | 1759 | 0.8 % |
| 47.522 | 2251 | 1.5 % |
| 47.941 | 1842 | 1.0 % |

THIADIAZOLYL-OXIMINOACETIC ACID DERIVATIVE COMPOUNDS

CROSS REFERENCE TO RELATED APPLICATIONS

This application is a U.S. National Phase application under 35 U.S.C. § 371 of PCT Application No. PCT/US2015/066839, filed Dec. 18, 2015, which claims priority from U.S. Provisional Application No. U.S. 62/093,775, filed Dec. 18, 2014 and U.S. Provisional Application No. U.S. 62/097,861 filed Dec. 30, 2014.

2. TECHNICAL FIELD

This disclosure relates to the synthesis of chemical compounds, including intermediates such as thiadiazolyl-oximinoacetic acid derivatives useful in the manufacture of cephalosporins such as ceftolozane.

3. BACKGROUND

Ceftolozane is a cephalosporin antibacterial agent of the beta-lactam class (β-lactams), also referred to as CXA-101, FR264205, or by chemical names such as (6R,7R)-5-thia-1-azabicyclo[4.2.0]oct-2-ene-carboxylic acid, 3-[[4-[[[(2-aminoethyl)amino]carbamoyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo; or (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of formula (VI) that can be formulated for intravenous administration or infusion.

(VI)

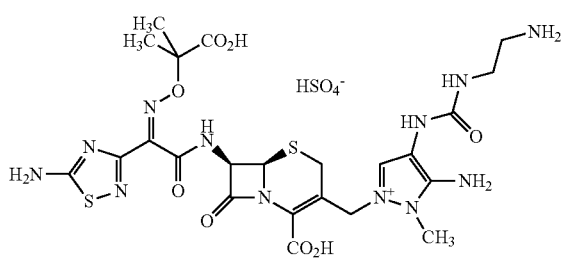

Ceftolozane sulfate is also referred to as: 1H-Pyrazolium, 5-amino-4-[[[(2-aminoethyl)amino]carbonyl]amino]-2-[[[(6R,7R)-7-[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-, sulfate (1:1); or 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate. Ceftolozane can be obtained as disclosed in U.S. Pat. No. 7,129,232 and in Toda et al., "Synthesis and SAR of novel parenteral anti-pseudomonal cephalosporins: Discovery of FR264205," *Bioorganic & Medicinal Chemistry Letters*, 18, 4849-4852 (2008), incorporated herein by reference. The antibacterial activity of ceftolozane is believed to result from its interaction with penicillin binding proteins (PBPs) to inhibit the biosynthesis of the bacterial cell wall which acts to stop bacterial replication.

Referring to FIG. 1, synthesis of ceftolozane can be performed via activation of the thiadiazolyl-oximinoacetic acid derivative (I) with methanesulfonyl chloride and $K_2CO_3$ in DMA at 10° C., followed by coupling with the 7-aminocephem (II) by means of $Et_3N$ in cold $EtOAc/H_2O$, affords amide (III). See U.S. Pat. Nos. 7,129,232 and 7,192,943, as well as Toda et al., "Synthesis and SAR of novel parenteral anti-pseudomonal cephalosporins: Discovery of FR264205," *Bioorganic & Medicinal Chemistry Letters*, 18, 4849-4852 (2008). Substitution of the allylic chloride of compound (III) with 4-[(N-Boc-aminoethyl)carbamoylamino]-1-methyl-5-tritylaminopyrazole (IV) in the presence of 1,3-bis(trimethylsilyl)urea (BSU) and KI in DMF then affords the protected pyrazolium adduct (v), which, after full deprotection with trifluoroacetic acid in anisole/$CH_2Cl_2$, can be isolated as the hydrogen sulfate salt by treatment with $H_2SO_4$ in i-PrOH/$H_2O$. The pyrazolyl urea intermediate (IV) can be prepared as follows referring to FIG. 2. Treatment of 5-amino-1-methylpyrazole (VII) with $NaNO_2/HCl$ in water at 5° C. gives the 4-nitrosopyrazole derivative (VIII), which can be reduced to the diaminopyrazole (IX) by catalytic hydrogenation over Pd/C in the presence of $H_2SO_4$. Selective acylation of the 4-amino group of compound (IX) with phenyl chloroformate in the presence of NaOH in $H_2O$/dioxane at 10° C. then yields the phenyl carbamate (X). After protection of the free amine group of carbamate (X) with chlorotriphenylmethane in the presence of $Et_3N$ in THF, the resulting N-trityl derivative (XI) can be coupled with N-Boc-ethylenediamine in the presence of $Et_3N$ in DMF to afford pyrazolyl urea (IV).

The thiadiazolyl-oximinoacetic acid derivative compound (I) is commercially available. However, compound (I) is commercially available in limited quantities on the scale of milligrams to grams. Accordingly, there is a need for methods of manufacturing compound (I) on a kilogram scale in high yield and high purity.

4. SUMMARY

Compound (1) (TATD) is commercially available (CAS No. 76028-96-1). It has now been discovered that the thiadiazolyl-oximinoacetic acid derivative compound (I) (TATD) can be prepared from dimethyl malonate (SM 1, CAS No. 108-59-8) according to methods described herein, e.g., the method depicted in Scheme 1A or Scheme 2 (the methods of the invention). The methods provide product having desirable purity.

Provided herein is a method of making a compound of formula (Z-I), e.g., compound (I), from a compound of formula SM Z-1, e.g., compound SM 1.

Also provided herein is a crystal form of compound (I) characterized by an X-ray powder diffraction (XRPD) pattern having peaks at angles (2 theta ±0.2) of 7.5, 7.9, 11.5, 15.7, 17.3, and 23.2.

Compounds useful in the synthesis of a compound of formula (Z-I), e.g., compound (I), include: (1) the compound identified as Int C in Scheme 2, and (2) the compound identified as Int E in Scheme 2. Processes useful in the synthesis of compound (I) include: (3) the formation of the compound Int C from the compound identified as Int B, and (4) the formation of the compound Int E from the compound Int B (e.g., including processes that increase the stability of a compound identified as Int E1 in Scheme 2 in situ during conversion of Int D to Int E).

Compound Int C is a mono-ester, mono-amide compound resulting from the selective amidation of one ester moiety of the diester compound Int B. The selectivity of the amidation is critical to obtaining high yields of a single oxime stereoisomer. In a preferred embodiment of the amidation reaction, compound Int C is prepared with unexpectedly high selectivity by using a reaction temperature of ≤0° C., and using conditions comprising ammonium hydroxide (e.g., $NH_3$/$H_2O$).

Compound Int C can be converted to compound Int D by dehydration of the primary amide of Int C via processes that include reaction with phosphorous pentachloride and pyridine. Compound Int D is converted to the imidate compound Int E1 and then to the amidine compounds Int E1 and Int E. Steps in the conversion of Int D to Int E can include: (1) conversion of Int D to Int E1 using conditions comprising sodium methoxide and methanol; (2) conversion of Int E1 to Int E2 using conditions comprising acetic acid and ammonium chloride; and (3) conversion of Int E2 to Int E using conditions comprising sodium hydroxide and hydrochloric acid. The conversion of Int E2 to Int E (i.e., saponification of the ester of Int E2 to yield the carboxylic acid of Int E) is critical to the viability of the synthesis procedure because the ester is difficult to saponify after formation of the thiadiazole ring.

The compounds Int C, Int D, and Int E, as well as the processes employing one or more of these compounds are useful, for example, in the manufacture of the compound of formula Z-I, e.g., compound (I) (TATD). For example, Int E can be converted to compound (I) by processes that include the use of $Br_2$ and $NH_4SCN$ (e.g., as described herein).

5. BRIEF DESCRIPTION OF THE FIGURES

Figure 1:
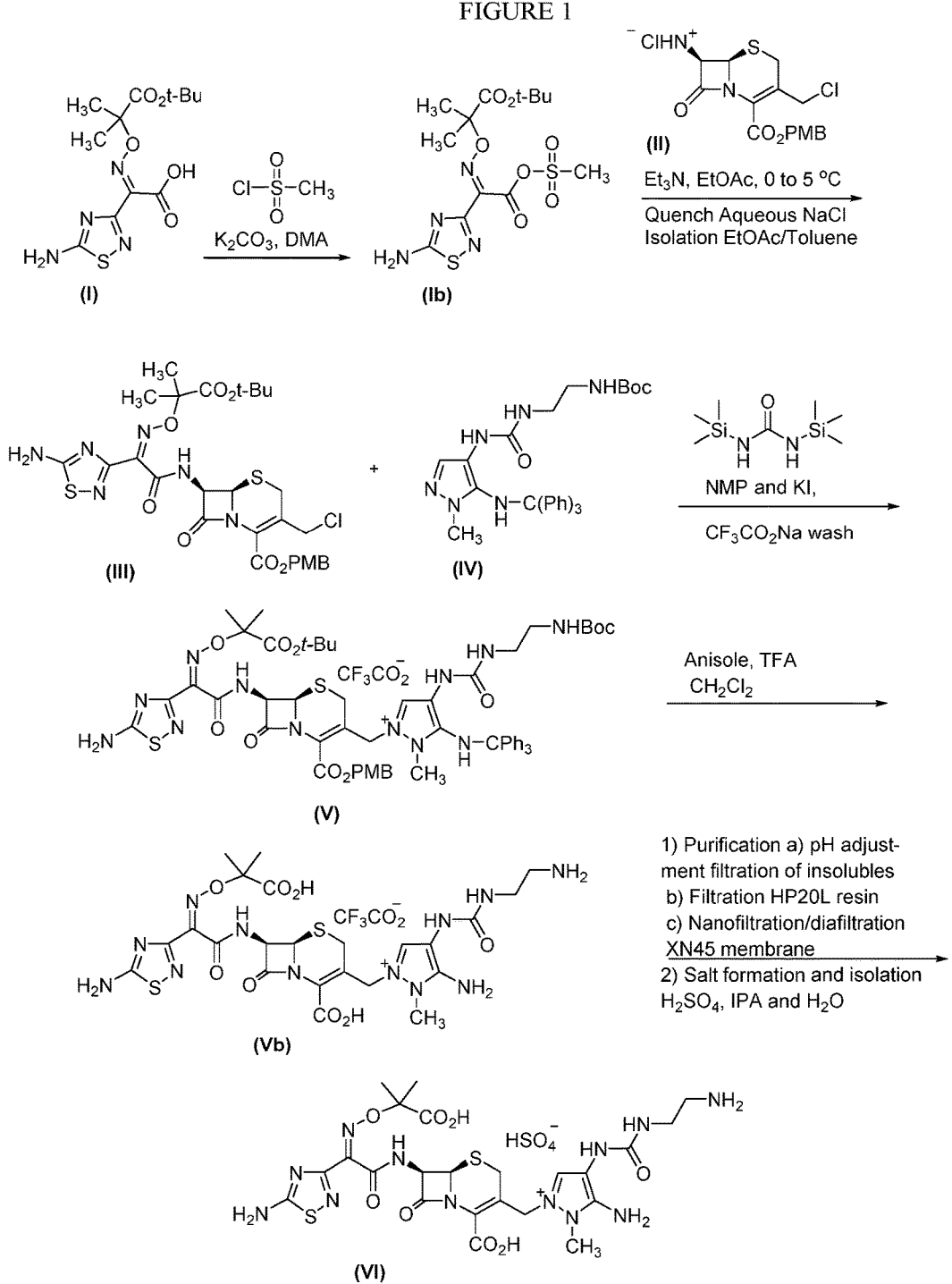
FIG. 1 shows a synthetic scheme to prepare compound (VI) (ceftolozane sulfate).
Figure 2:
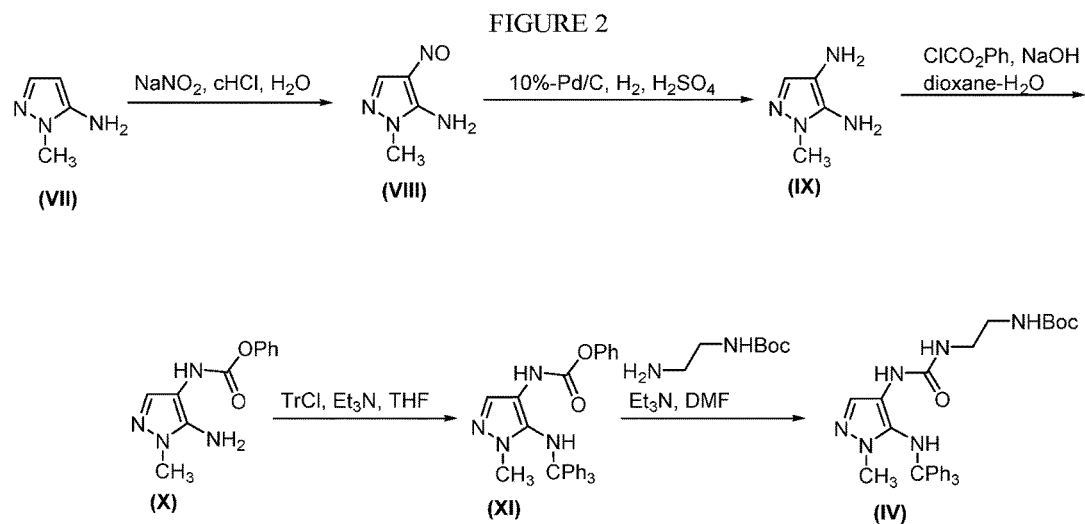
FIG. 2 shows a synthetic scheme to prepare intermediate compound (IV).
Figure 3:
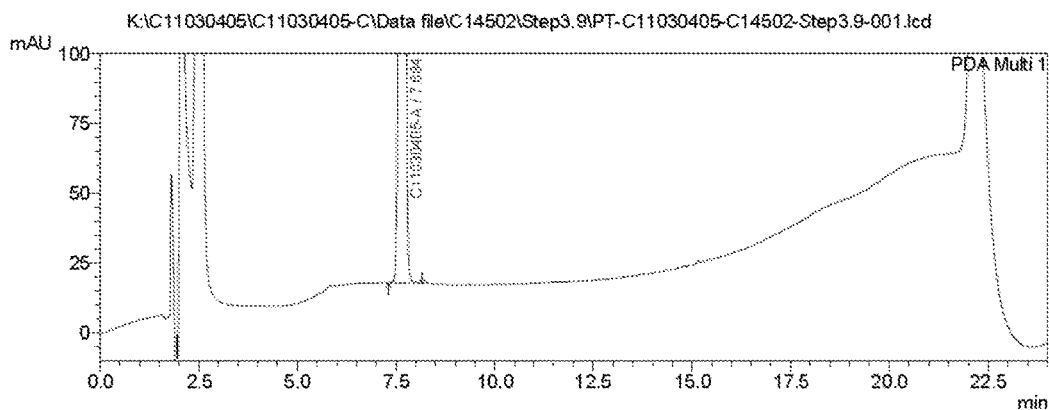
Figure 4:
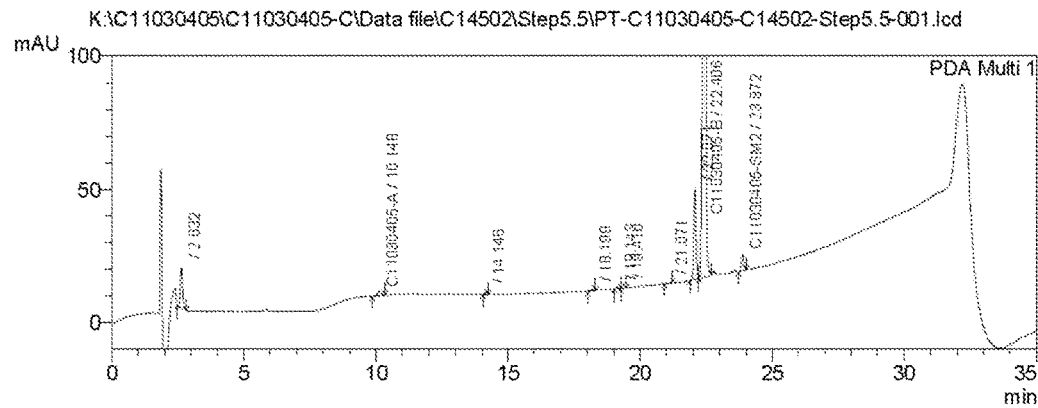
Figure 7:
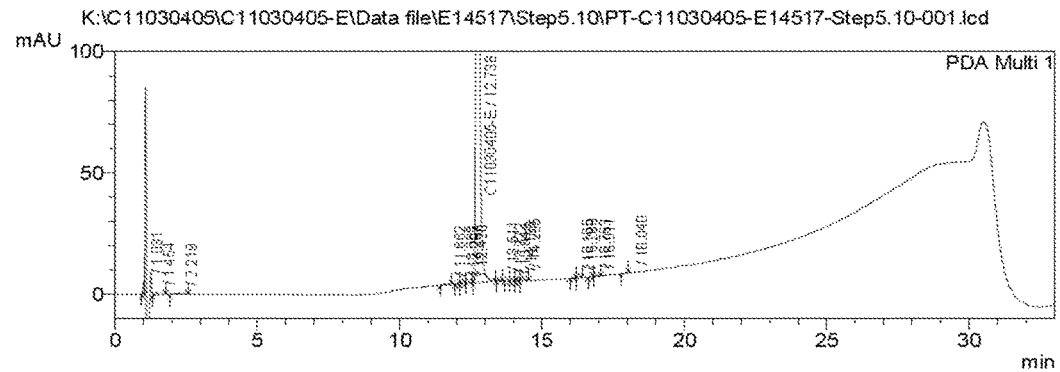
Figure 8:
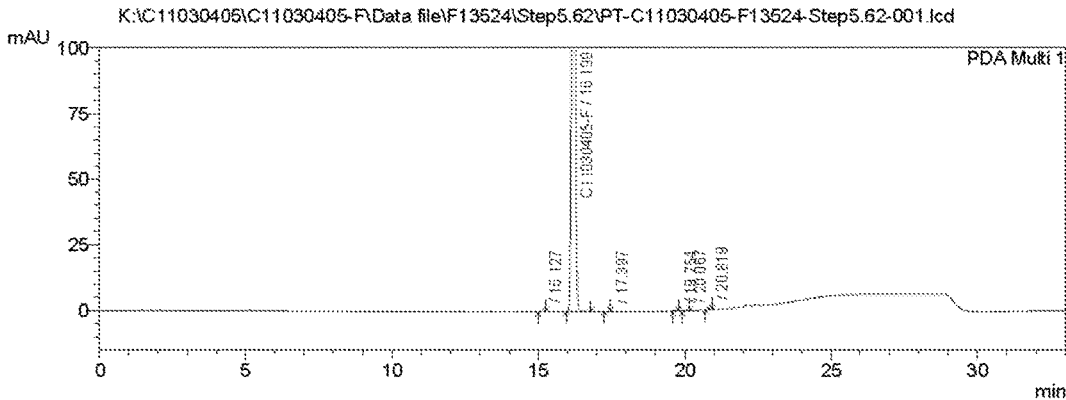
Figure 9:
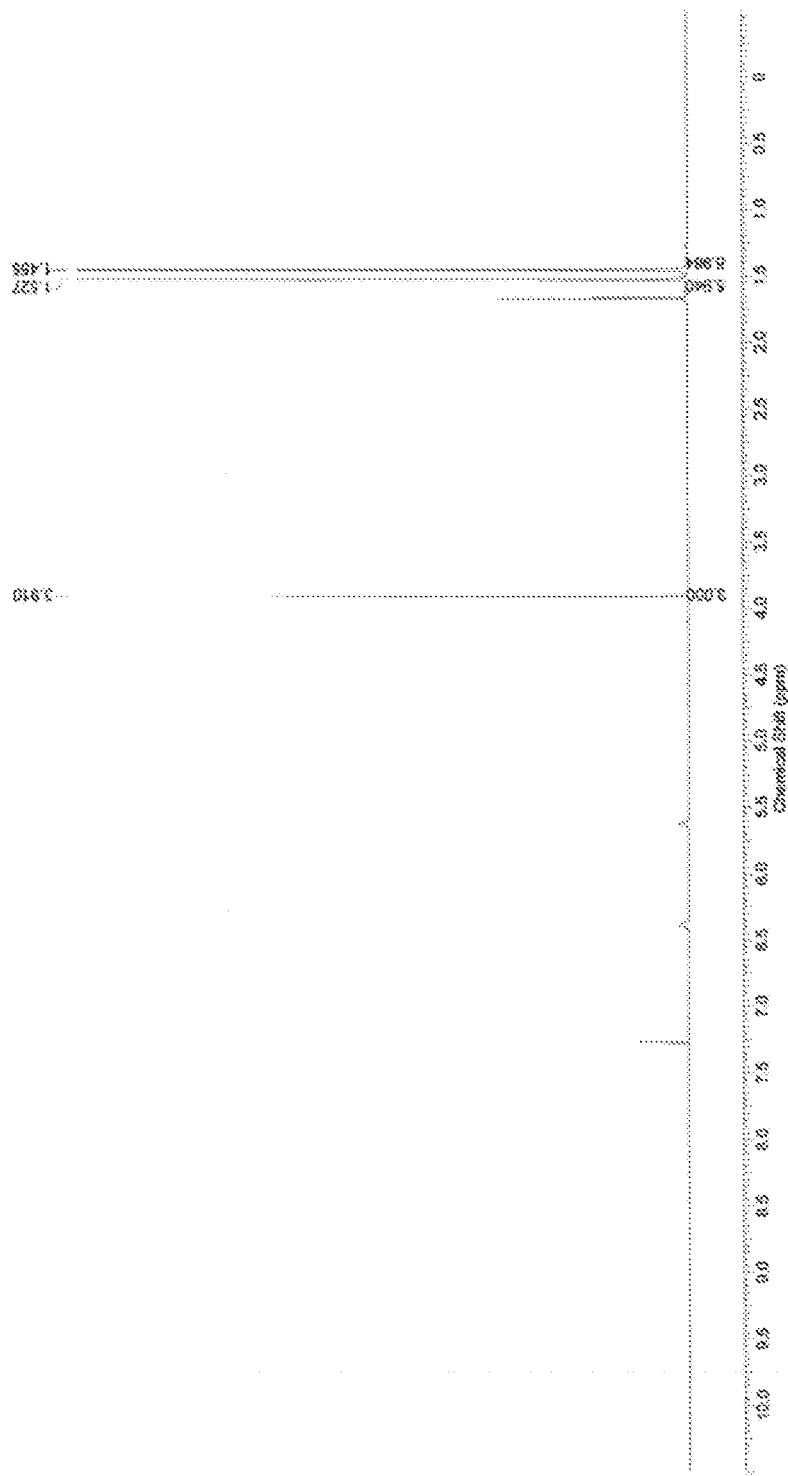
Figure 10:
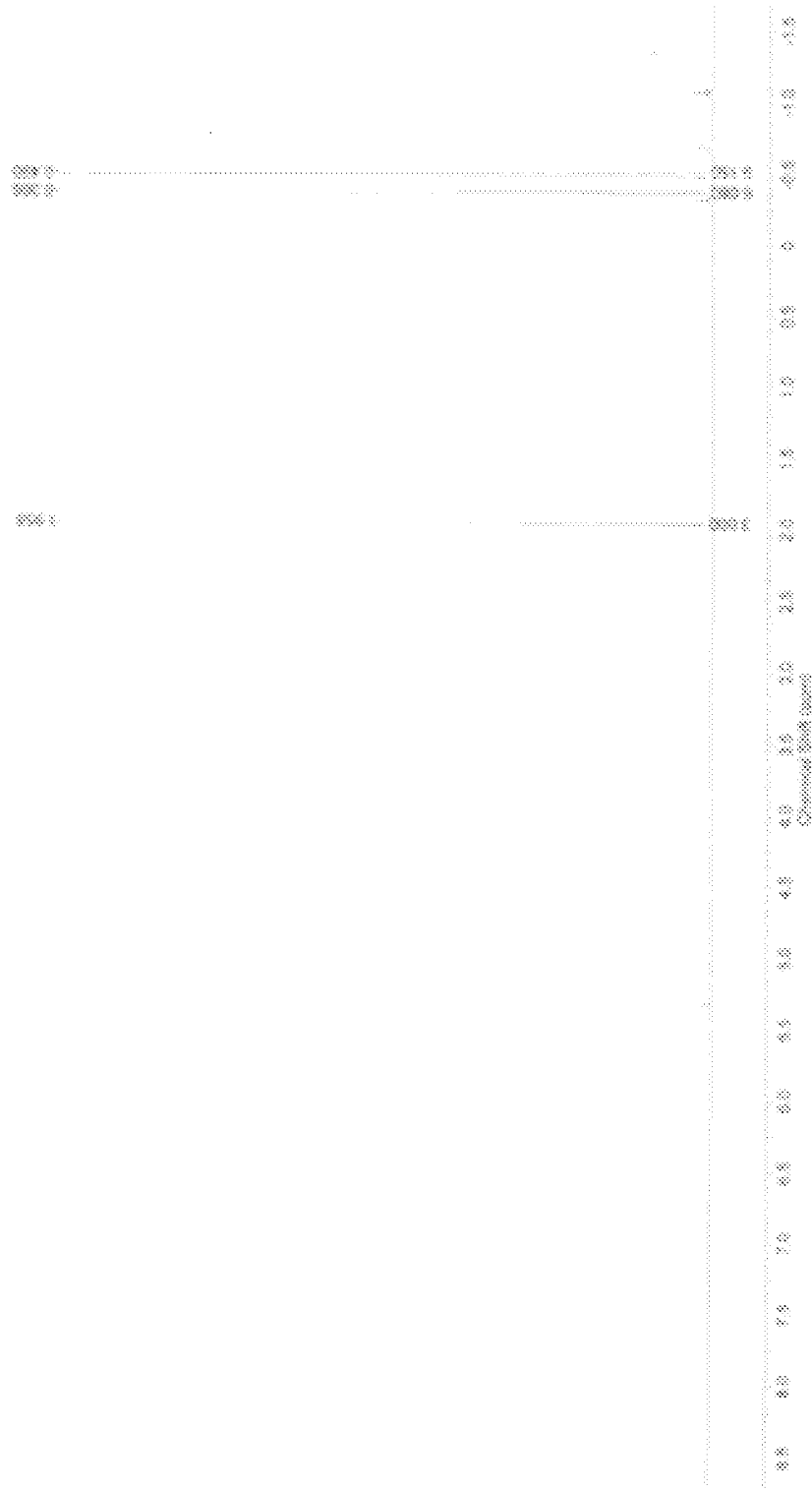
Figure 11:
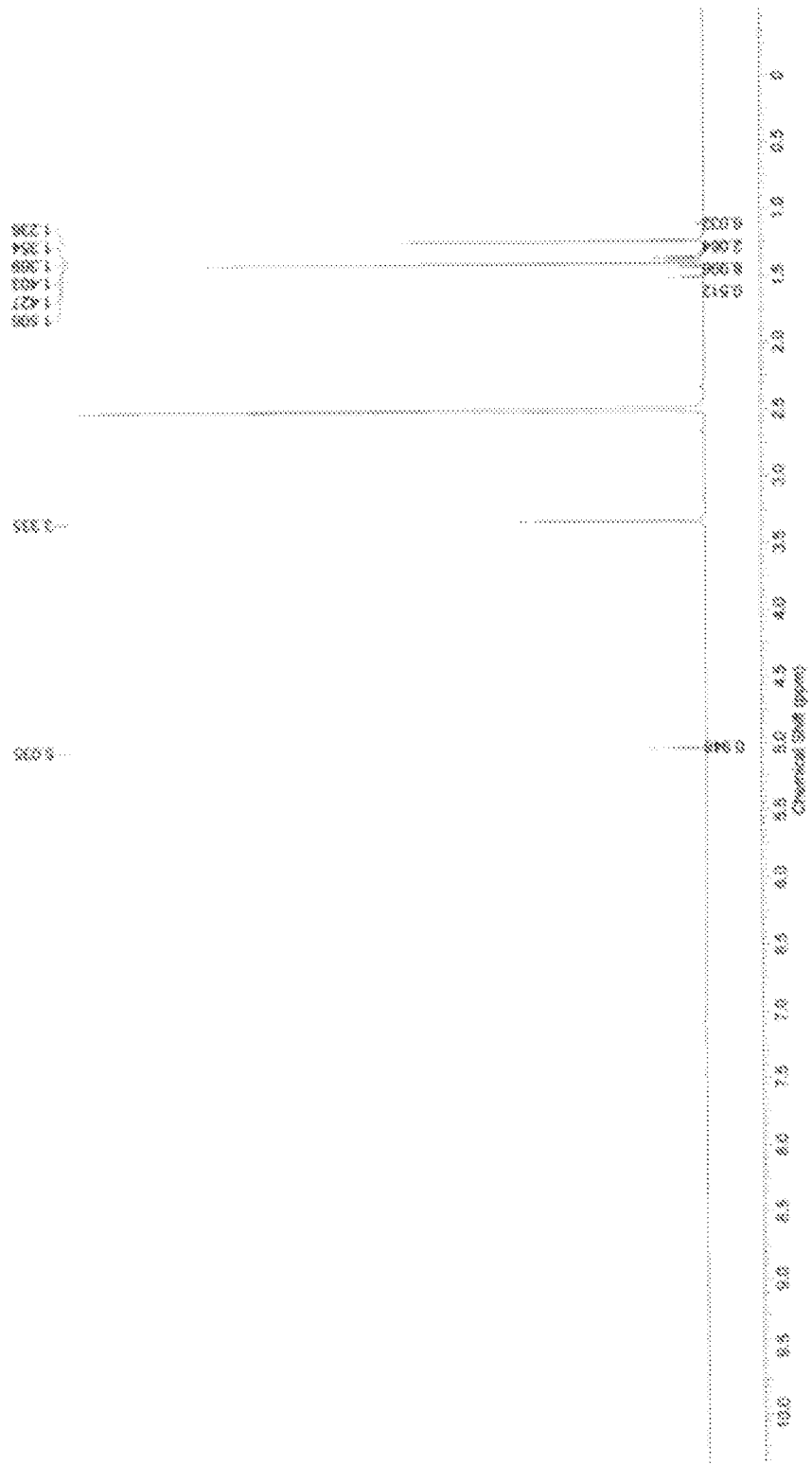
Figure 12:
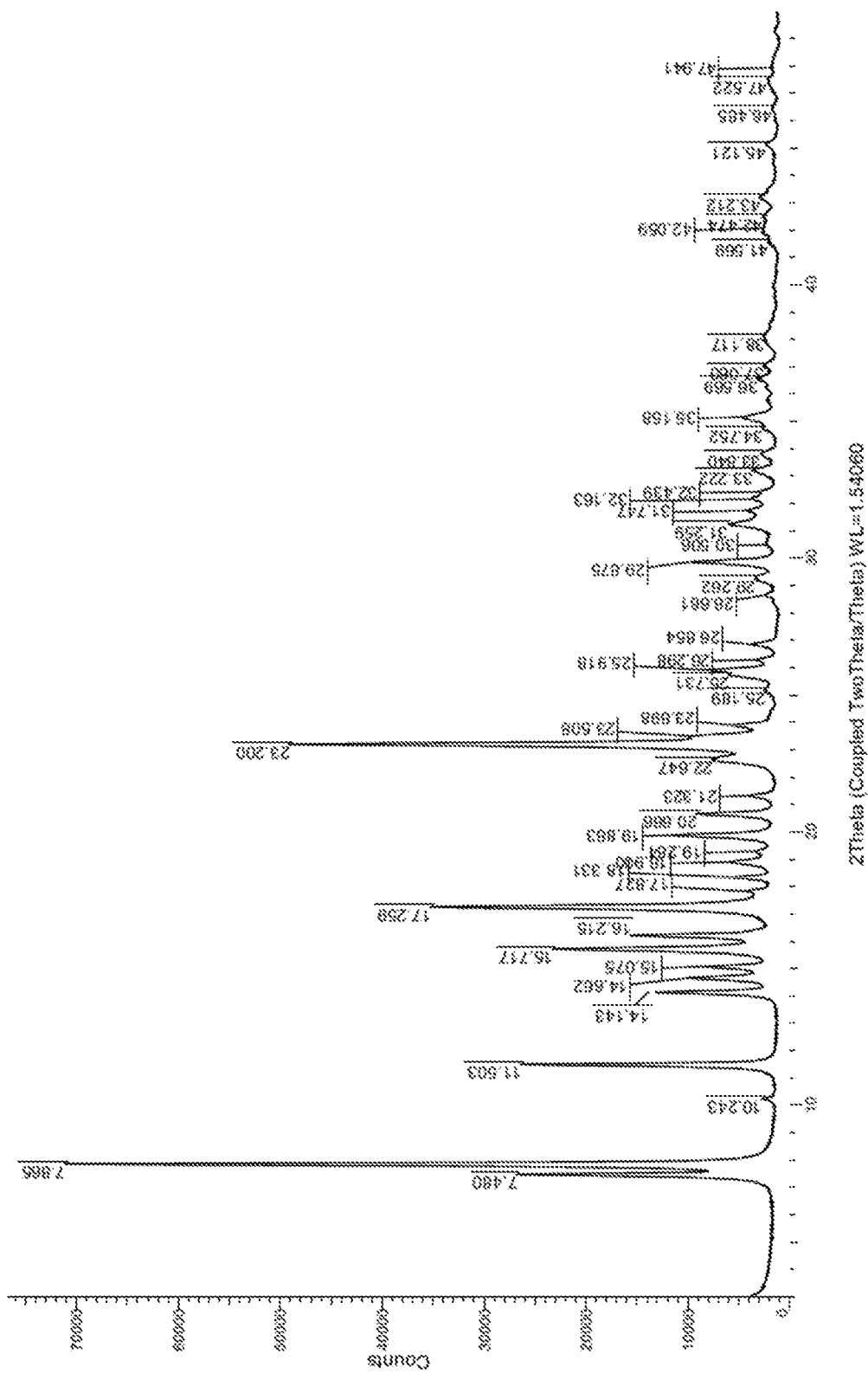

FIG. 3 shows an HPLC trace for compound Int A.
FIG. 4 shows an HPLC trace for compound Int B.
FIG. 5 shows an HPLC trace for compound Int C.
FIG. 6 shows an HPLC trace for compound Int D.
FIG. 7 shows an HPLC trace for compound Int E.
FIG. 8 shows an HPLC trace for compound (I) (TATD).
FIG. 9 shows a $^1$H-NMR spectrum of Int C.
FIG. 10 shows a $^1$H-NMR spectrum of Int D.
FIG. 11 shows a $^1$H-NMR spectrum of Int E.
FIG. 12 shows an X-ray powder diffraction (XRPD) pattern for compound (I).
FIGS. 13A and 13B show a listing of peaks for the XRPD pattern of compound (I).

6. DETAILED DESCRIPTION 6.1. Definitions

Unless otherwise defined herein, scientific and technical terms used in connection with the present disclosure shall have the meanings that are commonly understood by those of ordinary skill in the art.

Abbreviations: GC=gas chromatography; FID=flame ionization detector; KF=Karl-Fischer analysis; HPLC=high performance liquid chromatography; PDA=photodiode array; RSD=relative standard deviation; ACN=acetonitrile; TFA=trifluoroacetic acid.

The term "$C_{x-y}$ alkyl" refers to unsubstituted saturated hydrocarbon groups, including straight-chain alkyl and branched-chain alkyl groups that contain from x to y carbons in the chain. For example, $C_{1-6}$ alkyl is an alkyl group having two to six carbons. A "linear $C_{x-y}$ alkyl" refers to the "n" form of the alkyl group, for example, a "linear $C_6$ alkyl" is n-hexyl.

The term "hydroxyalkyl" refers to an alkyl group having one or more, e.g., one, two, or three, hydroxy (i.e., —OH) substituents.

As used herein, a "protecting group" is a moiety that masks the chemical reactivity of a functional group during one or more reactions. In an illustrative example, a nitrogen protecting group such as tert-butoxycarbonyl (i.e., tert-butyloxycarbonyl, Boc, or BOC) can be introduced at one step to mask the chemical reactivity of a protected nitrogen during one reaction then removed under acidic conditions to allow the formerly protected nitrogen to undergo reaction, e.g., alkylation. A protecting group can be any one known in the art, such as those described in Wuts, P. G. M.; Greene, T. W. Greene's Protective Groups in Organic Synthesis, 4$^{th}$ ed; John Wiley & Sons: Hoboken, N.J., 2007, or can be one that is developed in the future.

Oxygen and nitrogen protecting groups are known to those of skill in the art. Oxygen protecting groups include, but are not limited to, methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few), amides, cyclic imide derivatives, N-alkyl and N-aryl amines, benzyl amines, substituted benzyl amines, trityl amines, imine derivatives, and enamine derivatives, for example.

In some embodiments, the oxygen protecting group is a base-labile protecting group (i.e., one that can be removed under basic conditions), such as a methyl group when used as an ester to protect a carboxylic acid. In some embodiments, the oxygen protecting group is an acid-labile oxygen protecting group (i.e., one that can be removed under acid conditions), such as tert-butyl, 4-methoxybenzyl, or triphenylmethyl. In some embodiments, the oxygen protecting group is an oxidation-reduction sensitive oxygen protecting group, such as a benzyl ether which is removed under catalytic hydrogenation conditions. In some embodiments, the oxygen protecting group is a silyl ether, such as TBDMS, TIPS, or TES, which is removed with nucleophilic fluoride.

In some embodiments, the nitrogen protecting group is a base-labile nitrogen protecting group (i.e., one that is removed under basic conditions), such as 9-fluorenylmethyl carbamate (Fmoc). In some embodiments, the nitrogen protecting group is an acid-labile nitrogen protecting group (i.e., one that is removed under acid conditions), such as triphenylmethyl, tert-butyl, tert-butoxycarbonyl, 2-trimethylsilylethoxycarbonyl (Teoc), or 4-methoxybenzyloxycarbonyl. In some embodiments, the nitrogen protecting group is an oxidation-reduction sensitive nitrogen protecting group, such as a benzyl, which can be removed under catalytic hydrogenation conditions.

The terms "amine" and "amino" are art-recognized and refer to both unsubstituted and substituted amines and salts thereof, e.g., a moiety that can be represented by the general formulae:

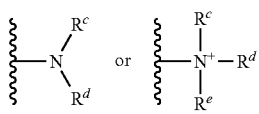

wherein $R^c$, $R^d$, and $R^e$ each independently represent a hydrogen, an alkyl, an alkenyl, —$(CH_2)_m$—$R^f$, or $R^c$ and $R^d$ taken together with the N atom to which they are attached complete a heterocycle having from 4 to 8 atoms in the ring structure; $R^f$ represents an aryl, a cycloalkyl, a cycloalkenyl, a heterocyclyl or a polycyclyl; and m is zero or an integer from 1 to 8. In preferred embodiments, only one of $R^c$ and $R^d$ is a carbonyl, e.g., $R^c$, $R^d$, and the nitrogen together do not form an imide. In even more preferred embodiments, $R^c$ and $R^d$ (and optionally $R^e$) each independently represent a hydrogen, an alkyl, an alkenyl, or —$(CH_2)_m$—$R^f$. In certain embodiments, the amino group is basic, meaning the protonated form has a $pK_a \geq 7.00$.

As used herein, an "organic base" is an organic compound comprising at least one basic amino group. The organic base may comprise an alkyl amine, such as triethylamine, diethylamine, and/or diisopropylethylamine, and/or a cyclic amine, such as morpholine, piperidine, piperazine, pyrrolidine, cyclobutylamine, and/or cycloheptylamine.

As used herein, an alcohol includes an organic compound that is or comprises a hydroxyalkyl group. Exemplary alcohols include methanol, ethanol, isopropanol, n-propanol, n-butanol, sec-butanol, tert-butanol, and n-pentanol. In an illustrative example, an alcohol can comprise, consist essentially of, or consist of methanol.

Compound (I) is also known as "TATD" and "(Z)-2-(5-amino-1,2,4-thiadiazol-3-yl)-2-(((1-(tert-butoxy)-2-methyl-1-oxopropan-2-yl)oxy)imino)acetic acid" and has the structure shown below.

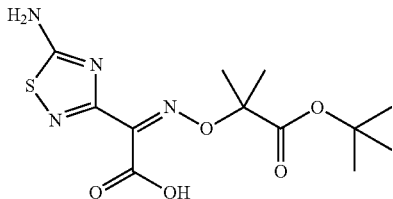

(I)

6.2. General Method of Making a Compound of Formula (Z-I)

A general sequence to make a compound of formula (Z-I), e.g., compound (I), is shown in Scheme 1A below. A suitable starting material of a compound of formula SM Z-1 is a malonate. In some embodiments, $R^1$ and $R^2$ are each independently $C_{1-6}$ alkyl, preferably $C_{1-3}$ alkyl, for example, Me, Et, or iPr. $R^1$ and $R^2$ can be the same or different. In some embodiments, a compound of formula SM Z-1 is dimethyl malonate ($R^1=R^2=$Me) or diethyl malonate ($R^1=R^2=$Et).

The compound of formula SM Z-1 is converted into an isonitrosomalonate of formula Int Z-A by contacting the compound of formula SM Z-1 with an NO source. Any one of appropriate conditions using an NO source, such as that described in *Organic Syntheses* 1960, 40, 21, which describes using sodium nitrite in aqueous acetic acid as an NO source, can be used to afford Int Z-A. The method optionally comprises a general aqueous workup procedure, such as addition of brine solution and extraction with an ethereal solvent, such as diethyl ether or methyl tert-butyl ether (MTBE).

In some embodiments, the compound of formula SM Z-1 has the structure of compound SM 1 as described herein.

In some embodiments, the compound of formula Int Z-A has the structure of compound Int A.

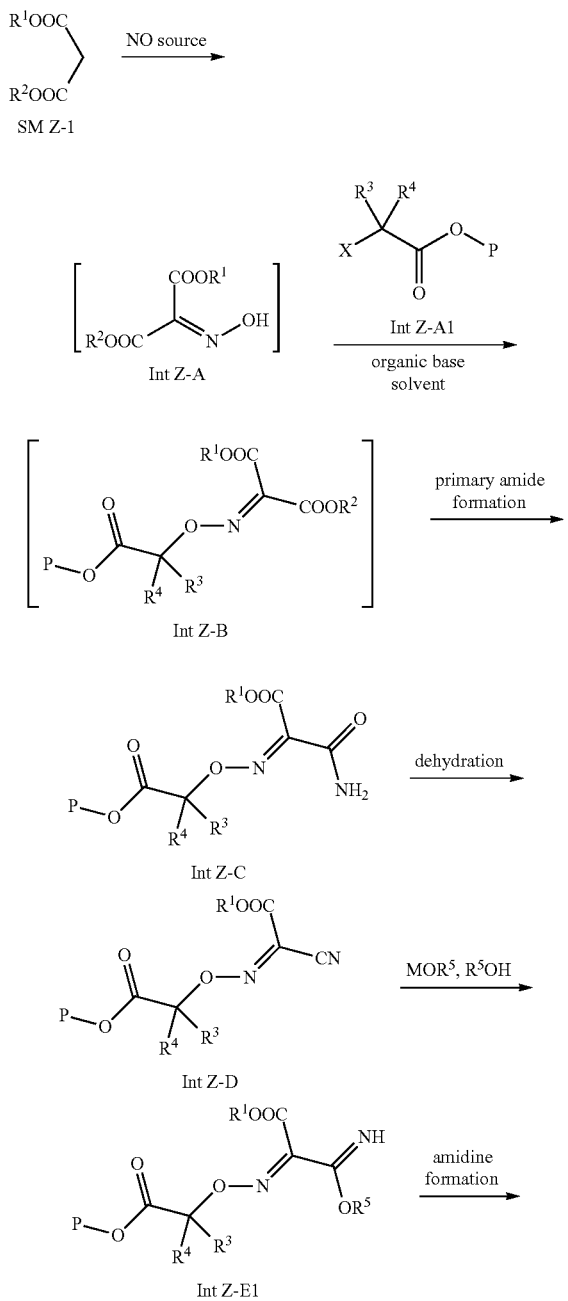

Scheme 1A

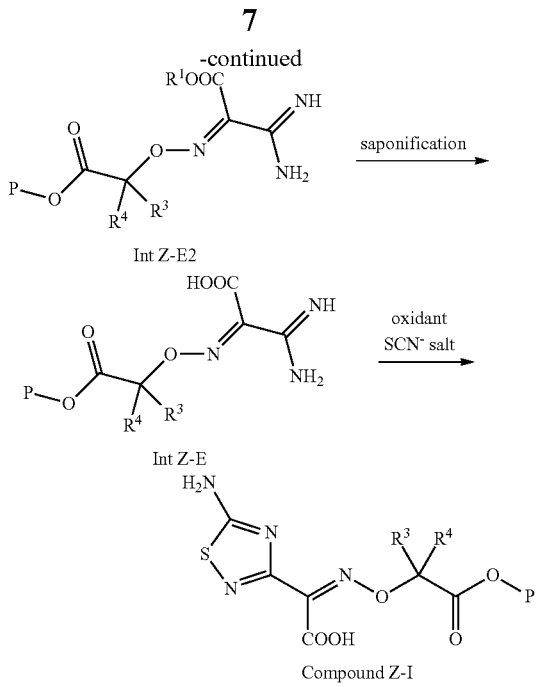

Int Z-E2 oxidant
SCN⁻ salt

Int Z-E

Compound Z-I

The compound of formula Int Z-A is admixed with a compound of formula Int Z-A1 and, optionally, an organic base, such as triethylamine or diisopropylethylamine, in an appropriate solvent, such as tetrahydrofuran (THF), dimethylformamide (DMF) or dimethylacetamide (DMA), for alkylation of the nitroso oxygen to afford a compound of formula Int Z-B.

In some embodiments, X is halo, such as Cl or Br.

In some embodiments, $R^3$ and $R^4$ are each independently $C_{1-6}$ alkyl, preferably $C_{1-3}$ alkyl, for example, Me, Et, or iPr. $R^3$ and $R^4$ can be the same or different. In some embodiments, $R^3$ is methyl. In some embodiments, $R^4$ is methyl.

In other embodiments, $R^3$ and $R^4$ taken together is a $C_{3-7}$ cycloalkyl, such as cyclopentyl or cyclohexyl.

In some embodiments, P is an oxygen protecting group, preferably an acid-labile oxygen-protecting group, such as tert-butyl.

In some embodiments, the compound of formula Int Z-A1 has the structure of compound SM 2 as described below.

In some embodiments, the compound of formula Int Z-B has the structure of compound Int B.

The compound of formula Int Z-B can be converted to a compound of formula Int Z-C by any one of appropriate methods to synthesize a primary amide from an ester, such as contacting the compound of formula Int Z-B with ammonia, optionally in the presence of an alcohol $R^1OH$.

In some embodiments, the compound of formula Int Z-C has the structure of compound Int C.

The compound of formula Int Z-C is then dehydrated to a nitrile of formula Int Z-D by any method to dehydrate a primary amide to a nitrile. A number of methods using reagents, such as phosphorus pentachloride in pyridine, phosphorus oxychloride, or oxalyl chloride, are known in the art to be able to dehydrate a primary amide to a nitrile.

In some embodiments, the compound of formula Int Z-D has the structure of compound Int D.

The compound of formula Int Z-D is then contacted with a compound of formula $MOR^5$ in an alcohol $R^5OH$ to form an imidate of formula Int Z-E1. In some embodiments, $R^5$ is $C_{1-6}$ alkyl, preferably $C_{1-3}$ alkyl, for example, Me or Et. The compound of formula $MOR^5$ is a metal alkoxide, wherein M is a metal. In some embodiments, M is an alkali metal, e.g., lithium, sodium, or potassium.

In some embodiments, the compound of formula Int Z-E1 has the structure of compound Int E1.

The compound of formula Int Z-E1 is admixed with an ammonia source to give an amidine of formula Int Z-E2, which can then be contacted with a base to saponify an ester. In an illustrative example, saponification of a compound of formula Int Z-E2 and subsequent workup can occur by contacting with sodium hydroxide followed by hydrochloric acid to afford an acid of formula Int Z-E. The ammonia source can be ammonia (introduced either as a free gas or already dissolved in a liquid solvent, e.g., methanol) or an ammonium salt, such as ammonium chloride, ammonium bromide, or ammonium acetate. In some embodiments, the compound of formula Int Z-E2 has the structure of compound Int E2.

Scheme 1B

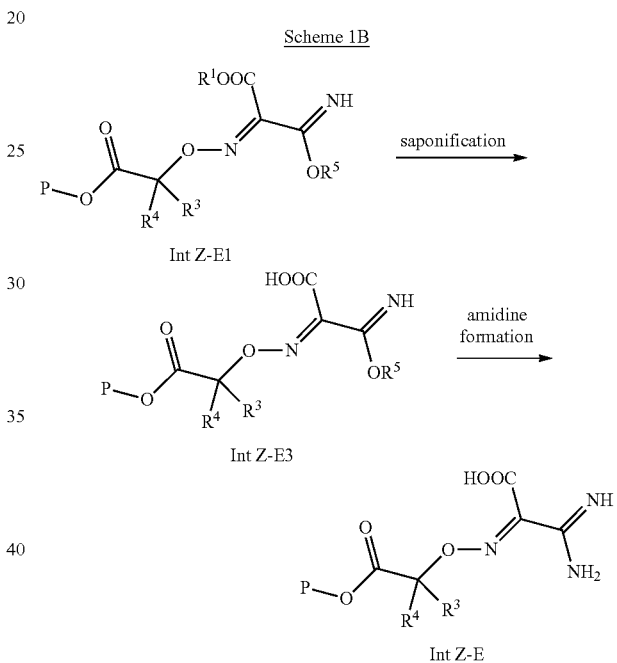

Int Z-E1 amidine formation

Int Z-E3

Int Z-E

Scheme 1B depicts an alternate sequence to make a compound of formula Int Z-E from a compound of formula Int Z-E1. In some embodiments, the compound of formula Int Z-E1 is converted to a compound of formula Int Z-E by first saponification (e.g., by admixing the compound of formula Z-E1 with a base, such as an aqueous base, for example, a sodium hydroxide solution) to provide a compound of formula Int Z-E3, and then contacting the admixture with an ammonia source. As shown in Scheme 1B, in such cases, Int Z-E1 can be converted to Int Z-E without proceeding through Int Z-E2.

In some embodiments, the conversion of the compound of formula Int Z-E1 to a compound of formula Int Z-E comprises any combination of the aforementioned processes (e.g., partial conversion of the compound of formula Int Z-E1 by saponification and then admixing with ammonia as shown in Scheme 1B, then a sequence comprising admixing ammonia followed by saponification as shown in Scheme 1A to effect complete conversion).

In some embodiments, the compound of formula Int Z-E has the structure of compound Int E.

Admixing the amidine portion of a compound of formula Int Z-E under appropriate conditions with an oxidant, such as chlorine, bromine, or iodine, and a thiocyanate salt, e.g., ammonium thiocyanate, sodium thiocyanate, or potassium thiocyanate, optionally with an organic base such as triethylamine, gives a compound of formula (Z-I).

In some embodiments, the compound of formula (Z-1) has the structure of compound (I).

6.3. Method of Making Compound (I)

In some embodiments, the method of making compound (I) (TATD) comprises the steps shown in Scheme 2.

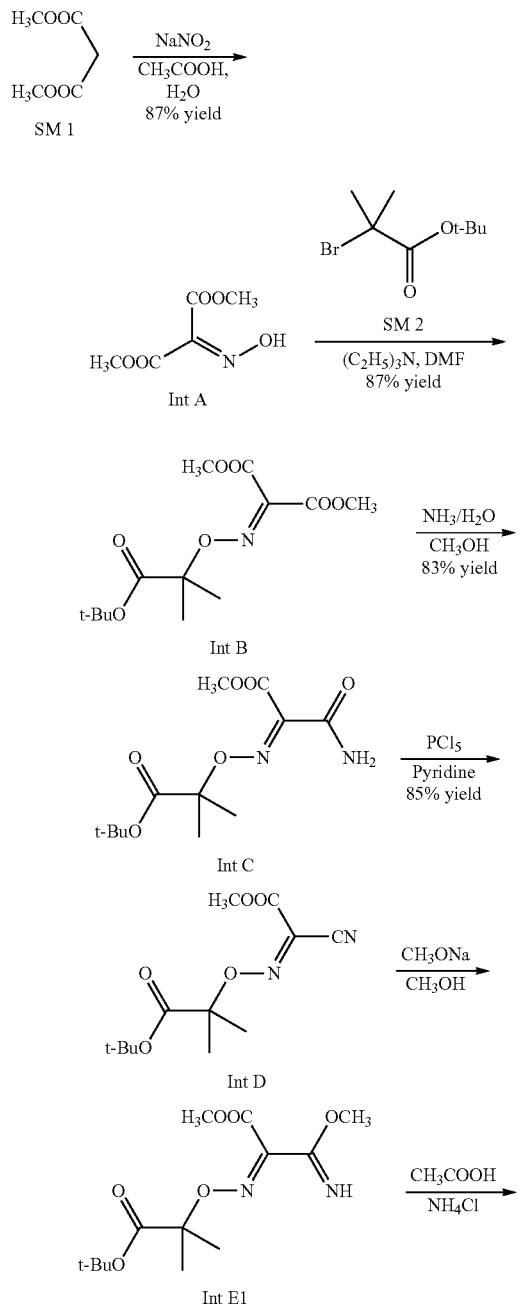

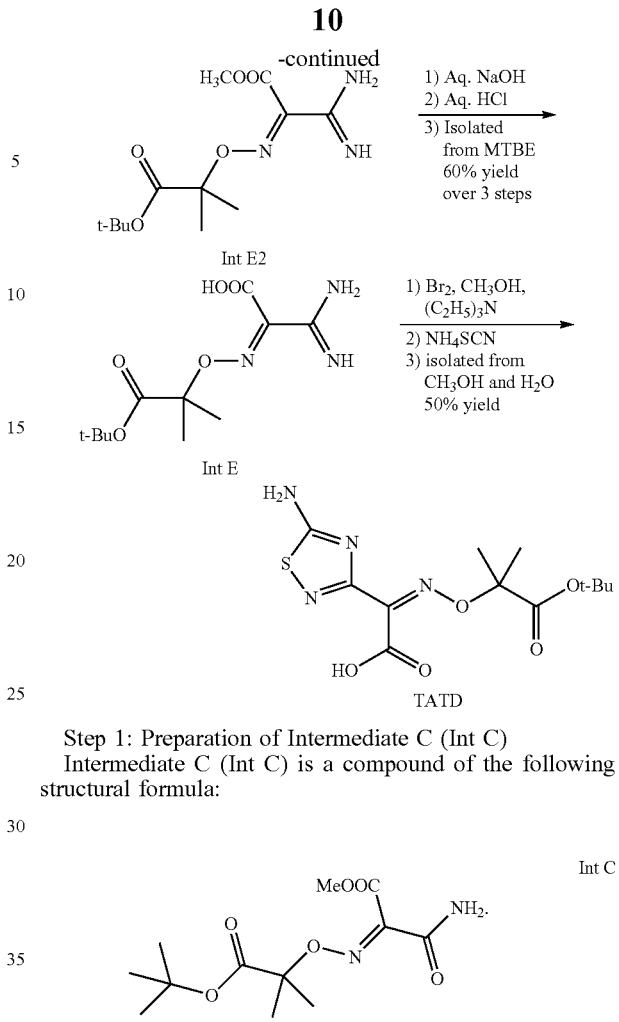

Step 1: Preparation of Intermediate C (Int C)

Intermediate C (Int C) is a compound of the following structural formula:

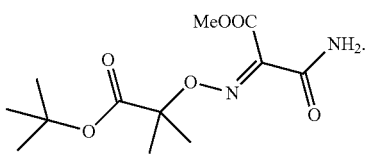

In some embodiments, the process parameters for the preparation of compound Int A are as listed in Table 1.

TABLE 1

Process parameters for the preparation of Int A

| Process Parameter | Impact Assessment (high, medium, low) | Normal Operating Range | Target |
|---|---|---|---|
| $H_2O$ (vol) | low | 1.45-1.50 | 1.47 |
| $NaNO_2$ (equiv) | low | 1.53-1.59-0.83 | 1.56 |
| AcOH (equiv) | low | 2.16-2.24 | 2.2 |
| Reaction Temperature (° C.) | low | 20 to 30 | 25 |

In some embodiments, the process parameters for the isolation of compound Int A are as listed in Table 2.

TABLE 2

Process parameters for the quench and workup of Int A

| Process Parameter | Impact Assessment (high, medium, low) | Normal Operating Range | Target |
|---|---|---|---|
| Quench and aqueous workup temperature (° C.) | low | 20 to 30 | 25 |

TABLE 2-continued

Process parameters for the quench and workup of Int A

| Process Parameter | Impact Assessment (high, medium, low) | Normal Operating Range | Target |
|---|---|---|---|
| NaCl concentration (w/w %) | low | 24.9-25.7 | 25 |
| 25% NaCl 1st wash (vol) | low | 0.79-0.92 | 0.83 |
| MTBE (vol) | low | 2.84-3.24 | 2.97 |
| MTBE back extract (vol) | low | 2.84-3.24 | 2.97 |
| H$_2$O (vol) | low | 1.90-2.20 | 2.00 |
| NaHCO$_3$ (equiv) | low | 0.80-0.83 | 0.83 |
| 25% NaCl 2nd wash (vol) | low | 0.79-0.92 | 0.83 |

In some embodiments, the process parameters for the preparation of compound Int B are as listed in Table 3.

TABLE 3

Process parameters for the preparation of Int B

| Process Parameter | Impact Assessment (high, medium, low) | Normal Operating Range | Target |
|---|---|---|---|
| Reaction Temperature (° C.) | medium | 45 to 50 | 47 |
| DMF (vol) | low | 4.56-4.77 | 4.73 |
| Et$_3$N (equiv) | low | 1.89-1.96 | 1.92 |
| C11030405-SM2 (equiv) | medium | 1.01-1.07 | 1.03 |

In some embodiments, the process parameters for the isolation of compound Int B are as listed in Table 4.

TABLE 4

Process parameters for the quench and workup of Int B

| Process Parameter | Impact Assessment (high, medium, low) | Normal Operating Range | Target |
|---|---|---|---|
| Aqueous workup temperature (° C.) | low | 0 to 10 | 5 |
| MTBE (vol) | low | 3.91-4.31 | 4.05 |
| H$_2$O (vol) | low | 2.00-2.50 | 2.30 |
| 2N HCl (vol) | medium | 3.0-3.2 | 3.26 |
| MTBE back extract (vol) | low | 1.75-2.16 | 1.96 |
| 25% NaCl 1st wash (vol) | low | 1.83-2.08 | 1.92 |
| 25% NaCl 2nd wash (vol) | low | 1.83-2.08 | 1.92 |
| Batch volume after concentration (vol) | medium | 2.0-2.3 | 2.1 |

In some embodiments, the process parameters for the preparation of compound Int C are as listed in Table 5.

TABLE 5

Process parameters for the preparation of Int C

| Process Parameter | Impact Assessment (high, medium, low) | Normal Operating Range | Target |
|---|---|---|---|
| Aqueous workup temperature (° C.) | medium | −5 to 5 | 0 |
| MeOH (vol) | medium | 2.4-2.7 | 2.52 |
| 25% NH$_3$/H$_2$O (vol) | medium | 1.00-1.02 | 1.02 |
| NH$_3$/H$_2$O (concentration) | medium | 25.0-28.0 | 25 |

In some embodiments, the process parameters for the isolation of compound Int C are as listed in Table 6.

TABLE 6

Process parameters for the quench and workup of Int C

| Process Parameter | Impact Assessment (high, medium, low) | Normal Operating Range | Target |
|---|---|---|---|
| H$_2$O (vol) | medium | 3.90-4.00 | 3.95 |
| 2N HCl (pH range) | medium | 5-6 | 5 |
| Batch volume after concentration (vol) | low | 9-11 | 10 |
| H$_2$O wash (vol) | low | 0.15-0.25 | 0.2 |
| MeOH/H$_2$O wash (vol) | low | 0.25-0.35 | 0.3 |
| MeOH/H$_2$O wash (w/w %) | low | 19.5-21.0 | 20 | w/w % = percentage by equivalent weight ratio (i.e., kg agent per kg compound Int C × 100)

Table 7 describes certain analytical data measured during the preparation of compound Int C from compound SM 1 according to the synthetic scheme detailed in Scheme 2 above.

TABLE 7

List of in-process controls for Int C

| Analytical Test | Analytical Method | Target Results | Typical Result |
|---|---|---|---|
| Consumption of SM 1 | GC | ≤0.5% | 0.5% |
| Assay of Int A | HPLC | Report | 17.4% (w/w) |
| Consumption of Int A | HPLC | ≤2.0% | 1.4% |
| Assay of Int B | HPLC | Report | 72.1% (w/w) |
| Consumption of Int B | HPLC | ≤1.0% | 0.3% |
| Purity of Int C in wet cake | HPLC | ≥85% | 94.5% |
| Residual water content in Int C | KF | ≤0.5% | 0.4%/0.2% |
| Assay of Int C | HPLC | Report | 92.6%/93.7% |

Step 2: Preparation of Intermediate D (Int D)

Intermediate D (Int D) is a compound of the following structural formula:

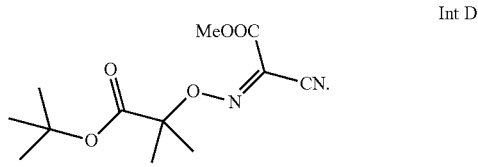 [SMILES: COC(=O)/C(C#N)=N\OC(C)(C)C(=O)OC(C)(C)C]

Int D

In some embodiments, the process parameters for the preparation of compound Int D are as listed in Table 8.

TABLE 8

Process parameters for the preparation of Int D

| Process Parameter | Impact Assessment (high, medium, low) | Normal Operating Range | Target |
|---|---|---|---|
| MTBE (vol) | low | 2.58-2.85 | 2.70 |
| PCl$_5$ (equiv) | medium | 1.21-1.24 | 1.22 |
| Pyridine (equiv) | medium | 6.96-7.32 | 7.0 |
| Reaction Temperature (° C.) | medium | 15-20 | 17 |

In some embodiments, the process parameters for the isolation of compound Int D are as listed in Table 9.

TABLE 9

Process parameters for the quench and workup of Int D

| Process Parameter | Impact Assessment (high, medium, low) | Normal Operating Range | Target |
|---|---|---|---|
| H₂O (vol) | low | 2.9-3.1 | 3.0 |
| Batch pH | low | 2-4 | 3 |
| Work up temperature (° C.) | low | 20 to 30 | 25 |
| NaCl solution (w/w %) | low | 24.9-25.7 | 25 |
| 25% NaCl solution for 1st wash (vol) | low | 1.58-1.75 | 1.67 |
| MeOH 1st wash (vol) | medium | 0.28-0.32 | 0.30 |
| 25% NaCl solution for 2nd wash (vol) | low | 1.58-1.75 | 1.67 |
| MeOH 2nd wash (vol) | medium | 0.14-0.18 | 0.15 |
| Activated carbon (w/w %) | low | 0.18-0.20 | 0.2 |
| Carbon treatment temperature (° C.) | low | 50 to 55 | 52 |
| Batch volume after 1st concentration (vol) | medium | 1.0-1.5 | 1.0 |
| MeOH (vol) | medium | 1.0-1.25 | 1.22 |
| Batch volume after 2nd concentration (vol) | medium | 1.0-1.5 | 1.0 | w/w % = percentage by equivalent weight ratio (i.e., kg agent per kg Int D × 100)

Table 10 describes certain analytical data measured during the preparation of compound Int D from compound Int C according to the synthetic scheme detailed in Scheme 2 above.

TABLE 10

List of in-process controls for Int D

| Analytical Test | Analytical Method | Target Results | Typical Result |
|---|---|---|---|
| Consumption of Int C | HPLC | ≤1.0% | 0.2% |
| Residual water content in Int D | KF | ≤0.2% | 0.01% |
| Assay of Int D | HPLC | ≥80% | 95.4% |

Step 3: Preparation of Intermediate E (Int E)

Intermediate E (Int E) is a compound of the following structural formula:

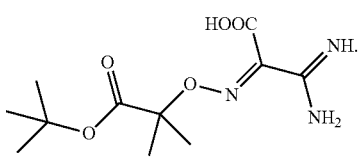

Int E

In some embodiments, the process parameters for the preparation of compound Int D are as listed in Table 11.

TABLE 11

Process parameters for the preparation of Int E

| Process Parameter | Impact Assessment (high, medium, low) | Normal Operating Range | Target |
|---|---|---|---|
| MeOH (vol) | low | 4.30-4.56 | 4.55 |
| Reaction temperature (° C.) | medium | 15 to 18 | 17 |
| Batch pH adjustment with AcOH | medium | 6-7 | 6.5 |
| NH₄Cl (equiv) | medium | 1.01-1.11 | 1.10 |

TABLE 11-continued

Process parameters for the preparation of Int E

| Process Parameter | Impact Assessment (high, medium, low) | Normal Operating Range | Target |
|---|---|---|---|
| NaOH aqueous solution concentration (w/w %) | low | 46-48 | 47 |
| 47% NaOH aqueous solution (vol) | medium | 0.62-0.63 | 0.63 |
| Reaction temperature (° C.) | medium | 15 to 20 | 18 | w/w % = percentage by equivalent weight ratio (i.e., kg agent per kg Int E × 100)

In some embodiments, the process parameters for the isolation of compound Int E are as listed in Table 12.

TABLE 12

Process parameters for the isolation of Int E

| Process Parameter | Impact Assessment (high, medium low) | Normal Operating Range | Target |
|---|---|---|---|
| Aqueous HCl concentration (N) | low | 2.9-3.1 | 3 |
| Batch pH adjustment with 3N HCl | low | 6-7 | 6.5 |
| Batch volume after concentration (vol) | medium | 5.0-6.0 | 5.5 |
| MTBE (vol) | low | 2.69-2.72 | 2.7 |

Table 13 describes certain analytical data measured during the preparation of compound Int E from compound Int D according to the synthetic scheme detailed in Scheme 2 above.

TABLE 13

List of in-process controls for Int E

| Analytical Test | Analytical Method | Target Results | Typical Result |
|---|---|---|---|
| Consumption of Int D | HPLC | ≤1.0% | 0.6% |
| Assay of Int E2 | HPLC | Report | 57.3% |
| Consumption of Int E2 | HPLC | ≤1.0% | 0.2% |
| Residual Int E in supernatant | HPLC | ≤1.0% | 0.3% |
| Residual water content in Int E | KF | ≤0.8% | 0.3% |
| Assay of Int E | HPLC | ≥80% | 91.2% |

Step 4: Preparation of Compound (I) (TATD)

Compound (I) (TATD) has the following structural formula:

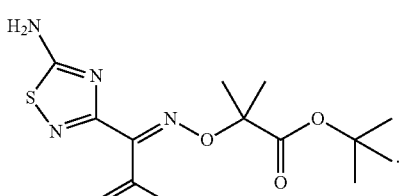

(I)

In some embodiments, the process parameters for the preparation of compound (I) are as listed in Table 14A.

TABLE 14A

Exemplary process parameters for the preparation of compound (I) (TATD)

| Process Parameter | Impact Assessment (high, medium, low) | Normal Operating Range | Target |
|---|---|---|---|
| MeOH (vol) | medium | 11.4-11.9 | 11.4 |
| Et$_3$N (equiv) | medium | 4.00-4.06 | 4.0 |
| Br$_2$ (equiv) | medium | 1.35-1.42 | 1.35 |
| KSCN (equiv) | medium | 1.33-1.42 | 1.35 |
| Reaction temperature (° C.) | medium | −10 to 0 | −5 |

In some embodiments, the process parameters for the preparation of compound (I) are as listed in Table 14B.

TABLE 14B

Exemplary process parameters for the preparation of compound (I) (TATD)

| Process Parameter | PAR | NOR | Target |
|---|---|---|---|
| MeOH (vol) | 9.0 to 15.0 | 9.9 to 10.4 | 10.1 |
| triethylamine (equiv) | 3.50 to 4.50 | 3.9 to 4.1 | 4.0 |
| Br$_2$ (equiv) | 1.30 to 1.48 | 1.36 to 1.42 | 1.39 |
| KSCN (equiv) | 1.20 to 1.50 | 1.30 to 1.40 | 1.35 |
| Reaction temperature (° C.) | −25 to 15 | −10 to 0 | −5 |

PAR = proven acceptable range;
NOR = normal operating range

In some embodiments, the process parameters for the isolation of compound (I) are as listed in Table 15A.

TABLE 15A

Exemplary process parameters for the isolation of compound (I) (TATD)

| Process Parameter | Impact Assessment (high, medium, low) | Normal Operating Range | Target |
|---|---|---|---|
| Activated carbon (w/w %) | low | 0.09-0.11 | 0.1 |
| Carbon treatment temperature (° C.) | low | 30 to 40 | 35 |
| Diatomite (w/w %) | low | 0.09-0.11 | 0.1 |
| Batch volume after 1$^{st}$ concentration (vol) | medium | 5-7 | 6 |
| Aqueous HCl concentration (N) | low | 0.9-1.1 | 1 |
| Batch pH adjustment with 1N HCl | low | 2-3 | 2.5 |
| THF (vol) | medium | 9.8-10 | 9.9 |
| H$_2$O (vol) | medium | 0.4-0.6 | 0.5 |
| Active carbon (w/w %) | medium | 0.045-0.054 | 0.045 |
| Carbon treatment temperature (° C.) | low | 50 to 60 | 55 |
| Batch volume after 2$^{nd}$ concentration (vol) | medium | 2.24-4.49 | 3.37 |
| MTBE (vol) | medium | 3.78-4.05 | 3.87 |
| MeOH (vol) | medium | 4.05-4.18 | 4.14 |
| H$_2$O | medium | 3.9-4.1 | 4.1 |
| MeOH/H$_2$O slurry temperature (° C.) | medium | 50 to 60 | 55 | w/w % = percentage by equivalent weight ratio (i.e., kg agent per kg compound (I) × 100)

In some embodiments, the process parameters for the isolation of compound (I) are as listed in Table 15B.

TABLE 15B

Exemplary process parameters for the isolation of compound (I) (TATD)

| Process Parameter | PAR | NOR | Target |
|---|---|---|---|
| Batch volume after 1$^{st}$ concentration (vol) | 4 to 8 | 4.2 to 6.0 | 5.0 |
| Batch pH | 1.5 to 3.5 | 1.6 to 2.5 | 2.2 |
| Batch volume after 2$^{nd}$ concentration (vol) | 1.5 to 3.5 | 1.8 to 2.8 | 2.2 |
| MTBE charge (vol) | 3.0 to 5.2 | 3.2 to 4.8 | 4.2 |
| THF during carbon treatment (vol)* | 9.0 to 11.0 | 9.8 to 10.0 | 9.9 |
| Water during carbon treatment (vol)* | 0.40 to 0.60 | 0.45 to 0.55 | 0.50 |
| Temperature during carbon treatment (° C.)* | ≤45 for up to 72 h or ≤70 for up to 24 h | 40 to 50 | 45 |
| MeOH (vol)* | 3.0 to 4.5 | 3.4 to 3.6 | 3.5 |
| Water (vol)* | 3.0 to 4.5 | 3.4 to 3.6 | 3.5 |
| Temperature for MeOH/water slurry (° C.)* | 35 to 70 | 50 to 60 | 55 |
| Drying temperature (° C.)* | <70 | 50 to 60 | 55 |

*Parameters assessed by linear experiments
PAR = proven acceptable range;
NOR = normal operating range

TABLE 16

List of in-process controls for compound (I) (TATD)

| Analytical Test | Analytical Method | Target Results | Typical Result |
|---|---|---|---|
| Consumption of Int E | HPLC | ≤2.0% | 2.0% |
| Residual compound (I) (TATD) in supernatant | HPLC | ≤0.5%/≤1.5% | 0.5%/0.7% |
| Recycled THF quality | GC, KF and Titration | MeOH % = Report MTBE % = Report KF = Report Peroxide ≤ 50 ppm | MeOH % = 0.5% MTBE % = 0.02% KF = 3.6% Peroxide = 33 ppm |
| Purity of compound (I) (TATD) in wet cake | HPLC | ≥99%, single unspecified impurity ≤ 0.2% | 100% |
| Assay of compound (I) | HPLC | ≥99%, single unspecified impurity ≤ 0.2% | 100% |
| Residual solvent | GC | KF ≤ 0.5% THF % = Report MeOH % = Report MTBE % = Repor | KF = 0.3% THF % = 491 ppm MeOH % = 36 ppm MTBE % = 18 ppm |

Provided herein is the compound Int C. Also provided is a method of making compound Int C comprising the step of converting compound Int B into compound Int C. In one embodiment, the step of converting compound Int B into compound Int C comprises contacting, e.g., admixing or combining, Int B with NH$_3$. In another embodiment, it comprises the step of contacting, e.g., admixing or combining, Int B with NH$_3$, H$_2$O and CH$_3$OH.

In one embodiment, compound Int B is produced by a method comprising the steps of: (a) converting compound SM 1 into compound Int A, and (b) converting compound Int A into compound Int B.

In another embodiment, compound Int C is converted into compound (I) by a method comprising the steps of: (a) converting compound Int C into compound Int D, (b) converting compound Int D into compound Int E1, (c) converting compound Int E1 into compound Int E2, (d) converting compound Int E2 into compound Int E, and (e) converting compound Int E into compound (I).

In another aspect, provided herein is a method of making compound (I) comprising the steps of: (a) converting compound Int E2 into compound Int E, and (b) converting compound Int E into compound (I). In a particular embodiment, step (a) comprises the steps of: (1) combining compound Int E2 with a solution comprising an hydroxide salt; (2) agitating the combination of step (1); (3) addition of acid; and (d) obtaining compound Int E. In another particular embodiment, step (b) comprises the steps of: (1) forming a mixture comprising methanol and compound Int E; (2) adding triethylamine; (3) adding bromine; (4) adding a thiocyanate salt; (5) adjusting the pH of the reaction mixture to 2.5 with an aqueous solution of hydrochloric acid; and (6) obtaining compound (I).

In another embodiment, compound Int E2 is produced by a method comprising the steps of (a) converting compound Int D into compound Int E1, and (b) converting compound Int E1 into compound Int E2. In a particular embodiment, step (a) comprises converting compound Int D into compound Int E1 at a temperature between about 0° C. and 18° C., and step (b) comprises converting compound Int E1 into compound Int E2 at a temperature between about 15° C. and 18° C. In another particular embodiment, step (a) comprises the step of forming a reaction mixture comprising methanol, sodium methoxide, and compound Int D, thereby forming compound Int E1. In another particular embodiment, step (b) comprises the step of adjusting the pH of the reaction mixture to 6.5 with acetic acid and admixing, e.g., adding, ammonium chloride, thereby converting compound Int E1 into compound Int E2.

In another embodiment, compound Int D is produced by a method comprising the steps of (a) converting compound Int B into compound Int C, and (b) converting compound Int C into compound Int D. In a particular embodiment, step (a) comprises the steps of: (1) contacting, e.g., combining, compound Int B with ammonia, water and methanol; (2) adjusting the pH of the reaction mixture to a pH of about 5 with hydrochloric acid; and (3) obtaining compound Int C. In another particular embodiment, step (b) comprises the steps of: (1) forming a reaction mixture comprising methyl tert-butyl ether, phosphorus pentachloride and pyridine; (2) combining compound Int C with the reaction mixture of step (1); (3) adding an aqueous solution of methanol; and (4) obtaining compound Int D.

In another embodiment, compound Int B is produced by a method comprising the steps of: (a) converting compound SM 1 into compound Int A, and (b) converting compound Int A into compound Int B. In a particular embodiment, step (a) comprises the steps of: (1) forming a reaction mixture comprising water, sodium nitrite, acetic acid and compound SM 1; (2) adjusting the pH of the reaction mixture to about 6.5 with acetic acid; and (3) obtaining compound Int A. In another particular embodiment, step (b) comprises the steps of: (1) combining compound Int A with compound SM 2, triethylamine and dimethylformamide; and (2) obtaining compound Int B.

6.4. Crystalline Form of Compound (I)

Provided herein is a crystal form of compound (I) characterized by an X-ray powder diffraction (XRPD) pattern having peaks at angles (2 theta ±0.2) of 7.5, 7.9, 11.5, 15.7, 17.3, and 23.2. In one embodiment, the crystal form of compound (I) is characterized by an X-ray powder diffraction (XRPD) pattern having further peaks at angles (2 theta ±0.2) of 14.1, 14.7, 16.2, 19.9, 20.7, 23.5, and 29.9.

In another embodiment, the crystal form of compound (I) is characterized by an X-ray powder diffraction (XRPD) pattern having peaks at angles (2 theta ±0.2) of 7.5, 7.9, 10.2, 11.5, 15.7, 17.3, 23.2 and 29.9.

In another embodiment, the crystal form of compound (I) is characterized by an X-ray powder diffraction (XRPD) pattern having peaks at angles (2 theta ±0.2) of 7.5, 7.9, 10.2, 11.5, 14.1, 14.7, 15.1, 15.7, 16.2, 17.3, 17.8, 18.3, 18.9, 19.3, 19.9, 20.7, 21.3, 22.7, 23.2, 23.5, 23.9, 25.2, 25.7, 25.9, 26.3, 26.9, 28.7, 29.3, 29.9, 30.5, 31.3, 31.8, 32.2, 32.4, 33.2, 33.8, 34.8, 35.2, 36.6, 37.1, 38.1, 41.6, 42.1, 42.5, 43.2, 45.1, 46.5, 47.5, and 47.9.

In another embodiment, the crystal form of compound (I) is characterized by an X-ray powder diffraction (XRPD) pattern having one or more, two or more, three or more, four or more, or five or more peaks at angles (2 theta ±0.2) of 7.5, 7.9, 10.2, 11.5, 14.1, 14.7, 15.1, 15.7, 16.2, 17.3, 17.8, 18.3, 18.9, 19.3, 19.9, 20.7, 21.3, 22.7, 23.2, 23.5, 23.9, 25.2, 25.7, 25.9, 26.3, 26.9, 28.7, 29.3, 29.9, 30.5, 31.3, 31.8, 32.2, 32.4, 33.2, 33.8, 34.8, 35.2, 36.6, 37.1, 38.1, 41.6, 42.1, 42.5, 43.2, 45.1, 46.5, 47.5, and 47.9.

In another embodiment, the crystal form of compound (I) is characterized by an X-ray powder diffraction (XRPD) pattern having peaks at the angles (2 theta ±0.2) listed in the Table of FIG. 13.

In another embodiment, the crystal form of compound (I) is characterized by an X-ray powder diffraction (XRPD) pattern substantially corresponding to FIG. 12.

6.5. Synthetic Compositions

Compound (I) is a useful intermediate in the production of antibiotics, particularly ceftolozane, and salts thereof. Compositions comprising compound (I) and intermediates are provided herein. Also provided are compositions produced or occurring during the methods of making compound (I).

The following composition may be produced during the methods of the invention to prepare intermediate C (Int C): a composition comprising compounds SM 1 (dimethyl malonate) and Int A; a composition comprising Int A and Int B; a composition comprising Int B and Int C; a composition comprising SM 1, Int A and Int B; a composition comprising Int A, Int B and Int C; a composition comprising SM 1, Int A, Int B and Int C.

The following composition may be produced during the methods of the invention to prepare intermediate D (Int D): a composition comprising compounds Int C and Int D.

The following composition may be produced during the methods of the invention to prepare intermediate E (Int E): a composition comprising compounds Int D and Int E1; a composition comprising compounds Int E1 and Int E2; a composition comprising compounds Int E2 and Int E; a composition comprising compounds Int D, Int E1 and Int E2; a composition comprising compounds Int E1, Int E2 and Int E; and a composition comprising compounds Int D, Int E1, Int E2 and Int E.

The following composition may be produced during the methods of the invention to prepare compound (I) (TATD): a composition comprising compounds Int E and compound (I).

7. EXAMPLES

Example 1

Preparation of (Z)-2-(5-amino-1,2,4-thiadiazol-3-yl)-2-(((1-(tert-butoxy)-2-methyl-1-oxopropan-2-yl)oxy)imino)acetic acid (TATD)

7.1. Step 1: Preparation of Intermediate C (Int C)

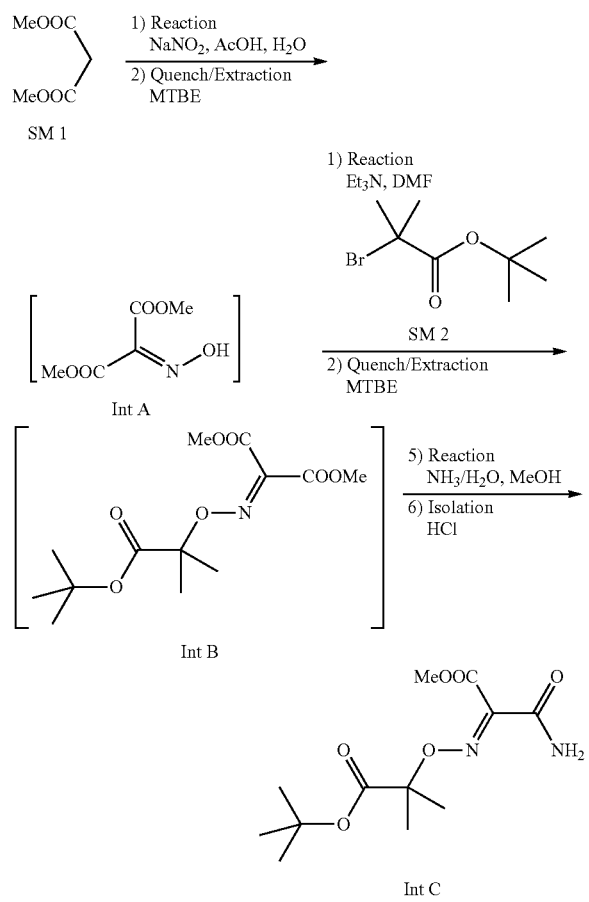

The process parameters for the preparation of compounds Int A, Int B and Int C are described in Tables 1-6 and the in-process controls for Int C are listed in Table 7.

7.1.1. Step 1-A: Preparation of Intermediate A (Int A)

Holding tank 1 was charged with $H_2O$ (300 kg, 1.50 vol) and $NaNO_2$ (161.3 kg, 1.54 equiv), and agitated for 30 minutes at a temperature between 20 and 25° C.

Reactor 1 was charged with acetic acid (202.3 kg, 2.22 equiv) and the temperature was adjusted to a range between 20 and 30° C. Then, reactor 1 was charged with SM 1 (200.6 kg, 1.00 eq) at a temperature between 20 and 30° C. The solution in holding tank 1 was transferred to reactor 1 at a temperature between 20 and 30° C. over the course of 2 to 3 hours. The contents of reactor 1 were agitated for 12 to 13 hours at a temperature between 20 and 30° C.

Reactor 1 was charged with a 25% NaCl solution (214 kg, 0.89 vol), followed by methyl tert-butyl ether (MTBE) (447.6 kg, 3.02 vol), and the batch was agitated for 30 minutes at a temperature between 20 and 30° C. The agitation was stopped, and the batch was allowed to stand for 30 minutes until the phases separated. The lower aqueous phase was transferred to holding tank 1. The upper organic layer was transferred to holding tank 2. The lower aqueous phase in holding tank 1 was transferred back to reactor 1, and reactor 1 was charged with MTBE (452.0 g, 3.05 vol). The contents of reactor 1 were agitated for 60 minutes at a temperature between 20 and 30° C. The agitation was stopped, and the batch was allowed to stand for 30 minutes until the phases separated. The lower aqueous phase was transferred to holding tank 1. The upper organic layer in holding tank 2 was transferred to reactor 1. Then, reactor 1 was charged with $H_2O$ (445 kg, 2.23 vol), and the batch is agitated at a temperature between 20 and 30° C.

Subsequently, reactor 1 was charged with $NaHCO_3$ (105.4 kg, 0.83 eq) to adjust pH to 6.9, and the batch was agitated for 30 minutes at a temperature between 20 and 30° C. The agitation was stopped, and the batch was allowed to stand for 30 minutes until the phases separated. The lower aqueous phase was transferred to holding tank 2. A portion of the 25% NaCl solution (205.0 kg, 0.85 vol) was charged to reactor 1, and the batch was agitated for 30 minutes at a temperature between 20 and 30° C. The agitation was stopped, and the batch was allowed to stand for 30 minutes until the phases separated. The lower aqueous phase was transferred to holding tank 2. The batch in reactor 1 was concentrated under reduced pressure at a temperature below 40° C. to a volume of 200 to 300 L (1.35-2.03 vol). Int A was used in the preparation of intermediate 13 (Int B) without further work-up or purification. See HPLC trace of Int A in FIG. 3.

7.1.2. Step 1-B: Preparation of Intermediate B (Int B)

The temperature of the batch in reactor 1 was adjusted to below 30° C. Reactor 1 was charged with DMF (868.0 kg, 4.62 vol), while maintaining the batch temperature below 30° C. The contents of reactor 1 were agitated for 30 minutes at a temperature between 20 and 30° C.

Reactor 1 was charged with $NEt_3$ (295.2 kg, 1.92 eq), followed by SM 2 (350.0 g, 1.03 eq) at a temperature between 20 and 30° C. Then the batch was adjusted to a temperature between 45 and 50° C. and agitated for 20 to 25 hours, while maintaining this temperature.

Subsequently, the batch was adjusted to a temperature between 20 and 30° C. Reactor 1 was charged with MTBE (606.2 kg, 4.09 vol), and the temperature was adjusted and maintained at a range between 0 and 10° C. Subsequently, $H_2O$ (460.0 kg, 2.30 vol) was charged to the batch, followed by 2N HCl (652 kg, 2.96 vol) to adjust the pH to 6. The batch was agitated for 30 minutes. Then the agitation was stopped, and the batch was allowed to stand for 30 minutes until the phases separated. The lower aqueous layer was transferred to holding tank 1. The upper organic layer was transferred to holding tank 2. The aqueous layer in holding tank 1 was transferred to reactor 1. Reactor 1 was charged with MTBE (308.2 kg. 2.08 vol), and the batch was agitated for 30 minutes. Then the agitation was stopped and the batch was allowed to stand for 30 minutes until the phases separated. The lower aqueous layer was transferred to holding tank 1. The organic layer in holding tank 2 was transferred to reactor 1. Then, reactor 1 was charged with a 25% NaCl (466.0 g, 1.94 vol) solution. The contents of reactor 1 were agitated for 30 minutes. Then the agitation was stopped, and the batch was allowed to stand for 30 minutes until the phases separated. The lower aqueous layer was transferred to holding tank 1. Reactor 1 was charged with a 25% NaCl (449.0 kg, 1.87 vol) solution. The contents of reactor 1 were agitated for 30 minutes. Then the agitation was stopped, and the batch was allowed to stand for 60 minutes until the phases separated. The batch was concentrated under reduced pressure to a volume between 440 and 500 L (2.0-2.3 vol), while maintaining the batch temperature below 40° C. The batch comprising Int B was used in the preparation of intermediate C (Int C) without further work-up or purification. See HPLC trace of Int B in FIG. 4.

7.1.3. Step 1-C: Preparation of Intermediate C (Int C)

In one preferred process, compound Int C can be prepared with unexpectedly high selectivity by selection of the reaction temperature (e.g., at or below about 0° C.) and using conditions comprising ammonium hydroxide (e.g., as disclosed herein).

After concentration, the batch comprising Int B was transferred to reactor 3. Then reactor 3 was charged with methanol (MeOH, 411.0 kg, 2.60 vol), and the batch was adjusted to a temperature between −5 and −2° C. A 25% (w/w %) $NH_3/H_2O$ (185.8 kg, 1.02 vol) solution was charged to reactor 3, while maintaining the batch at a temperature between −5 and 5° C. The batch was agitated for 3 to 6 hours at a temperature between −5 and 5° C., then the batch was adjust to a temperature between −10 and 0° C.

Pre-cooled water (790 kg, 3.95 vol) at 0 to 5° C. was transferred to reactor 3, while maintaining the batch temperature at −10 to 5° C. Pre-cooled 2N HCl (771 kg, 3.50 vol) at 0 to 5° C. was transferred to reactor 3 to achieve a pH of 5, while maintaining the batch temperature between −10 and 5° C. The batch was concentrated (1800 to 2200 L, 9.00-11.00 vol) under reduced pressure, while maintaining the batch temperature below 40° C. The batch was agitated for 1 to 2 hours at a temperature between 15 and 25° C. The batch was filtered to afford the product as a wet cake, and the wet cake was washed with $H_2O$ (42 kg, 0.21 vol) followed by a 1:4 (w/w) solution of MeOH and $H_2O$ (68 kg, 0.36 vol). The solid was dried under reduced pressure for 40 to 70 hours at a temperature between 60 and 65° C. Then the solid was further dried under vacuum for 10 to 15 hours at a temperature between 60 and 65° C. Int C was isolated as an off-white to white solid. Yield=301.15 kg (68.8%). See HPLC trace in FIG. 5 and $^1$H-NMR spectrum in FIG. 9. The $^1$H-NMR spectrum was obtained using a 400 MHz instrument and $CDCl_3$.

7.2. Step 2: Preparation of Intermediate D (Int D)

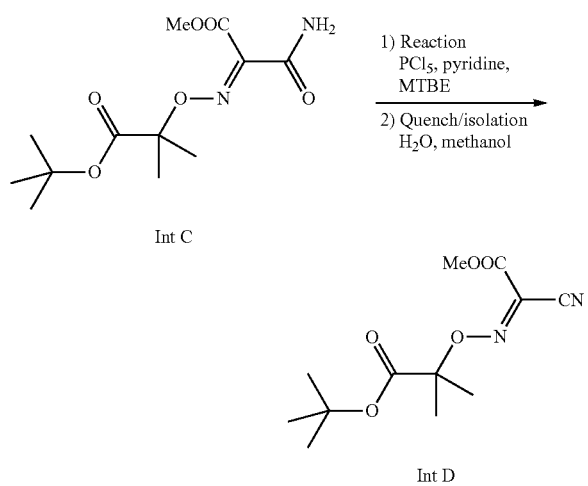

Reactor 1 was charged with MTBE (600.0 kg, 2.70 vol) and the temperature was adjusted to a range between −10 and 0° C. Then reactor 1 was charged with $PCl_5$ (264.7 kg, 1.22 eq). Subsequently, pyridine (600.3 kg, 7.28 eq) was added to reactor 1, while maintaining the batch temperature below 30° C. The batch was agitated for 30 minutes at a temperature between −10 and 20° C. Then, reactor 1 was charged with Int C (300.4 kg, 1.00 eq) via portion-wise addition, while maintaining the batch temperature below 20° C. The contents of reactor 1 were agitated for 10 to 18 hours at a temperature between 15 and 20° C.

Reactor 2 was charged with $H_2O$ (930 kg, 3.10 vol), and the temperature was adjusted to a range between 0 and 3° C. The contents of reactor 1 were transferred to reactor 2, while maintaining the temperature of reactor 2 below 20° C. The contents of reactor 2 were agitated for 60 to 90 minutes at a temperature between 10 and 20° C., or until the pH value was 3. The agitation was stopped, and the batch was allowed to stand for 2 to 3 hours until the phases separated. The lower aqueous layer was transferred to holding tank 1. Reactor 2 was charged with a 25% NaCl (600 kg, 1.67 vol) solution, followed by MeOH (71 kg, 0.30 vol), and the batch was adjusted to a temperature between 20 and 30° C. The batch was agitated for 30 minutes. Then the agitation was stopped, and the batch was allowed to stand for 45 to 60 minutes until the phases separated. The lower aqueous layer was transferred to holding tank 1. Reactor 2 was charged with a 25% NaCl (572 kg, 1.59 vol) solution, followed by MeOH (36 kg, 0.15 vol), and the batch was adjusted to a temperature between 20 and 30° C. The batch was agitated for 30 minutes. Then the agitation was stopped, and the batch was allowed to stand for 45 to 60 minutes until the phases separated. The lower aqueous layer was transferred to holding tank 1. The batch (in reactor 2) was charged with active carbon (60 kg). The contents of reactor 2 were adjusted to a temperature between 50 to 55° C. and then were agitated for 30 to 60 minutes at this temperature. The batch temperature is adjusted to 20 to 30° C. then filtered through a pad of diatomite into reactor 3. The batch in reactor 3 was concentrated under reduced pressure to 301 to 452 L (1.0-1.5 vol) while maintaining the temperature below 40° C. Reactor 3 was charged with MeOH (290.0 kg, 1.22 vol). The batch was concentrated under reduced pressure to 301-452 L, 1.0-1.5 vol), while maintaining the batch temperature below 40° C. The water content was deemed acceptable when ≤0.2% water remained by Karl Fischer (KF) titration (method: TWI-QC-020.01). MeOH (150.6-301.2 kg, 0.63-1.25 vol) was charged to reactor 3, and the batch was concentrated under reduced pressure to 301-452 L (1.0-1.5 vol), while maintaining the batch temperature below 40° C. Int D was isolated as a brown oil. Yield: 268.7 kg (95.4%). See HPLC trace in FIG. 6 and $^1$H-NMR spectrum in FIG. 10. The $^1$H-NMR spectrum was obtained using a 400 MHz instrument and $CDCl_3$.

7.3. Step 3: Preparation of Intermediate E (Int E)

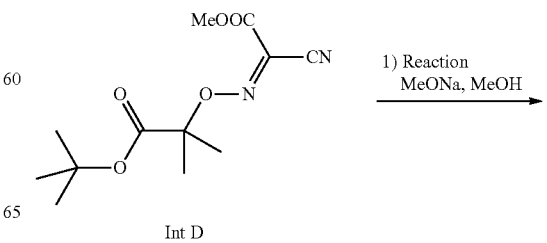

The process parameters for the preparation of Int D are described in Tables 8-9 and the in-process controls for Int D are listed in Table 10.

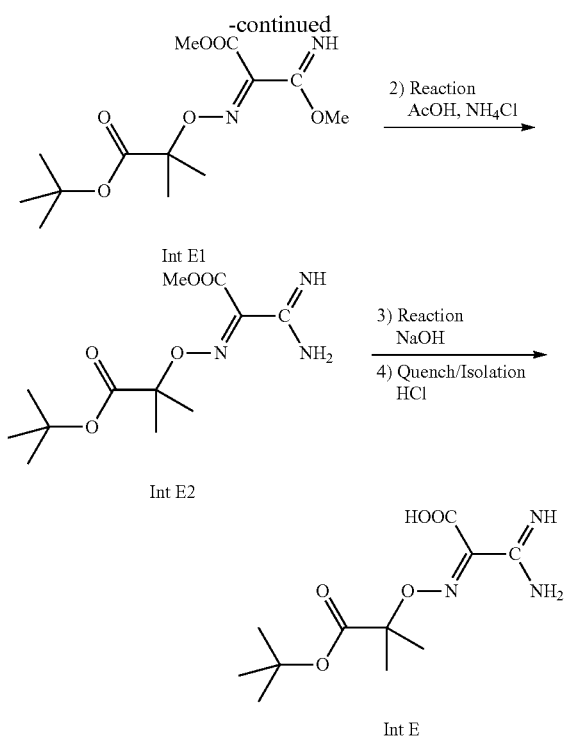

Int E1

Int E2

Int E

In a preferred process, the temperature of reaction step 1) above is maintained at a temperature effective to increase the yield of the Int E compound from Int D (including desirably high rates of conversion of Int D to Int E1). The compounds Int E1 and Int E2 can be formed in situ, and Int E is isolated from the reaction mixture at the conclusion of the process described as Step 3 above. While MeONa is used in the conversion of Int D to Int E1 in the reaction scheme above, other embodiments include the use of any suitable alcohol (e.g., ethanol, isopropanol) or suitable salts thereof (e.g., sodium salts) in place of or in addition to the MeONa reagent. The suitable alcohol can be used with any suitable leaving group (e.g., HCl). The temperature of the reaction of Int D is preferably selected to maximize the yield of Int E, including temperatures that maximize the yield for the conversion of Int D to Int E1. The temperature for the reaction of Int D is preferably 17 degrees C. or lower (e.g., 0 degrees C., or lower), although the reaction(s) can be performed at other temperatures (e.g., 0-18° C.).

The process parameters for the preparation of Int E are described in Tables 11-12 and the in-process controls for Int E are listed in Table 13.

MeOH (940.0 kg, 4.84 vol) was charged to reactor 1 followed by Int D (261.7 kg, 1.00 eq), and the batch was agitated. The batch was adjusted to a temperature between 0 and 5° C. A solution of 27% MeONa in MeOH (43.6 kg, 0.23 eq) was charged to reactor 1 at a temperature between 0 and 18° C. The batch was adjusted to a temperature between 15 and 18° C. and then was agitated for 1 to 2 hours.

AcOH (15.4 kg, 0.26 eq) was charged to the batch to adjust the pH to 6.5, while maintaining the batch at a temperature between 15 and 18° C. NH$_4$Cl (56.4 kg, 1.09 eq) was charged to the batch. The batch was agitated for 20 to 22 hours at a temperature between 15 and 18° C.

Preferably, processes include the saponification of Int E substrate (i.e., Int E2). The order of reaction can affect the yield of the product. For example, reactor 1 was charged with a 47% NaOH (245.0 kg, 0.63 vol) solution slowly, while maintaining the batch at a temperature between 0 and 20° C. Then the batch was adjusted to a temperature between 15 and 20° C., and agitated for 2 to 4 hours at this temperature. The batch was adjusted to a temperature between 5 and 10° C. Then reactor 1 was charged with 3N HCl (675.0 kg, 2.58 vol) via dropwise addition to adjust pH to 7, while maintaining the batch temperature between 5 and 20° C. The batch was concentrated under reduced pressure to a volume between 1309 and 1570 L (5.0-6.0 vol), while maintaining the batch temperature below 40° C. The batch was gradually adjusted to a temperature between 20 and 25° C. over the course of 1 to 2 hours. Then the batch was agitated at this temperature for 15 to 30 minutes. The product was filtered, and the resulting wet cake was transferred to reactor 1. Then reactor 1 was charged with MTBE (522.6 kg, 2.7 vol). The batch was agitated for 0.5 to 1 hour at a temperature between 0 and 5° C. The product was filtered, and the wet cake was dried under reduced pressure over the course of 40 to 60 hours, while maintaining the jacket temperature below 63° C. Int E was isolated as a light yellow solid. Yield: 129.95 kg, (44.8%). See HPLC trace in FIG. 7 and $^1$H-NMR spectrum in FIG. 11. The $^1$H-NMR spectrum was obtained using a 400 MHz instrument and CDCl$_3$.

TABLE 17

Screening of reaction temperature for E1

| Experiment | | 1 hour | 5 hours | 25 hours |
|---|---|---|---|---|
| 20.0 g scale, 0° C. | Solution assay (E1) | 13.1 | 12.7 | 13.3 |
| | Solution yield (%) | 80.9 | 78.5 | 82.2 |
| 20.0 g scale, 17° C. | Solution assay (E1) | 12.3 | 10.3 | 4.5 |
| | Solution yield (%) | 75.9 | 63.6 | 27.8 |
| 20.0 g scale, 30° C. | Solution assay (E1) | 9.7 | 6.0 | 2.7 |
| | Solution yield (%) | 59.9 | 37.1 | 16.8 |

Referring to Table 17, the solution yield was unexpectedly high at room temperature, although lower reaction temperatures can increase stability and yields. The intermediate E1 was found to be unstable at elevated reaction temperatures, as can be seen in Table 17 above. The solution yield and solution assay are constant for up to 25 hours at 0° C. However if the reaction is performed at 17° C. the solution yield drops from the 1 hour time point of 75.9% to 63.6% at 5 hours. If the reaction is maintained at 30° C., the solution yield decreases from 59.9% to 37.1% over the same time period. From this data the reaction should be performed below 10° C., preferably below 0° C., although other embodiments include temperatures at or below about 17° C.

7.4 Step 4. Preparation of Compound (I) (TATD)

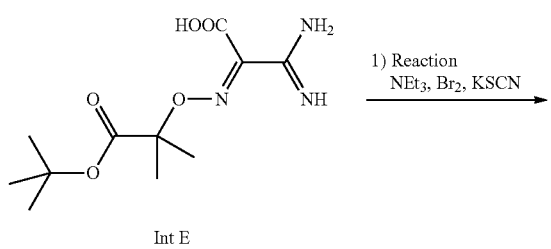

Int E

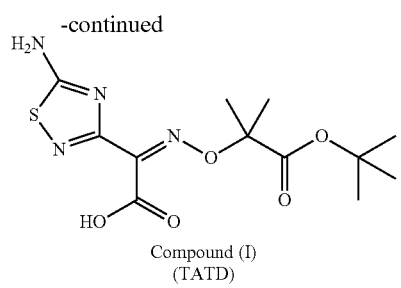

Compound (I)
(TATD)

The process parameters for the preparation of compound (I) (TATD) are described in Tables 14-15 and the in-process controls for compound (I) (TATD) are listed in Table 16.

MeOH (1042 kg, 11.4 vol) was charged to reactor 1 followed by Int E (110.4 kg, 1.0 eq). The batch in reactor 1 was charged with $NEt_3$ (165.0 kg, 4.0 eq). Then the batch was adjusted to a temperature between −10 and 0° C., and this temperature was maintained until the reaction was deemed complete. The batch was charged with $Br_2$ (bromine, 90.9 kg, 1.41 eq) via dropwise addition, and then the batch was agitated for 10 to 20 minutes. MeOH (350.0 kg, 3.8 vol) was charged to reactor 2 followed by portionwise addition of potassium thiocyanate (KSCN, 54.5 kg, 1.39 eq). The contents of reactor 2 were agitated for 30 minutes. The KSCN methanolic solution in reactor 2 was transferred to reactor 1. Subsequently the batch in reactor 1 was agitated for 1 to 2 hours.

Activated charcoal (10.6 kg) was charged to reactor 1 and the temperature was adjusted to a value between 30 and 40° C. Then the batch was agitated the aforementioned temperature for 30 to 60 minutes. The batch in reactor 1 was charged with diatomite (12.8 kg). Then the batch was centrifuged and the filtrate was transferred to reactor 1. The batch was concentrated under reduced pressure to a volume between 555 to 777 L (5-7 vol), while maintaining the temperature below 40° C. The batch was adjusted to a temperature between 10 and 20° C. 1 N HCl (464 kg, 4.2 vol) was charged to reactor 1 to adjust pH to 2.5. The batch was agitated for 30 to 60 minutes at a temperature between 10 and 20° C.

The batch was centrifuged to afford the product as a wet cake, and then the wet cake was transferred to reactor 1. Reactor 1 was charged with THF (972.0 kg, 9.9 vol) followed by $H_2O$ (44.6 kg, 0.4 vol). The batch temperature was adjusted to a temperature between 50 and 60° C. and then agitated for 30 to 60 minutes at a temperature between 50 and 60° C. The batch was adjusted to a temperature between 40 and 50° C. and then was charged with activated charcoal (5.0 kg). The batch was adjusted to a temperature between 50 and 60° C., and then the batch was agitated for 30 to 60 minutes at this temperature. The batch was filtered, and the filtrate was transferred to reactor 2. The contents of reactor 2 were concentrated to a volume between 222 and 444 L (2-4 vol), while maintaining the temperature below 40° C. The batch was adjusted to a temperature between 50 and 60° C., and then reactor 2 was charged with MTBE (318.0 kg, 3.87 vol) via dropwise addition. The batch was cooled to a temperature between 0 and 5° C., and the batch was agitated for 1 to 2 hours.

The batch was centrifuged to afford the product as a wet cake, and the wet cake transferred to reactor 2. MeOH (360.0 kg, 4.14 vol) was charged to reactor 2 followed by $H_2O$ (450.0 kg, 4.09 vol). The batch was adjusted to a temperature between 50 and 60° C., and the batch was agitated for 3 to 4 hours at this temperature. Subsequently, the batch was adjusted to a temperature between 20 and 30° C. and agitated for 30 to 60 minutes. The batch was centrifuged.

The batch was dried under reduced pressure for 18 to 20 hours with a jacket temperature below 60° C. TATD was isolated. Yield: 106.5 kg (79.8%). See HPLC trace in FIG. 8.

$^1$H NMR data: δ 13.77 ppm (s, 1H, COOH), 8.23 ppm (s, 2H, NH2), 1.43 ppm (s, 6H, $C(CH_3)_2$), 1.38 ppm (s, 9H, $C(CH_3)_3$).

Compound Int E can be converted to TATD according to the reaction scheme above. The resulting TATD in solution can be precipitated by addition of a strong acid (e.g., HCl). Adding an alcohol and water (e.g., MeOH and water) can result in formation of crystalline TATD from the solution. The amount of water is selected to maintain solubility temperature less than the degradation of TATD. The speed of cooling can affect the particle size of the solid TATD, with faster cooling resulting in smaller particles.

The comparison of Method A2 as described above in the Steps of the present Example to another embodiment (Method A1) is shown in Tables 18 and 19.

TABLE 28

Summary of differences between two methods to make compound (I) from compound Int C

| Step | Method A1 | Method A2 | Method A2 compared to Method A1 |
| --- | --- | --- | --- |
| Int C to Int D | Reaction washed twice with aqueous sodium chloride | Both aqueous sodium chloride washes replaced by a single water wash | Removes an operation and reduces waste and cycle time |
| Int D to Int E1 | Reaction temperature 15° C. to 18° C., sodium methoxide | Reaction temperature −20° C. to 0° C., sodium methoxide | Lower reaction temperature reduces by-product formation |
| Int E2 to Int E | Reaction temperature 15° C. to 18° C., sodium hydroxide | Reaction temperature 5° C. to 15° C., sodium hydroxide | Lower reaction temperature reduces by-product formation |
| Int E2 to Int E | Isolation; the batch was slurried in MTBE to remove impurities and water | Isolation; the batch was washed with methanol to remove impurities and water | Methanol removes impurities and water, washing the batch reduces cycle time compared to slurry method |

TABLE 28-continued

Summary of differences between two methods to make compound (I) from compound Int C

| Step | Method A1 | Method A2 | Method A2 compared to Method A1 |
|---|---|---|---|
| Int E to (I) | Reagent: NH$_4$SCN | Reagent: KSCN | Shorter reaction time, reduced amount of bromine using potassium salt |
| Int E to (I) | Charcoal treatment by batch mode (charged to reactor) | Charcoal treatment by carbon cartridge (batch flow through filter containing carbon) | Reduce reactor cleaning time, easier operation |

Table 18 details some of the key differences between Method A1 and Method A2 at multikilogram scale. In some cases, for example, in the reaction of Int C to Int D, Method A2 reduces the number of operations and the amount of waste material generated by the process. In other cases, such as the reaction of Int D to Int E1, the protocol change from Method A1 to Method A2 results in a lower amount of by-products. In yet other cases, such as in the reaction of Int E to compound (I), the modification in Method A2 as compared to the corresponding procedure in Method A1 leads to shorter reaction time or reactor cleaning time, thus reducing overall cycle time and overall cost.

TABLE 19

Summary of two methods at multikilogram scale

| | Method A1 | | | Method A2 | | |
|---|---|---|---|---|---|---|
| Step | Average Molar Yield (%) | Cycle Time (days) | Waste Generated (kg/kg) | Average Molar Yield (%) | Cycle Time (days) | Waste Generated (kg/kg) |
| Int C to Int D | 92 | 8 | 45 | 90 | 6 | 24 |
| Int D to Int E (combined) | 43 | 14 | 38 | 59 | 10 | 20 |
| Int E to (I) | 78 | 18 | 60 | 86 | 16 | 60 |
| Overall | 31 | 40 | 143 | 46 | 32 | 104 |

Table 19 details the average molar yield, cycle time, and waste generated (kg waste per kg product [kg/kg]) in a multikilogram synthesis of compound (I) from compound Int C using Method A1 or Method A2. Method A1 proceeds to desired compound (I) in 31% overall yield; a more preferred Method A2 proceeds in the higher overall yield of 46% overall. Some key characteristics of the Method A2 as compared with Method A1 include a higher yield of the conversion from compound Int D to Int E (59% vs. 43% in Method A1), and a higher yield of the conversion from compound Int E to compound (I) (86% vs. 78% in Method A1). Additionally, the waste generated in certain conversions is reduced in Method A2 as compared with the corresponding conversion in Method A1: (1) from Int C to Int D (24 kg/kg vs. 45 kg/kg in Method A1), and (2) from Int D to Int E (20 kg/kg vs. 38 kg/kg in Method A1). Also, incremental improvements in the cycle time for certain conversions in Method A2 compared with the corresponding conversion in Method A1 afford a significant reduction in overall cycle time for the process from compound Int C to compound (I) (32 days vs. 40 days in Method A1).

TABLE 20

Quality testing of batches of compound (I) from Method A1 and Method A2

| Method | Batch No. | water (%) | Assay (%) | Purity (%) | RRT: 0.32 | RRT: 0.93 | RRT: 1.24 | RRT: 1.28 |
|---|---|---|---|---|---|---|---|---|
| Method A1 | 1 | 0.01 | 100.0 | 99.9 | 0.03 | 0.03 | N.D. | N.D. |
| | 2 | 0.02 | 100.0 | 99.9 | 0.03 | 0.03 | 0.02 | 0.02 |
| | 3 | 0.03 | 100.1 | 99.9 | 0.03 | 0.03 | N.D. | 0.02 |

TABLE 20-continued

Quality testing of batches of compound (I) from Method A1 and Method A2

| Method | Batch No. | water (%) | Assay (%) | Purity (%) | RRT: 0.32 | RRT: 0.93 | RRT: 1.24 | RRT: 1.28 |
|---|---|---|---|---|---|---|---|---|
| | 4 | 0.03 | 100.2 | 99.9 | 0.03 | 0.03 | 0.02 | 0.02 |
| | 5 | 0.04 | 99.9 | 99.9 | 0.03 | 0.02 | N.D. | N.D. |
| | 6 | 0.02 | 100.0 | 99.9 | 0.04 | 0.03 | 0.02 | 0.02 |
| | 7 | 0.05 | 99.5 | 99.9 | 0.03 | 0.04 | 0.03 | 0.02 |
| | 8 | 0.03 | 98.8 | 100.0 | N.D. | 0.03 | 0.02 | N.D. |
| | 9 | 0.05 | 99.3 | 99.9 | 0.02 | 0.04 | 0.02 | N.D. |
| | 10 | 0.04 | 99.0 | 99.9 | 0.03 | 0.03 | 0.02 | N.D. |
| Method A2 | 11 | 0.1 | 99.1 | 99.0 | 0.03 | N.D. | 0.02 | 0.02 |
| | 12 | 0.1 | 100.0 | 100.0 | 0.03 | N.D. | N.D. | N.D. |
| | 13 | 0.1 | 99.5 | 100.0 | 0.03 | N.D. | N.D. | N.D. |

N.D. = not determined;
RRT = relative retention time of impurity (min) where compound (I) is at relative retention time 1.00 under HPLC conditions described in Example 7.

Table 20 demonstrates that both Method A1 and Method A2 affords high quality batches of compound (I) that meet desired specification criteria. All batches gave off-white to white solid. The water content (by Karl-Fischer (KF) analysis) (target ≤0.5%), assay (target ≥98.0%), purity (target ≥99.0%), and individual unspecified impurities (target ≤0.20% each) met target criteria in each case. No new impurities were detected in Method A2 compared to Method A1.

TABLE 21

Residual solvent analysis of compound (I) batches

| Method | Batch No. | Residual solvents | | | |
|---|---|---|---|---|---|
| | | THF (ppm) | Methanol (ppm) | MTBE (ppm) | Pyridine (ppm) |
| Method A1 | 7 | 734 | <300 | <500 | <200 |
| | 8 | 293 | <300 | <500 | <200 |
| | 9 | 488 | <300 | <500 | <200 |
| | 10 | 431 | <300 | <500 | <200 |
| Method A2 | 11 | 738 | <300 | <500 | <200 |
| | 12 | 249 | <300 | <500 | <200 |
| | 13 | 395 | <300 | <500 | <200 |

TABLE 22

Additional compound (I) batch analysis

| Method | Batch No. | Analytical Criteria | | | | | | |
|---|---|---|---|---|---|---|---|---|
| | | Heavy Metals (ppm) | Melting Point (° C.) | Residue on ignition (%) | Residual P (ppm) | Residual Br$^-$ (ppm) | Residual NO$_2^-$ (ppm) | Residual SCN$^-$ (ppm) |
| Method A1 | 7 | <20 | 186.2 | 0.1 | <10 | 764 | 30 | 101 |
| | 8 | <20 | 187.1 | 0.1 | <10 | 210 | <25 | 54 |
| | 9 | <20 | 185.0 | 0.1 | <10 | 473 | 47 | 88 |
| | 10 | <20 | 186.4 | 0.05 | 10 | 436 | 56 | 83 |
| Method A2 | 11 | <20 | 184.8 | 0.05 | 10 | 529 | 38 | 64 |
| | 12 | <20 | 185.6 | 0.02 | <10 | 132 | 33 | <40 |
| | 13 | <20 | 187.2 | 0.03 | <10 | 152 | 33 | <40 |

Tables 21 and 22 show further analyses of selected batches prepared by Method A1 and Method A2. In all batches tested, compound (I) showed residual solvent levels below target criteria (≤1500 ppm THF, ≤300 ppm methanol, ≤500 ppm MTBE, and ≤200 ppm pyridine) (Table 21). Additional batch analysis demonstrated that each batch also showed low residual levels of impurities such as heavy metals (≤20 ppm), salts (≤1000 ppm bromide, ≤100 ppm nitrite, and ≤150 ppm thiocyanate), and phosphorus (≤10 ppm) (Table 22). Moreover, each batch showed an acceptable residue on ignition (≤0.2%) and a melting point within the accepted range.

Example 2

In-process Controls (IPC) for Synthesis of Compound Int A (C11030405-A)

7.2.1. Method 1
1.1 Instrument
Karl Fischer Titrator
1.2 Type of titration solutions
HYDRANAL Composite 5
Methanol (HPLC Grade)
1.3 Analytical procedure
After pre-titration is stabilized, take approximately 0.2 g of solid sample or 1 mL of liquid sample to determine the water content. Two samples should be tested in parallel. Report the average value if both of test results meet principle of the method. (The amount of sample can be added or reduced according to the actual water content, but the reason must be recorded.)
1.4 Testing item: Water content (KF)
7.2.2. Method 2
2.1 Instrument
GC, equipped with FID detector
Electronic analytical balance
2.2 Reagent
Methanol (AR Grade)
2.3 Chromatographic Conditions

| | |
|---|---|
| Column: | DB-1 (30 m * 0.53 mm ID * 3 μm) |
| FID Temperature: | 270° C. |
| H$_2$: | 40 mL/min |
| Air: | 400 mL/min |
| Make up (N$_2$) Flow: | 30 mL/min |
| Temperature Program: | 50° C. (3 min) → 20° C./min → 120° C. (8 min) → 20° C./min → 250° C. (19 min) |

-continued

| | |
|---|---|
| Injector Temperature: | 250° C. |
| Split Ratio: | 50:1 |
| Carrier Gas: | N$_2$ |
| Control Mode: | Linear Velocity |
| Linear Velocity: | 30 cm/sec |
| Injection Volume: | 1.0 μL |
| Diluent: | Methanol |
| Needle Wash: | Methanol |

Note:

1. In order to elute strongly retained components from the GC column and ensure the reproducibility of continuous sample injections, the hold time at 250° C. can be extended according to the different characteristic of the sample.

2. In order to ensure proper recovery of the residual solvents in the sample, the Linear Velocity must be tightly controlled.

2.4 Reference Retention Times (MT-11-0501-01)

| Compound ID | C11030405-SM1 |
|---|---|
| Rt (min) | 10.5 |

2.5 (IPC)Testing Item: Residual SM 1
2.5.1 Preparation of solutions
2.5.1.1 Preparation of standard solution Accurately weigh approximately 100 mg C11030405-SM1 standard into a 100 mL volumetric flask, dissolve and dilute to volume with diluent, mix well.

2.5.1.2 Preparation of sample solution

For example: weigh approximately 1.0 g sample into a 10 mL volumetric flask, dissolve and dilute to volume with diluent, mix well.

2.5.2 Sample analysis

Set up instrument condition, after baseline is stabilized, the following injection procedure should be followed:

| Serial No. | Sample Name | No. of Injection |
| --- | --- | --- |
| 1 | Blank (sample diluent) | 1 or more |
| 2 | Standard solution | 1 |
| 3 | Sample solution | 1 |

2.5.3 Calculation

As per external standard method, calculate the residual compound C11030405-SM 1 as follows:

$$\text{Residual Compound } SM1(\%, w/w) = \frac{W_{STD} \times P_W}{V_{STD} \times A_{STD}} \times \frac{V_s \times A_s}{W_s} \times 100\%$$

$$\text{Or Residual Compound } SM1(g/L) = \frac{W_{STD} \times P_W}{V_{STD} \times A_{STD}} \times A_S \times K$$

Where: $W_{STD}$ represents the weight of C11030405-SM1 in standard solution (mg)
$W_S$ represents the weight of sample (mg)
$V_{STD}$ represents the dilution volume of C11030405-SM1 in standard solution (mL)
$V_S$ represents the dilution volume of sample (mL)
$A_S$ represents the peak area of C11030405-SM1 in sample solution
$A_{STD}$ represents the peak area of C11030405-SM 1 in standard solution
$P_W$ represents the assay value of C11030405-SM1 reference standard
K represents the dilution ratio 7.2.3. Method 3
3.1 Instrument
HPLC, equipped with PDA detector and auto-sampler
Electronic analytical balance
Pure water generator
3.2 Reagent
Acetonitrile (HPLC Grade)
3.3 Chromatographic Conditions

| Column: | Waters XTerra MS C18 (150 × 4.6 mm, 3.5 μm) |
| --- | --- |
| PDA Detector Wavelength: | 220 nm |
| Column Temperature: | 40° C. |
| Column Flow: | 1.0 mL/min |
| Injection Volume: | 10 μL |
| Acquisition Time: | 24 min |
| Run Time: | 24 min |
| Diluent: | Methanol |
| Needle Wash: | Methanol |

Mobile Phase A (0.05% TFA-H$_2$O): Accurately transfer 0.5 mL TFA into 1000 mL purified water and mix well. The solution should be filtrated and degassed before use.

Mobile Phase B (0.05% TFA-ACN): Accurately transfer 0.5 mL TFA into 1000 mL acetonitrile and mix well.

Gradient Program:

| Time (min) | A % | B % |
| --- | --- | --- |
| 0.0 | 95 | 5 |
| 15.0 | 5 | 95 |
| 18.0 | 5 | 95 |
| 18.01 | 95 | 5 |
| 24.0 | | stop |

NOTE: The chromatographic conditions were developed with Shimadzu LC-20A series HPLC. Some chromatographic conditions such as re-equilibrium time can be adjusted according to actual conditions.

3.4 Reference Retention Times (MT-11-0502-01)

| Compound ID | C11030405-A |
| --- | --- |
| RT (min) | 8.0 |
| RRT | 1.00 |

3.5 (IPC) Testing Item: Related substances and Assay of C11030405-A
3.5.1 Preparation of solutions
3.5.1.1 Preparation of standard solution Accurately weigh approximately 20 mg C11030405-A standard into a 100 mL volumetric flask, dissolve and dilute to volume with diluent, mix well.

3.5.1.3 Preparation of sample solution

For example: For solid: Accurately weigh approximately 20 mg sample into a 100 mL volumetric flask, dissolve and dilute to the volume with diluent, mix well. The weight of sample may be adjusted to reach equivalent intensity of C11030405-A in the sample as it is in the standard.

For liquid: Accurately transfer 1.0 mL sample into a 100 mL volumetric flask containing 20 mL of diluent, dissolve and dilute to the volume with diluent, mix well, accurately transfer this solution 1.0 mL into a 25 mL volumetric flask, dilute to volume with diluent, mix well. If the concentration is too high, dilute to appropriate concentration with diluent to reach equivalent intensity of C11030405-A in the sample as it is in the standard.

3.5.2 Sample analysis

Set up instrument condition, after baseline is stabilized, the following injection procedure should be followed:

| Serial No. | Sample Name | No. of Injection |
| --- | --- | --- |
| 1 | Blank (sample diluent) | 1 or more |
| 2 | Standard solution | 1 |
| 3 | Sample solution | 1 |

3.5.3 Calculation 3.5.3.1 Identification: The retention time range for identification of C11030405-A in the sample solution should be ±5.0% of the retention time of C11030405-A in standard solution.

3.5.3.2 Label the known impurities in the sample chromatogram refer to the standard chromatogram.

3.5.3.3 Do not integrate all the peaks with the retention time in the first 3 minutes, and only integrate the peaks ≥0.05% in sample chromatogram, then calculate the peak area percentage (HPLC Area %) of C11030405-A.

3.5.3.4 As per external standard method, calculate the assay (%, w/w) of sample as follows:

$$\text{Assay}(\%, w/w) = \frac{W_{STD} \times P_W}{V_{STD} \times A_{STD}} \times \frac{V_s \times A_s}{W_s} \times 100\%$$

$$\text{Or Assay}(g/L) = \frac{W_{STD} \times P_W}{V_{STD} \times A_{STD}} \times A_s \times K$$

Where: $W_{STD}$ represents the weight of C11030405-A in standard solution (mg)
$W_S$ represents the weight of sample (mg)
$V_{STD}$ represents the dilution volume of C11030405-A in standard solution (mL)
$V_S$ represents the dilution volume of sample (mL)
$A_S$ represents the peak area of C11030405-A in sample solution
$A_{STD}$ represents the peak area of C11030405-A in standard solution
$P_W$ represents the assay value of C11030405-A reference standard
K represents the dilution ratio 3.6 (IPC) Testing Item: Residual Compound C11030405-A
3.6.1 Preparation of solutions
3.6.1.1 Preparation of standard solution
Accurately weigh approximately 20 mg C11030405-A standard into a 100 mL volumetric flask, dissolve and dilute to volume with diluent, mix well.
3.6.1.2 Preparation of sample solution
Inject sample solution directly. If the concentration is too high, dilute to appropriate concentration with diluent to reach equivalent intensity of C11030405-A in the sample as it is in the standard.
3.6.2 Sample analysis
Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

3.6.3 Calculation
As per external standard method, calculate the residual compound C11030405-A as follows:

$$\text{Residual Compound } A(\%, w/w) = \frac{W_{STD} \times P_W}{V_{STD} \times A_{STD}} \times \frac{V_s \times A_s}{W_s} \times 100\%$$

$$\text{Or Residual Compound } A(g/L) = \frac{W_{STD} \times P_W}{V_{STD} \times A_{STD}} \times A_S \times K$$

Where: $W_{STD}$ represents the weight of C11030405-A in standard solution (mg)
$W_S$ represents the weight of sample (mg)
$V_{STD}$ represents the dilution volume of C11030405-A in standard solution (mL)
$V_S$ represents the dilution volume of sample (mL)
$A_S$ represents the peak area of C11030405-A in sample solution
$A_{STD}$ represents the peak area of C11030405-A in standard solution
$P_W$ represents the assay value of C11030405-A reference standard
K represents the dilution ratio 7.2.4. Method 4
4.1 Instrument
GC, equipped with FID detector
Electronic analytical balance
4.2 Reagent
DMF (HPLC Grade)
4.3 Chromatographic Conditions

| | |
|---|---|
| Column: | DB-624 (30 m * 0.32 mm ID * 1.8 μm) |
| FID Temperature: | 240° C. |
| $H_2$: | 40 mL/min |
| Air: | 400 mL/min |
| Make up ($N_2$) Flow: | 30 mL/min |
| Temperature Program: | 45° C. (5 min) → 10° C./min → 220° C. (3 min for blank and std, 10 min for sample) |
| Injector Temperature: | 200° C. |
| Split Ratio: | 20:1 |
| Carrier Gas: | $N_2$ |
| Control Mode: | SHIMADZU 2010: Linear Velocity or Agilent 7890: Constant flow |
| Column Flow: | 1.2 mL/min |
| Injection Volume: | 1.0 μL |
| Diluent: | DMF |
| Needle Wash: | DMF |

NOTE:
1. In order to elute strongly retained components from the GC column and ensure the reproducibility of continuous sample injections, the hold time at 220° C. can be extended according to the different characteristic of the sample.
2. In order to ensure proper recovery of the residual solvents in the sample, the Linear Velocity must be tightly controlled.
4.4 Reference Retention Times (MT-12-0830-01)

| Compound ID | Acetic acid |
|---|---|
| RT (min) | 12.5 |

4.5 (IPC) Testing Item: Residual Solvents (Acetic acid)
4.5.1 Preparation of solutions
4.5.1.1 Preparation of standard solution
Accurately weigh approximately 100 mg Acetic acid into a 100 mL volumetric flask, dissolve and dilute to the volume with diluent. Accurately transfer 5 mL of this solution into a 50 mL volumetric flask, dilute to the volume with diluent, and mix well.
4.5.1.2 Preparation of sample solution (10 mg/mL)
For example: accurately weigh approximately 100 mg sample into a 10 mL volumetric flask, dissolve and dilute to the volume with diluent, mix well.
4.5.2 Sample analysis
Set up instrument condition, after baseline is stabilized, the following injection procedure should be followed:

| Serial No. | Sample Name | No. of Injection |
|---|---|---|
| 1. | Blank (sample diluent) | 1 or more |
| 2. | Standard solution | 1 |
| 3. | Sample solution | 1 |

4.5.3 Calculation
The blank should not contain peaks that may interfere with the quantitation of the relevant solvents. If the signal to noise (S/N) of interference peak is ≥10, the peak area must be revised before it is used to calculate the relevant residual solvent in the sample.

As per external standard method, calculate the value of individual residual solvent as follows:

$$\text{Individual Residual Solvent (ppm)} = \frac{W_{STD}}{V_{STD} \times A_{STD}} \times \frac{V_s \times A_s}{W_s} \times 10^6$$

$$\text{Or Individual Residual Solvent (\%, w/w)} = \frac{W_{STD}}{V_{STD} \times A_{STD}} \times \frac{V_s \times A_s}{W_s} \times 100\%$$

Where: $W_{STD}$ represents the weight of specified solvent in standard solution (mg)
$W_S$ represents the weight of sample (mg)
$V_{STD}$ represents the dilution volume of specified solvent in standard solution (mL)
$V_S$ represents the dilution volume of sample (mL)
$A_S$ represents the revised peak area of specified solvent in sample solution
$A_{STD}$ represents the revised peak area of specified solvent in standard solutions Example 3

In-process Controls (IPC) for Synthesis of Compound Int B (C11030405-B)

7.3.1. Method 1
1.1 Instrument
Karl Fischer Titrator
1.2 Type of titration solutions
HYDRANAL Composite 5
Methanol (HPLC Grade)
1.3 Analytical procedure
After pre-titration is stabilized, take approximately 0.2 g of solid sample or 1 mL of liquid sample to determine the water content. Two samples should be tested in parallel. Report the average value if both of test results meet principle of the method. (The amount of sample can be added or reduced according to the actual water content, but the reason must be recorded)
1.4 Testing item: Water content (KF)
7.3.2. Method 2
2.1 Instrument
HPLC, equipped with PDA detector and auto-sampler
Electronic analytical balance
Pure water generator
2.2 Reagent
Acetonitrile (HPLC Grade)
TFA (HPLC Grade)
Methanol (HPLC Grade)
2.3 Chromatographic Conditions

| Column: | Waters XTerra MS C18 (150 × 4.6 mm, 3.5 μm) |
| --- | --- |
| PDA Detector Wavelength: | 220 nm |
| Column Temperature: | 40° C. |
| Column Flow: | 1.0 mL/min |
| Injection Volume: | 10 μL |
| Acquisition Time: | 35 min |
| Run Time: | 35 min |
| Diluent: | Methanol |
| Needle Wash: | Methanol |

Mobile Phase A (0.05% TFA-H$_2$O): Accurately transfer 0.5 mL TFA into 1000 mL purified water and mix well. The solution should be filtrated and degassed before use.

Mobile Phase B (0.05% TFA-ACN): Accurately transfer 0.5 mL TFA into 1000 mL acetonitrile and mix well.

Gradient Program:

| Time (min) | A % | B % |
| --- | --- | --- |
| 0.0 | 95 | 5 |
| 3.0 | 95 | 5 |
| 26.0 | 10 | 90 |
| 28.0 | 10 | 90 |
| 28.1 | 95 | 5 |
| 35.0 | | stop |

NOTE: The chromatographic conditions were developed with Shimadzu LC-20A series HPLC.

2.4 Reference Retention Times (MT-14-0017-01)

| Compound ID | C11030405-A | C11030405-B | C11030405-SM2 |
| --- | --- | --- | --- |
| RT (min) | 10.0 | 22.4 | 23.9 |
| RRT | 0.45 | 1.00 | 1.07 |

2.5 (IPC) Testing Item: A/B %
2.5.1 Preparation of solutions
2.5.1.1 Preparation of standard solution For example: Weigh approximately 2 mg C11030405-A and 35 mg C11030405-B standard into a 100 mL volumetric flask, dissolve and dilute to the volume with diluent, mix well.

2.5.1.2 Preparation of sample solution

Dilute the reaction solution about 500 times with diluent and mix well. The dilution ratio may be adjusted to reach equivalent intensity of C11030405-B in the sample as it is in the standard.

2.5.2 Sample analysis

Set up instrument condition, after baseline is stabilized, the following injection procedure should be followed:

| Serial No. | Sample Name | No. of Injection |
| --- | --- | --- |
| 1 | Blank (sample diluent) | 1 or more |
| 2 | Standard solution | 1 |
| 3 | Sample solution | 1 |

2.5.3 Calculation

As per peak area of specified compound, calculate the value of A/B % as follows:

$$A/B \ \% = \frac{S_A}{S_B} \times 100\%$$

Where: $S_A$ represents the peak area of C11030405-A in sample solution
$S_B$ represents the peak area of C11030405-B in sample solution 2.6 (IPC) Testing Item: Related substances and Assay of C11030405-B 2.6.1 Preparation of solutions 2.6.1.1 Preparation of marker standard solution for related substances determination For example: Weigh approximately 35 mg C11030405-SM2, 2 mg C11030405-A and 35 mg C11030405-B standard into a 100 mL volumetric flask, dissolve and dilute to the volume with diluent, mix well. Label it as 1# standard solution.

2.6.1.2 Preparation of standard solution for assay determination

Accurately weigh approximately 88 mg C11030405-B standard into a 25 mL volumetric flask, dissolve and dilute to volume with diluent, mix well. Accurately transfer this solution 1.0 mL into a 10 mL volumetric flask, dilute to volume with diluent, mix well. Label it as 2# standard solution.

2.6.1.3 Preparation of sample solution

For example: For solid: Accurately weigh approximately 88 mg sample into a 25 mL volumetric flask, dissolve and dilute to the volume with diluent, mix well. Accurately transfer this solution 1.0 mL into a 10 mL volumetric flask, dilute to volume with diluent, mix well. The weight of sample may be adjusted to reach equivalent intensity of C11030405-B in the sample as it is in the standard.

For liquid: Accurately transfer 1.0 mL sample into a 100 mL volumetric flask containing 20 mL of diluent, dissolve and dilute to the volume with diluent, mix well, accurately transfer this solution 1.0 mL into a 25 mL volumetric flask, dilute to volume with diluent, mix well. If the concentration is too high, dilute to appropriate concentration with diluent to reach equivalent intensity of C11030405-B in the sample as it is in the standard.

2.6.2 Sample analysis

Set up instrument condition, after baseline is stabilized, the following injection procedure should be followed:

For related substance determination:

| Serial No. | Sample Name | No. of Injection |
| --- | --- | --- |
| 1 | Blank (sample diluent) | 1 or more |
| 2 | 1# standard solution | 1 |
| 3 | Sample solution | 1 |

For assay determination:

| Serial No. | Sample Name | No. of Injection |
| --- | --- | --- |
| 1 | Blank (sample diluent) | 1 or more |
| 2 | 2# standard solution | 1 |
| 3 | Sample solution | 1 |

For related substance and assay determination:

| Serial No. | Sample Name | No. of Injection |
| --- | --- | --- |
| 1 | Blank (sample diluent) | 1 or more |
| 2 | 1# standard solution | 1 |
| 3 | 2# standard solution | 1 |
| 4 | Sample solution | 1 |

2.63 Calculation 2.6.3.1 Identification: The retention time range for identification of C11030405-B in the sample solution should be ±5.0% of the retention time of C11030405-B in 1# standard solution.

2.6.3.2 Label the known impurities in the sample chromatogram refer to 1# standard chromatogram.

2.6.3.3 Only integrate the peaks ≥0.05% in sample chromatogram, then calculate the peak area percentage (HPLC Area %) of C11030405-B.

2.6.3.4 As per external standard method, calculate the assay (%, w/w) of sample as follows:

$$\text{Assay}(\%, w/w) = \frac{W_{STD} \times P_W}{V_{STD} \times A_{STD}} \times \frac{V_s \times A_s}{W_s} \times 100\%$$

$$\text{Or Assay}(g/L) = \frac{W_{STD} \times P_W}{V_{STD} \times A_{STD}} \times A_s \times K$$

Where: $W_{STD}$ represents the weight of C11030405-B in standard solution (mg)

$W_S$ represents the weight of sample (mg)

$V_{STD}$ represents the dilution volume of C11030405-B in standard solution (mL)

$V_S$ represents the dilution volume of sample (mL)

$A_S$ represents the peak area of C11030405-B in sample solution $A_{STD}$ represents the peak area of C11030405-B in standard solution $P_W$ represents the assay value of C11030405-B reference standard K represents the dilution ratio 2.7 (IPC) Testing Item: Residual Compound C11030405-B 2.7.1 Preparation of solutions 2.7.1.1 Preparation of standard solution Accurately weigh approximately 88 mg C11030405-B standard into a 25 mL volumetric flask, dissolve and dilute to volume with diluent, mix well. Accurately transfer this solution 1.0 mL into a 10 mL volumetric flask, dilute to volume with diluent, mix well.

2.7.1.2 Preparation of sample solution

Inject sample solution directly. If the concentration is too high, dilute to appropriate concentration with diluent to reach equivalent intensity of C11030405-B in the sample as it is in the standard.

2.7.2 Sample analysis

Set up instrument condition, after baseline is stabilized, the following injection procedure should be followed:

| Serial No. | Sample Name | No. of Injection |
| --- | --- | --- |
| 1 | Blank (sample diluent) | 1 or more |
| 2 | Standard solution | 1 |
| 3 | Sample solution | 1 |

2.7.3 Calculation

As per external standard method, calculate the residual compound C11030405-B as follows:

$$\text{Residual Compound } B(\%, w/w) = \frac{W_{STD} \times P_W}{V_{STD} \times A_{STD}} \times \frac{V_s \times A_s}{W_s} \times 100\%$$

$$\text{Or Residual Compound } B(g/L) = \frac{W_{STD} \times P_W}{V_{STD} \times A_{STD}} \times A_S \times K$$

Where: $W_{STD}$ represents the weight of C11030405-B in standard solution (mg)

$W_S$ represents the weight of sample (mg)

$V_{STD}$ represents the dilution volume of C11030405-B in standard solution (mL)

$V_S$ represents the dilution volume of sample (mL)

$A_S$ represents the peak area of C11030405-B in sample solution $A_{STD}$ represents the peak area of C11030405-B in standard solution $P_W$ represents the assay value of C11030405-B reference standard K represents the dilution ratio 2.8 (IPC test for intermediate) Testing Item: Related substances and Assay of C11030405-B 2.8.1 Preparation of solutions 2.8.1.1 Preparation of standard solution Accurately weigh approximately 88 mg C11030405-B standard into a 25 mL volumetric flask, dissolve and dilute to volume with diluent, mix well. Accurately transfer this solution 1.0 mL into a 10 mL volumetric flask, dilute to volume with diluent, mix well. Two standard solutions should be prepared in parallel and labeled as 1# and 2# standard solution.

2.8.1.2 Preparation of resolution solution

For example: Weigh approximately 35 mg C11030405-SM2, 2 mg C11030405-A and 35 mg C11030405-B standard into a 100 mL volumetric flask, dissolve and dilute to the volume with diluent, mix well. Label it as 3# standard solution.

2.8.1.3 Preparation of sample solution

For solid sample: Accurately weigh approximately 88 mg sample into a 25 mL volumetric flask, dissolve and dilute to the volume with diluent, mix well. Accurately transfer this solution 1.0 mL into a 10 mL volumetric flask, dilute to volume with diluent, mix well. The weight of sample may be adjusted to reach equivalent intensity of C11030405-B in the sample as it is in the standard. Two sample solutions should be prepared in parallel and labeled as 1# sample solution and 2# sample solution.

For liquid sample: Accurately transfer 1.0 mL sample into a 100 mL volumetric flask containing 20 mL of diluent, dissolve and dilute to the volume with diluent, mix well, accurately transfer this solution 1.0 mL into a 25 mL volumetric flask, dilute to volume with diluent, mix well. If the concentration is too high, dilute to appropriate concentration with diluent to reach equivalent intensity of C11030405-B in the sample as it is in the standard. Two sample solutions should be prepared in parallel and labeled as 1# sample solution and 2# sample solution.

2.8.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 3# standard solution | 1 |
| 3 | 1# sample solution | 1 |
| 4 | 2# sample solution | 1 |

For related substance and assay determination:

| Serial No. | Sample Name | No. of Injection |
|---|---|---|
| 1 | Blank (sample diluent) | 1 or more |
| 2 | 3# standard solution | 1 |
| 3 | 1# standard solution | 1 |
| 4 | 2# standard solution | 1 |
| 5 | 1# sample solution | 1 |
| 6 | 2# sample solution | 1 |

2.8.3 System suitability 2.8.3.1 The blank should not contain peaks that may interfere with the determination of C11030405-B. If an interference peak is observed, it should be <0.1% peak area of C11030405-B in 1# standard solution.

2.8.3.2 The tailing factor of C11030405-B in all standard solutions should be within 0.8-2.0.

2.8.3.3 The resolution between C11030405-B and its adjacent peaks in the 3# standard solution should be ≥1.5.

2.8.3.4 Calculate % Recovery of 2# STD as per the following calculation formula, % Recovery should be within 98.0%-102.0%.

$$\% \text{ Recovery of Check standard} = \frac{W_1 \times A_2}{W_2 \times A_1} \times 100\%$$

Where: $W_1$ represents the weight of C11030405-B in 1# standard solution (mg)

$W_2$ represents the weight of C11030405-B in 2# standard solution (mg)

$A_2$ represents the peak area of C11030405-B in 2# standard solution $A_1$ represents the peak area of C11030405-B in 1# standard solution 2.8.4 Calculation 2.8.4.1 Identification: The retention time range for identification of C11030405-B in the sample solution should be ±5.0% of the retention time of C11030405-B in 3# standard solution.

2.8.4.2 Related substances:

2.8.4.2.1 Label the known impurities in the sample chromatogram refer to 3# standard chromatogram.

2.8.4.2.2 Only integrate the peaks ≥0.05% in sample chromatogram, then calculate the peak area percentage (HPLC Area %) of C11030405-B. If two testing results are within specification limit and the RSD of two results is no more than 2.0%, the average result should be reported as the final result for purity (HPLC Area %).

2.8.4.3 Response factor

Calculate the RF in 1# and 2# standard solutions as follows:

$$RF = \frac{A_{STD} \times V_{STD}}{W_{STD} \times P_W}$$

Where: $A_{STD}$ represents the peak area of C11030405-B in standard solution $V_{STD}$ represents the dilution volume of standard solution (mL)

$W_{STD}$ represents the weight of C11030405-B in standard solution (mg)

$P_W$ represents the assay value of C11030405-B reference standard

2.8.4.4 Assay (%, w/w) of sample

Calculate the assay (%, w/w) of sample as follows:

$$\text{Assay}(\%, w/w) = \frac{V_s \times A_s}{W_s \times \overline{RF}} \times 100\%$$

Where: $W_S$ represents the weight of sample (mg)
$V_S$ represents the dilution volume of sample (mL)
$A_S$ represents the peak area of C11030405-B in sample solution
$\overline{RF}$ represents the average value of RF for two standard solutions If two testing results are within specification limit and the RSD of two results is no more than 2.0%, the average result should be reported as the final result for Assay (%, w/w).

Example 4

In-process Controls (IPC) for Synthesis of Compound Int C (C11030405-C)

7.4.1. Method 1
1.1 Instrument
Karl Fischer Titrator
1.2 Type of titration solutions
HYDRANAL Composite 5
Methanol (HPLC Grade)
1.3 Analytical procedure After pre-titration is stabilized, take approximately 0.2 g of solid sample or 1 mL of liquid sample to determine the water content. Two samples should be tested in parallel. Report the average value if both of test results meet principle of the method. (The amount of sample can be added or reduced according to the actual water content, but the reason must be recorded.)

1.4 Testing item: Water content (KF)
7.4.2. Method 2
2.1 Instrument
HPLC, equipped with PDA detector and auto-sampler
Electronic analytical balance
Pure water generator
2.2 Reagent
Acetonitrile (HPLC Grade)
2.3 Chromatographic Conditions

| Column: | Waters XBridge Shield RP18 (150 × 3.0 mm, 3.5 μm) |
| --- | --- |
| PDA Detector Wavelength: | 220 nm |
| Column Temperature: | 40° C. |
| Column Flow: | 1.0 mL/min |
| Injection Volume: | 10 μL |
| Acquisition Time: | 33 min |
| Run Time: | 33 min |
| Diluent: | Methanol |
| Needle Wash: | Methanol |

Mobile Phase A (0.05% TFA-H2O): Accurately transfer 0.5 mL TFA into 1000 mL purified water and mix well. The solution should be filtrated and degassed before use.
Mobile Phase B (0.05% TFA-ACN): Accurately transfer 0.5 mL TFA into 1000 mL acetonitrile and mix well.

Gradient Program:

| Time (min) | A % | B % |
| --- | --- | --- |
| 0.0 | 95 | 5 |
| 5.0 | 95 | 5 |
| 24.0 | 10 | 90 |
| 27.00 | 10 | 90 |
| 27.10 | 95 | 5 |
| 33.0 | | stop |

NOTE: The chromatographic conditions were developed with Agilent 1200 series HPLC.

2.4 Reference Retention Times (MT-11-0516-01, Agilent)

| Compound ID | C11030405-C | C11030405-B |
| --- | --- | --- |
| RT (mm) | 14.8 | 17.2 |
| RRT | 1.00 | 1.16 |

2.5 (IPC) Testing Item: B/C %
2.5.1 Preparation of solutions
2.5.1.1 Preparation of standard solution For example: Weigh approximately 5 mg C11030405-B and 30 mg C11030405-C standard into a 100 mL volumetric flask, dissolve and dilute to the volume with diluent, mix well.

2.5.1.2 Preparation of sample solution

Dilute the reaction solution about 1000 times with diluent and mix well. The dilution ratio may be adjusted to reach equivalent intensity of 01030405-C in the sample as it is in the standard.

2.5.2 Sample analysis

Set up instrument condition, after baseline is stabilized, the following injection procedure should be followed:

| Serial No. | Sample Name | No. of Injection |
| --- | --- | --- |
| 1 | Blank (sample diluent) | 1 or more |
| 2 | Standard solution | 1 |
| 3 | Sample solution | 1 |

2.5.3 Calculation

As per peak area of specified compound, calculate the value of B/C % as follows:

$$B/C \ \% = \frac{S_B}{S_C} \times 100\%$$

Where: $S_B$ represents the peak area of C11030405-B in sample solution
$S_C$ represents the peak area of C11030405-C in sample solution 2.6 (IPC) Testing Item: Related substances and Assay of C11030405-C
2.6.1 Preparation of solutions
2.6.1.1 Preparation of marker standard solution for related substances determination For example: Weigh approximately 5 mg C11030405-B and 30 mg C11030405-C standard into a 100 mL volumetric flask, dissolve and dilute to the volume with diluent, mix well. Label it as 1# standard solution.

2.6.1.2 Preparation of standard solution for assay determination

Accurately weigh approximately 30 mg C11030405-C standard into a 100 mL volumetric flask, dissolve and dilute to volume with diluent, mix well. Label it as 2# standard solution.

2.6.1.3 Preparation of sample solution

For example: Accurately weigh approximately 30 mg sample into a 100 mL volumetric flask, dissolve and dilute to the volume with diluent, mix well. The weight of sample may be adjusted to reach equivalent intensity of C11030405-C in the sample as it is in the standard.

2.6.2 Sample analysis

Set up instrument condition, after baseline is stabilized, the following injection procedure should be followed:

For related substance determination:

| Serial No. | Sample Name | No. of Injection |
|---|---|---|
| 1. | Blank (sample diluent) | 1 or more |
| 2. | 1# standard solution | 1 |
| 3. | Sample solution | 1 |

For assay determination:

| Serial No. | Sample Name | No. of Injection |
|---|---|---|
| 1 | Blank (sample diluent) | 1 or more |
| 2 | 2# standard solution | 1 |
| 3 | Sample solution | 1 |

For related substance and assay determination:

| Serial No. | Sample Name | No. of Injection |
|---|---|---|
| 1 | Blank (sample diluent) | 1 or more |
| 2 | 1# standard solution | 1 |
| 3 | 2# standard solution | 1 |
| 4 | Sample solution | 1 |

2.6.3 Calculation 2.6.3.1 Identification: The retention time range for identification of C11030405-C in the sample solution should be ±5.0% of the retention time of C11030405-C in 1# standard solution.

2.6.3.2 Label the known impurities in the sample chromatogram refer to 1# standard chromatogram.

2.6.3.3 Calculate the peak area percentage (HPLC Area %) of C11030405-C.

2.6.3.4 As per external standard method, calculate the assay (%, w/w) of sample as follows:

$$\text{Assay}(\%, \text{w/w}) = \frac{W_{STD} \times P_w}{V_{STD} \times A_{STD}} \times \frac{V_s \times A_s}{W_s} \times 100\%$$

$$\text{Assay}(\text{g/L}) = \frac{W_{STD} \times P_w}{V_{STD} \times A_{STD}} \times A_s \times K$$

Where: $W_{STD}$ represents the weight of C11030405-C in standard solution (mg)
$W_S$ represents the weight of sample (mg)
$V_{STD}$ represents the dilution volume of C11030405-C in standard solution (mL)
$V_S$ represents the dilution volume of sample (mL)
$A_S$ represents the peak area of C11030405-C in sample solution
$A_{STD}$ represents the peak area of C11030405-C in standard solution
$P_W$ represents the assay value of C11030405-C reference standard
K represents the dilution ratio 2.7 (IPC)Testing Item: Residual Compound C11030405-C 2.7.1 Preparation of solutions 2.7.1.1 Preparation of standard solution Accurately weigh approximately 30 mg C11030405-C standard into a 100 mL volumetric flask, dissolve and dilute to volume with diluent, mix well.

2.7.1.2 Preparation of sample solution

Inject sample solution directly. If the concentration is too high, dilute to appropriate concentration with diluent to reach equivalent intensity of C11030405-C in the sample as it is in the standard.

2.7.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.7.3 Calculation

As per external standard method, calculate the residual compound C11030405-C as follows:

$$\text{Residual Compound } C(\%, \text{w/w}) = \frac{W_{STD} \times P_w}{V_{STD} \times A_{STD}} \times \frac{V_s \times A_s}{W_s} \times 100\%$$

Or $$\text{Residual Compound } C(\text{g/L}) = \frac{W_{STD} \times P_w}{V_{STD} \times A_{STD}} \times A_s \times K$$

Where: $W_{STD}$ represents the weight of C11030405-C in standard solution (mg)
$W_S$ represents the weight of sample (mg)
$V_{STD}$ represents the dilution volume of C11030405-C in standard solution (mL)
$V_S$ represents the dilution volume of sample (mL)
$A_S$ represents the peak area of C11030405-C in sample solution
$A_{STD}$ represents the peak area of C11030405-C in standard solution
$P_W$ represents the assay value of C11030405-C reference standard
K represents the dilution ratio 2.8 (IPC test for intermediate) Testing Item: Related substances and Assay of C11030405-C 2.8.1 Preparation of solutions 2.8.1.1 Preparation of standard solution Accurately weigh approximately 30 mg C11030405-C standard into a 100 mL volumetric flask, dissolve and dilute to volume with diluent, mix well. Two standard solutions should be prepared in parallel and labeled as 1# and 2# standard solution.

2.8.1.2 Preparation of resolution solution

For example: Weigh approximately 5 mg C11030405-B and 30 mg C11030405-C standard into a 100 mL volumetric flask, dissolve and dilute to the volume with diluent, mix well. Label it as 3# standard solution.

2.8.1.3 Preparation of sample solution

For solid sample: Accurately weigh approximately 30 mg sample into a 100 mL volumetric flask, dissolve and dilute to the volume with diluent, mix well. The weight of sample may be adjusted to reach equivalent intensity of C11030405-C in the sample as it is in the standard. Two sample solutions should be prepared in parallel and labeled as 1# sample solution and 2# sample solution.

2.8.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 3# standard solution | 1 |
| 3 | 1# sample solution | 1 |
| 4 | 2# sample solution | 1 |

For related substance and assay determination:

| Serial No. | Sample Name | No. of Injection |
|---|---|---|
| 1 | Blank (sample diluent) | 1 or more |
| 2 | 3# standard solution | 1 |
| 3 | 1# standard solution | 1 |
| 4 | 2# standard solution | 1 |
| 5 | 1# sample solution | 1 |
| 6 | 2# sample solution | 1 |

2.8.3 System suitability 2.8.3.1 The blank should not contain peaks that may interfere with the determination of C11030405-C. If an interference peak is observed, it should be <0.05% peak area of C11030405-C in 1# standard solution.

2.8.3.2 The tailing factor of C11030405-C in all standard solutions should be within 0.8-2.0.

2.8.3.3 The resolution between C11030405-C and its adjacent peaks in the 3# standard solution should be ≥1.5.

2.8.3.4 Calculate % Recovery of 2# STD used as Check STD as per the following calculation formula, % Recovery should be within 98.0%-102.0%.

$$\% \text{ Recovery of Check standard} = \frac{W_1 \times A_2}{W_2 \times A_1} \times 100\%$$

Where: $W_1$ represents the weight of C11030405-C in 1# standard solution (mg)

$W_2$ represents the weight of C11030405-C in 2# standard solution (mg)

$A_2$ represents the peak area of C11030405-C in 2# standard solution $A_1$ represents the peak area of C11030405-C in 1# standard solution 2.8.4 Calculation 2.8.4.1 Identification: The retention time range for identification of C11030405-C in the sample solution should be ±5.0% of the retention time of C11030405-C in 3# standard solution.

2.8.4.2 Related substances:

2.8.4.2.1 Label the known impurities in the sample chromatogram refer to 3# standard chromatogram.

2.8.4.2.2 As per peak area percentage, calculate the peak area percentage (HPLC Area %) of C11030405-C. If two testing results are within specification limit and the RSD of two results is no more than 2.0%, the average result should be reported as the final result for purity (HPLC Area %) of C11030405-C.

2.8.4.3 Response factor

Calculate the RF in 1# and 2# standard solutions as follows:

$$RF = \frac{A_{STD} \times V_{STD}}{W_{STD} \times P_W}$$

Where: $A_{STD}$ represents the peak area of C11030405-C in standard solution $V_{STD}$ represents the dilution volume of standard solution (mL)

$W_{STD}$ represents the weight of C11030405-C in standard solution (mg)

$P_W$ represents the assay value of C11030405-C reference standard 2.8.4.4 Assay (%, w/w) of sample Calculate the assay (%, w/w) of sample as follows:

$$\text{Assay}(\%, w/w) = \frac{V_s \times A_s}{W_s \times \overline{RF}} \times 100\%$$

Where: $W_S$ represents the weight of sample (mg)

$V_S$ represents the dilution volume of sample (mL)

$A_S$ represents the peak area of C11030405-C in sample solution $\overline{RF}$ represents the average value of RF for two standard solutions If two testing results are within specification limit and the RSD of two results is no more than 2.0%, the average result should be reported as the final result for Assay (%, w/w).

Example 5

In-Process Controls (IPC) for Synthesis of Compound Int D (C1030405-D)

7.5.1. Method 1
1.1 Instrument
Karl Fischer Titrator
1.2 Type of titration solutions
HYDRANAL Composite 5
Methanol (HPLC Grade)
1.3 Analytical procedure After pre-titration is stabilized, take approximately 0.2 g of solid sample or 1 mL of liquid sample to determine the water content. Two samples should be tested in parallel. Report the average value if both of test results meet principle of the method. (The amount of sample can be added or reduced according to the actual water content, but the reason must be recorded.)

1.4 Testing item: Water content (KF)
7.5.2. Method 2
2.1 instrument
HPLC, equipped with PDA detector and auto-sampler
Electronic analytical balance
Pure water generator
2.2 Reagent
Acetonitrile (HPLC Grade)
2.3 Chromatographic Conditions

| Column: | Waters XBridge Shield RP18 (150 × 3.0 mm, 3.5 μm) |
|---|---|

-continued

| | |
|---|---|
| PDA Detector Wavelength: | 220 nm |
| Column Temperature: | 40° C. |
| Column Flow: | 1.0 mL/min |
| Injection Volume: | 10 μL |
| Acquisition Time: | 33 min |
| Run Time: | 33 min |
| Diluent: | 1. Methanol<br>2. Acetonitrile: water = 50:50(v/v) (For residual C of aqueous phase) |
| Needle Wash: | Methanol |

Mobile Phase A (0.05% TFA-H2O): Accurately transfer 0.5 mL TFA into 1000 mL purified water and mix well. The solution should be filtrated and degassed before use.

Mobile Phase B (0.05% TFA-ACN): Accurately transfer 0.5 mL TFA into 1000 mL acetonitrile and mix well.

Gradient Program:

| Time (min) | A % | B % |
|---|---|---|
| 0.0 | 95 | 5 |
| 5.0 | 95 | 5 |
| 24.0 | 10 | 90 |
| 27.00 | 10 | 90 |
| 27.10 | 95 | 5 |
| 33.0 | | stop |

NOTE: The chromatographic conditions were developed with Shimadzu LC-20A series HPLC.

2.4 Reference Retention Times (MT-11-0517-01)

| Compound ID | C11030405-C | C11030405-D |
|---|---|---|
| RT (min) | 14.6 | 17.6 |
| RRT | 0.83 | 1.00 |

2.5 (IPC) Testing Item: CM %

2.5.1 Preparation of solutions 2.5.1.1 Preparation of standard solution

For example: Weigh approximately 5 mg C11030405-C and 25 mg C11030405-D standard into a 50 mL volumetric flask, dissolve and dilute to the volume with diluent 1, mix well.

2.5.1.2 Preparation of sample solution

Dilute the reaction solution about 400 times with diluent 1 and mix well. The dilution ratio may be adjusted to reach equivalent intensity of C11030405-D in the sample as it is in the standard.

2.5.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.5.3 Calculation

As per peak area of specified compound, calculate the value of C/D % as follows:

$$C/D \% = \frac{S_C}{S_D} \times 100\%$$

Where: $S_C$ represents the peak area of C11030405-C in sample solution $S_D$ represents the peak area of C11030405-D in sample solution 2.6 (IPC) Testing Item: Related substances and Assay of C11030405-D 2.6.1 Preparation of solutions 2.6.1.1 Preparation of marker standard solution for related substances determination For example: Weigh approximately 5 mg C11030405-C and 25 mg C11030405-D standard into a 50 mL volumetric flask, dissolve and dilute to the volume with diluent 1, mix well. Label it as 1# standard solution.

2.6.1.2 Preparation of standard solution for assay determination

Accurately weigh approximately 50 mg C11030405-D standard into a 100 mL volumetric flask, dissolve and dilute to volume with diluent 1, mix well. Label it as 2# standard solution.

2.6.1.3 Preparation of sample solution

For example: Accurately weigh approximately 50 mg sample into a 100 mL volumetric flask, dissolve and dilute to the volume with diluent 1, mix well. The weight of sample may be adjusted to reach equivalent intensity of C11030405-D in the sample as it is in the standard.

2.6.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 1# standard solution | 1 |
| 3 | Sample solution | 1 |

For assay determination:

| Serial No. | Sample Name | No. of Injection |
|---|---|---|
| 1 | Blank (sample diluent) | 1 or more |
| 2 | 2# standard solution | 1 |
| 3 | Sample solution | 1 |

For related substance and assay determination:

| Serial No. | Sample Name | No. of Injection |
|---|---|---|
| 1 | Blank (sample diluent) | 1 or more |
| 2 | 1# standard solution | 1 |
| 3 | 2# standard solution | 1 |
| 4 | Sample solution | 1 |

2.6.3 Calculation 2.6.3.1 Label the known impurities in the sample chromatogram refer to 1# standard chromatogram.

2.6.3.2 As per peak area percentage, calculate the peak area percentage (HPLC Area %) of C11030405-D.

2.6.3.3 As per external standard method, calculate the assay (%, w/w) of sample as follows:

$$\text{Assay}(\%, \text{w/w}) = \frac{W_{STD} \times P_w}{V_{STD} \times A_{STD}} \times \frac{V_s \times A_s}{W_s} \times 100\%$$

Or $$\text{Assay}(g/L) = \frac{W_{STD} \times P_w}{V_{STD} \times A_{STD}} \times A_s \times K$$

Where: $W_{STD}$ represents the weight of C11030405-D in standard solution (mg)

$W_S$ represents the weight of sample (mg)

$V_{STD}$ represents the dilution volume of C11030405-D in standard solution (mL)

$V_S$ represents the dilution volume of sample (mL)

$A_S$ represents the peak area of C11030405-D in sample solution $A_{STD}$ represents the peak area of C11030405-D in standard solution $P_W$ represents the assay value of C11030405-D reference standard K represents the dilution ratio 2.7 (IPC)Testing Item: Residual Compound C11030405-D 2.7.1 Preparation of solutions 2.7.1.1 Preparation of standard solution Accurately weigh approximately 50 mg C11030405-D standard into a 100 mL volumetric flask, dissolve and dilute to volume with diluent 1, mix well.

2.7.1.2 Preparation of sample solution

For aqueous phase: Inject sample solution directly. If the concentration is too high, dilute to appropriate concentration with diluent 2 to reach equivalent intensity of C11030405-D in the sample as it is in the standard.

For active carbon: Accurately weigh approximately 0.5 g sample into a 10 mL volumetric flask, dissolve and dilute to the volume with diluent 1, mix well. Degas and filter using a 0.45 μm filter. The weight of sample may be adjusted to reach equivalent intensity of C11030405-D in the sample as it is in the standard.

2.7.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.7.3 Calculation

As per external standard method, calculate the residual compound C11030405-D as follows:

$$\text{Residual Compound } D(\%, \text{w/w}) = \frac{W_{STD} \times P_w}{V_{STD} \times A_{STD}} \times \frac{V_s \times A_s}{W_s} \times 100\%$$

Or $$\text{Residual Compound } D(g/L) = \frac{W_{STD} \times P_w}{V_{STD} \times A_{STD}} \times A_s \times K$$

Where: $W_{STD}$ represents the weight of C11030405-D in standard solution (mg)

$W_S$ represents the weight of sample (mg)

$V_{STD}$ represents the dilution volume of C11030405-D in standard solution (mL)

$V_S$ represents the dilution volume of sample (mL)

$A_S$ represents the peak area of C11030405-D in sample solution $A_{STD}$ represents the peak area of C11030405-D in standard solution $P_W$ represents the assay value of C11030405-D reference standard K represents the dilution ratio 2.8 (IPC test for intermediate) Testing Item: Related substances and Assay of C11030405-D 2.8.1 Preparation of solutions 2.8.1.1 Preparation of standard solution Accurately weigh approximately 50 mg C11030405-D standard into a 100 mL volumetric flask, dissolve and dilute to volume with diluent, mix well. Two standard solutions should be prepared in parallel and labeled as 1# and 2# standard solution.

2.8.1.2 Preparation of resolution solution

For example: Weigh approximately 5 mg C11030405-C and 25 mg C11030405-D standard into a 50 mL volumetric flask, dissolve and dilute to the volume with diluent, mix well. Label it as 3# standard solution.

2.8.1.3 Preparation of sample solution

For solid sample: Accurately weigh approximately 50 mg sample into a 100 mL volumetric flask, dissolve and dilute to the volume with diluent, mix well. The weight of sample may be adjusted to reach equivalent intensity of C11030405-D in the sample as it is in the standard. Two sample solutions should be prepared in parallel and labeled as 1# sample solution and 2# sample solution.

2.8.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 3# standard solution | 1 |
| 3 | 1# sample solution | 1 |
| 4 | 2# sample solution | 1 |

For related substance and assay determination:

| Serial No. | Sample Name | No. of Injection |
|---|---|---|
| 1 | Blank (sample diluent) | 1 or more |
| 2 | 3# standard solution | 1 |
| 3 | 1# standard solution | 1 |
| 4 | 2# standard solution | 1 |
| 5 | 1# sample solution | 1 |
| 6 | 2# sample solution | 1 |

2.8.3 System suitability 2.8.3.1 The blank should not contain peaks that may interfere with the determination of C11030405-D. If an interference peak is observed, it should be <0.05% peak area of C11030405-D in 1# standard solution.

2.8.3.2 The tailing factor of C11030405-D in all standard solutions should be within 0.8-2.0.

2.8.3.3 The resolution between C11030405-D and its adjacent peaks in the 3# standard solution should be ≥1.2.

2.8.3.4 Calculate % Recovery of 2# STD used as Check STD as per the following calculation formula, % Recovery should be within 98.0%~102.0%.

$$\% \text{ Recovery of Check standard} = \frac{W_1 \times A_2}{W_2 \times A_1} \times 100\%$$

Where: $W_1$ represents the weight of C11030405-D in 1# standard solution (mg)
$W_2$ represents the weight of C11030405-D in 2# standard solution (mg)
$A_2$ represents the peak area of C11030405-D in 2# standard solution
$A_1$ represents the peak area of C11030405-D in 1# standard solution 2.8.4 Calculation
2.8.4.1 Identification: The retention time range for identification of C11030405-D in the sample solution should be ±5.0% of the retention time of C11030405-D in 3# standard solution.
2.8.4.2 Related substances:
2.8.4.2.1 Label the known impurities in the sample chromatogram refer to 3# standard chromatogram.
2.8.4.2.2 As per peak area percentage, calculate the peak area percentage (HPLC Area %) of C11030405-D. If two testing results are within specification limit and the RSD of two results is no more than 2.0%, the average result should be reported as the final result for purity (HPLC Area %) of C11030405-D.
2.8.4.3 Response factor
Calculate the RF in 1# and 2# standard solutions as follows:

$$RF = \frac{A_{STD} \times V_{STD}}{W_{STD} \times P_W}$$

Where: $A_{STD}$ represents the peak area of C11030405-D in standard solution
$V_{STD}$ represents the dilution volume of standard solution (mL)
$W_{STD}$ represents the weight of C11030405-D in standard solution (mg)
$P_W$ represents the assay value of C11030405-D reference standard 2.8.4.4 Assay (%, w/w) of sample
Calculate the assay (%, w/w) of sample as follows:

$$\text{Assay}(\%, w/w) = \frac{V_s \times A_s}{W_s \times \overline{RF}} \times 100\%$$

Where: $W_S$ represents the weight of sample (mg)
$V_S$ represents the dilution volume of sample (mL)
$A_S$ represents the peak area of C11030405-D in sample solution
$\overline{RF}$ represents the average value of RF for two standard solutions If two testing results are within specification limit and the RSD of two results is no more than 2.0%, the average result should be reported as the final result for Assay (%, w/w).

7.5.3. Method 3
3.1 Instrument
Karl Fischer Titrator
3.2 Type of titration solutions
HYDRANAL Composite 5
Methanol (HPLC Grade)
3.3 Analysis method
After pre-titration is stabilized, take approximately 3 g or 3 mL sample and determine the water content. (The amount of sample can be added or reduced according to the actual water content, but the reason must be recorded.)
3.4 Testing item: Water content for material (KF)

Example 6

In-Process Controls (IPC) for Synthesis of Compound Int E (C11030405-E)

7.6.1. Method 1
1.1 Instrument
Karl Fischer Titrator
1.2 Type of titration solutions
HYDRANAL Composite 5
Methanol (HPLC Grade)
1.3 Analytical procedure
After pre-titration is stabilized, take approximately 0.1 g of solid sample or 1 mL of liquid sample to determine the water content. Two samples should be tested in parallel. Report the average value if both of test results meet principle of the method. (The amount of sample can be added or reduced according to the actual water content, but the reason must be recorded.)
1.4 Testing item: Water content (KF)
7.6.2. Method 2
2.1 Instrument
HPLC, equipped with PDA detector and auto-sampler
Electronic analytical balance
Pure water generator
2.2 Reagent
Acetonitrile (HPLC Grade)
2.3 Chromatographic Conditions

| Column: | Waters XBridge Shield RP18 (150 × 3.0 mm, 3.5 µm) |
|---|---|
| PDA Detector Wavelength: | 220 nm |
| Column Temperature: | 40° C. |
| Column Flow: | 1.0 mL/min |
| Injection Volume: | 10 µL |
| Acquisition Time: | 33 min |
| Run Time: | 33 min |
| Diluent: | Methanol |
| Needle Wash: | Methanol |

Mobile Phase A (0.05% TFA-H2O): Accurately transfer 1.0 mL TFA into 2000 mL purified water and mix well. The solution should be filtrated and degassed before use.
Mobile Phase B (0.05% TFA-ACN): Accurately transfer 1.0 mL TFA into 2000 mL acetonitrile and mix well.
Gradient Program:

| Time (min) | A % | B % |
|---|---|---|
| 0.0 | 95 | 5 |
| 5.0 | 95 | 5 |
| 24.0 | 10 | 90 |
| 27.0 | 10 | 90 |
| 27.1 | 95 | 5 |
| 33.0 | | stop |

NOTE: The chromatographic conditions were developed with Agilent 1200 series HPLC.

2.4 Reference Retention Times
(MT-11-0711-01)

| Compound ID | C11030405-E | C11030405-D |
|---|---|---|
| RT (min) | 9.5 | 17.4 |
| RRT | 1.00 | 1.83 |

(AM-C11030405-E-01 Draft 00

| | Compound ID | | | |
|---|---|---|---|---|
| | C11030405-E | C11030405-E2 | C11030405-E1 | C11030405-D |
| RT (min) | 11.7 | 14.3 | 19.4 | 19.8 |
| RRT | 1.00 | 1.24 | 1.73 | 1.77 |

2.5 (IPC) Testing Item: D/E1%
2.5.1 Preparation of solutions
2.5.1.1 Preparation of standard solution
For example: Weigh approximately 10 mg C11030405-D and 25 mg C11030405-E standard into a 100 mL volumetric flask, dissolve and dilute to the volume with diluent, mix well.
2.5.1.2 Preparation of sample solution
Dilute the reaction solution about 300 times with diluent and mix well. The dilution ratio may be adjusted to reach equivalent intensity of C11030405-E in the sample as it is in the standard.
2.5.2 Sample analysis
Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.5.3 Calculation
As per peak area of specified compound, calculate the value of D/E1% as follows:

$$D/E\ 1\% = \frac{S_D}{S_{E1}} \times 100\%$$

Where: $S_D$ represents the peak area of C11030405-D in sample solution
$S_{E1}$ represents the peak area of C11030405-E1 in sample solution (the peak should be confirmed by the project leader)

2.6 (IPC) Testing Item: E2%
2.6.1 Preparation of solutions
2.6.1.1 Preparation of standard solution
For example: Weigh approximately 10 mg C11030405-D and 25 mg C11030405-E standard into a 100 mL volumetric flask, dissolve and dilute to the volume with diluent, mix well.
2.6.1.2 Preparation of sample solution
Dilute the reaction solution about 300 times with diluent and mix well. The dilution ratio may be adjusted to reach equivalent intensity of C11030405-E in the sample as it is in the standard.

2.6.2 Sample analysis
Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.6.3 Calculation
2.6.3.1 Label the known impurities in the sample chromatogram refer to the standard chromatogram.
2.6.3.2 Do not integrate all the peaks with RT in first 2.5 minutes, calculate the peak area percentage (HPLC Area %) of C11030405-E2.

2.7 (IPC) Testing Item: E2/E %
2.7.1 Preparation of solutions
2.7.1.1 Preparation of standard solution
For example: Weigh approximately 10 mg C11030405-D and 25 mg C11030405-E standard into a 100 nil_ volumetric flask, dissolve and dilute to the volume with diluent, mix well.
2.7.1.2 Preparation of sample solution
Dilute the reaction solution about 300 times with diluent and mix well. The dilution ratio may be adjusted to reach equivalent intensity of C11030405-E in the sample as it is in the standard.
2.7.2 Sample analysis
Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.7.3 Calculation
As per peak area of specified compound, calculate the value of E2/E % as follows:

$$E2/E\ \% = \frac{S_{E2}}{S_E} \times 100\%$$

Where: $S_E$, represents the peak area of C11030405-E2 in sample solution (the peak should be confirmed by the project leader)
$S_E$ represents the peak area of C11030405-E in sample solution 2.8 (IPC) Testing Item: Related substances and Assay of C11030405-E
2.8.1 Preparation of solutions
2.8.1.1 Preparation of marker standard solution for related substances determination
For example: Weigh approximately 10 mg C11030405-D and 25 mg C11030405-E standard into a 100 mL volumetric flask, dissolve and dilute to the volume with diluent, mix well. Label it as 1# standard solution.
2.8.1.2 Preparation of standard solution for assay determination
Accurately weigh approximately 25 mg C11030405-E standard into a 100 mL volumetric flask, dissolve and dilute to volume with diluent, mix well. Label it as 2# standard solution.

2.8.1.3 Preparation of sample solution

For example: Accurately weigh approximately 25 mg sample into a 100 mL volumetric flask, dissolve and dilute to the volume with diluent, mix well. The weight of sample may be adjusted to reach equivalent intensity of C11030405-E in the sample as it is in the standard.

2.8.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 1# standard solution | 1 |
| 3 | Sample solution | 1 |

For assay determination:

| Serial No. | Sample Name | No. of Injection |
|---|---|---|
| 1 | Blank (sample diluent) | 1 or more |
| 2 | 2# standard solution | 1 |
| 3 | Sample solution | 1 |

For related substance and assay determination:

| Serial No. | Sample Name | No. of Injection |
|---|---|---|
| 1 | Blank (sample diluent) | 1 or more |
| 2 | 1# standard solution | 1 |
| 3 | 2# standard solution | 1 |
| 4 | Sample solution | 1 |

2.8.3 Calculation 2.8.3.1 Label the known impurities in the sample chromatogram refer to 1# standard chromatogram.

2.8.3.2 As per peak area percentage, calculate the peak area percentage (HPLC Area %) of C11030405-E.

2.8.3.3 As per external standard method, calculate the assay (%, w/w) of sample as follows:

$$\text{Assay}(\%,\ w/w) = \frac{W_{STD} \times P_w}{V_{STD} \times A_{STD}} \times \frac{V_s \times A_s}{W_s} \times 100\%$$

Or $$\text{Assay}(\%,\ g/L) = \frac{W_{STD} \times P_w}{V_{STD} \times A_{STD}} \times A_s \times K$$

Where: $W_{STD}$ represents the weight of C11030405-E in 2#standard solution (mg)

$W_S$ represents the weight of sample (mg)

$V_{STD}$ represents the dilution volume of C11030405-E in 2# standard solution (mL)

$V_S$ represents the dilution volume of sample (mL)

$A_S$ represents the peak area of C11030405-E in sample solution $A_{STD}$ represents the peak area of C11030405-E in 2# standard solution $P_W$ represents the assay value of C11030405-E reference standard K represents the dilution ratio 2.9 (IPC)Testing Item: Residual Compound C11030405-E 2.9.1 Preparation of solutions 2.9.1.1 Preparation of standard solution Accurately weigh approximately 25 mg C11030405-E standard into a 100 mL volumetric flask, dissolve and dilute to volume with diluent, mix well.

2.9.1.2 Preparation of sample solution

Inject sample solution directly. If the concentration is too high, dilute to appropriate concentration with diluent to reach equivalent intensity of C11030405-E in the sample as it is in the standard.

2.9.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

2.9.3 Calculation

As per external standard method, calculate the residual compound C11030405-E as follows:

$$\text{Residual Compound E}(\%,\ w/w) = \frac{W_{STD} \times P_w}{V_{STD} \times A_{STD}} \times \frac{V_s \times A_s}{W_s} \times 100\%$$

$$\text{Residual Compound E}(g/L) = \frac{W_{STD} \times P_w}{V_{STD} \times A_{STD}} \times A_s \times K$$

$$\text{Residual Compound E}(mg/g) = \frac{W_{STD} \times P_w}{V_{STD} \times A_{STD}} \times \frac{V_s \times A_s}{W_s} \times 1000$$

$$\text{Residual Compound E}(g/g) = \frac{W_{STD} \times P_w}{V_{STD} \times A_{STD}} \times \frac{V_s \times A_s}{W_s}$$

Where: $W_{STD}$ represents the weight of C11030405-E in standard solution (mg)

$W_S$ represents the weight of sample (mg)

$V_{STD}$ represents the dilution volume of C11030405-E in standard solution (mL)

$V_S$ represents the dilution volume of sample (mL)

$A_S$ represents the peak area of C11030405-E in sample solution $A_{STD}$ represents the peak area of C11030405-E in standard solution $P_W$ represents the assay value of C11030405-E reference standard K represents the dilution ratio 2.10 (IPC test for intermediate) Testing Item: Related substances and Assay of C11030405-E 2.10.1 Preparation of solutions 2.10.1.1 Preparation of standard solution Accurately weigh approximately 25 mg C11030405-E standard into a 100 mL volumetric flask, dissolve and dilute to volume with diluent, mix well. Two standard solutions should be prepared in parallel and labeled as 1# and 2# standard solution.

2.10.1.2 Preparation of resolution solution

For example: Weigh approximately 10 mg C11030405-D and 25 mg C11030405-E standard into a 100 mL volumetric flask, dissolve and dilute to the volume with diluent, mix well. Label it as 3# standard solution.

2.10.1.3 Preparation of sample solution

Accurately weigh approximately 25 mg sample into a 100 mL volumetric flask, dissolve and dilute to the volume with diluent, mix well. The weight of sample may be adjusted to reach equivalent intensity of C11030405-E in the sample as it is in the standard. Two sample solutions should be prepared in parallel and labeled as 1# sample solution and 2# sample solution.

2.10.2 Sample analysis

Set up instrument condition, after baseline is stabilized, the following injection procedure should be followed:

For related substance determination:

| Serial No. | Sample Name | No. of Injection |
|---|---|---|
| 1 | Blank (sample diluent) | 1 or more |
| 2 | 3# standard solution | 1 |
| 3 | 1# sample solution | 1 |
| 4 | 2# sample solution | 1 |

For related substance and assay determination:

| Serial No. | Sample Name | No. of Injection |
|---|---|---|
| 1 | Blank (sample diluent) | 1 or more |
| 2 | 3# standard solution | 1 |
| 3 | 1# standard solution | 1 |
| 4 | 2# standard solution | 1 |
| 5 | 1# sample solution | 1 |
| 6 | 2# sample solution | 1 |

2.10.3 System suitability 2.10.3.1 The blank should not contain peaks that may interfere with the determination of C11030405-E. If an interference peak is observed, it should be <0.05% peak area of C11030405-E in 1# standard solution.

2.10.3.2 The tailing factor of C11030405-E in all standard solutions should be within 0.8-2.0.

2.10.3.3 The resolution between C11030405-E and its adjacent peaks in the 3# standard solution should be ≥1.5.

2.10.3.4 Calculate % Recovery of 2# STD used as Check STD as per the following calculation formula, % Recovery should be within 98.0%~102.0%.

$$\% \text{ Recovery of Check standard} = \frac{W_1 \times A_2}{W_2 \times A_1} \times 100\%$$

Where: $W_1$ represents the weight of C11030405-E in 1# standard solution (mg)
$W_2$ represents the weight of C11030405-E in 2# standard solution (mg)
$A_2$ represents the peak area of C11030405-E in 2# standard solution
$A_1$ represents the peak area of C11030405-E in 1# standard solution 2.10.4 Calculation 2.10.4.1 Identification: The retention time range for identification of C11030405-E in the sample solution should be ±5.0% of the retention time of C11030405-E in 3# standard solution.

2.10.4.2 Related substances:

2.10.4.2.1 Label the known impurities in the sample chromatogram refer to 3# standard chromatogram.

2.10.4.2.2 As per peak area percentage, calculate the peak area percentage (HPLC Area %) of C11030405-E. If two testing results are within specification limit and the RSD of two results is no more than 2.0%, the average result should be reported as the final result for purity (HPLC Area %) of C11030405-E.

2.10.4.3 Response factor

Calculate the RF in 1# and 2# standard solutions as follows:

$$RF = \frac{A_{STD} \times V_{STD}}{W_{STD} \times P_W}$$

Where: $A_{STD}$ represents the peak area of C11030405-E in standard solution
$V_{STD}$ represents the dilution volume of standard solution (mL)
$W_{STD}$ represents the weight of C11030405-E in standard solution (mg)
$P_W$ represents the assay value of C11030405-E reference standard 2.10.4.4 Assay (%, w/w) of sample Calculate the assay (%, w/w) of sample as follows:

$$\text{Assay}(\%, \text{ w/w}) = \frac{V_s \times A_s}{W_s \times \overline{RF}} \times 100\%$$

Where: $W_S$ represents the weight of sample (mg)
$V_S$ represents the dilution volume of sample (mL)
$A_S$ represents the peak area of C11030405-E in sample solution
$\overline{RF}$ represents the average value of RF for two standard solutions If two testing results are within specification limit and the RSD of two results is no more than 2.0%, the average result should be reported as the final result for Assay (%, w/w).

7.6.3. Method 3

3.1 Instrument

GC, equipped with FID detector
Electronic analytical balance 3.2 Reagent

NMP (HPLC Grade)

3.3 Chromatographic Conditions

| | |
|---|---|
| Column: | DB-624 (30 m * 0.32 mm ID * 1.8 μm) |
| FID Temperature: | 240° C. |
| $H_2$: | 40 mL/min |
| Air: | 400 mL/min |
| Make up ($N_2$) Flow: | 30 mL/min |
| Temperature Program: | 45° C. (5 min) → 10° C./min → 220° C. (3 min) |
| Injector Temperature: | 200° C. |
| Split Ratio: | 20:1 |
| Carrier Gas: | $N_2$ |
| Control Mode: | Linear Velocity |
| Column Flow: | 1.2 mL/min |
| Diluent: | NMP |

Headspace conditions:
Oven Temperature: 80° C.
Needle Temperature: 90° C.
Transfer Temperature: 100° C.
Inject time: 0.05 min
Pressurize time: 0.5 min
Withdraw time: 0.2 min Thermo time: 15.0 min
GC Cycle time: 25.5 min
Hi psi inject Yes
Operation mode: Constant
Injection mode: Time
Column Pressure: 100.0 kPa
Hi Psi Injection Pressure: 130.0 kPa
Solution volume in HS vial: 2.0 mL
3.4 Reference Retention Times (MT-11-0712-01)

| Compound ID | Methanol | MTBE |
|---|---|---|
| RT (min) | 3.4 | 6.2 |

3.5 (IPC) Testing Item: Residual Solvents (Methanol, MTBE)
3.5.1 Preparation of solutions
3.5.1.1 Preparation of standard solution
Accurately weigh approximately 50 mg Methanol and 50 mg MTBE into a 100 mL volumetric flask, dissolve and dilute to the volume with diluent, mix well.
NOTE: The standard solution will be prepared on the basis of the solvents that are used in the process/step as per SP and EBR.
3.5.1.2 Preparation of sample solution (100 mg/mL)
For example:
If the sample is solid, accurately weigh approximately 200 mg sample into a 20 mL HS vial, dissolve with 2 mL diluent and seal, mix well.
If the sample is liquid, accurately weigh approximately 1.0 g sample into a 10 mL volumetric flask, dissolve and dilute to the volume with diluent, mix well.
3.5.2 Sample analysis
Set up instrument condition, after baseline is stabilized, the following injection procedure should be followed:

| Serial No. | Sample Name | No. of Injection |
|---|---|---|
| 1. | Blank (sample diluent) | 1 or more |
| 2. | Standard solution | 1 |
| 3. | Sample solution | 1 |

3.5.3 Calculation
The blank should not contain peaks that may interfere with the quantitation of the relevant solvents. If the signal to noise (S/N) of interference peak is ≥10, the peak area must be revised before it is used to calculate the relevant residual solvent in the sample.
As per external standard method, calculate the value of individual residual solvent as follows:

$$\text{Individual Residual Solvent(ppm)} = \frac{W_{STD}}{V_{STD} \times A_{STD}} \times \frac{V_s \times A_s}{W_s} \times 10^6$$

Or $$\text{Individual Residual Solvent(\%, w/w)} = \frac{W_{STD}}{V_{STD} \times A_{STD}} \times \frac{V_s \times A_s}{W_s} \times 100\%$$

Where: $W_{STD}$ represents the weight of specified solvent in standard solution (mg)
$W_S$ represents the weight of sample (mg)
$V_{STD}$ represents the dilution volume of specified solvent in standard solution (mL)
$V_S$ represents the dilution volume of sample (mL)
$A_S$ represents the revised peak area of specified solvent in sample solution
$A_{STD}$ represents the revised peak area of specified solvent in standard solutions Example 7

In-process Controls (IPC) for Synthesis of Compound (I) (TATD; C11030405-F)

7.7.1. Method 1
1.1 Sample analysis:
Check the appearance via visual
1.2 Testing item: Appearance
7.7.2. Method 2
2.1 Instrument
Karl Fischer Titrator
2.2 Type of titration solutions
HYDRANAL Composite 5
Methanol (HPLC Grade)
2.3 Analytical procedure
After pre-titration is stabilized, take approximately 0.4 g of solid sample or 1 mL of liquid sample to determine the water content. Two samples should be tested in parallel. Report the average value if both of test results meet principle of the method. (The amount of sample can be added or reduced according to the actual water content, but the reason must be recorded.)
2.4 Testing item: Water content (KF)
7.7.3. Method 3
3.1 Instrument
HPLC, equipped with PDA detector and auto-sampler
Electronic analytical balance
Pure water generator
3.2 Reagent
Acetonitrile (HPLC Grade)
Methanol (HPLC Grade)
3.3 Chromatographic Conditions

| Column: | Waters Xbridge C18 (150 × 4.6 mm, 3.5 μm) |
|---|---|
| PDA Detector Wavelength: | 254 nm |
| Column Temperature: | 35° C. |
| Sample Tray Temperature: | 4° C. |
| Column Flow: | 1.0 mL/min |
| Injection Volume: | 5 μL |
| Acquisition Time: | 33 min |
| Run Time: | 33 min |
| Diluent: | $K_2HPO_4$ buffer (PH = 7.0):$H_2O$ = 1:9 (V/V) (For example: Weigh 34.8 g $K_2HPO_4$ into 1000.0 mL water, use 85% $H_3PO_4$ adjust pH to 7.0, then transfer 10.0 mL of this solution dilute to 100.0 mL with water) |
| Needle Wash: | Acetonitrile:water = 1:1 (V/V) |

Mobile Phase A (0.05% TFA-H2O): Accurately transfer 1.0 mL TFA into 2000 mL purified water and mix well. The solution should be filtrated and degassed before use.
Mobile Phase B (0.05% TFA-ACN): Accurately transfer 1.0 mL TFA into 2000 mL acetonitrile and mix well.
Gradient Program:

| Time (min) | A % | B % |
|---|---|---|
| 0.01 | 95 | 5 |
| 15.00 | 55 | 45 |
| 20.00 | 10 | 90 |

-continued

| Time (min) | A % | B % |
|---|---|---|
| 25.00 | 10 | 90 |
| 25.10 | 95 | 5 |
| 33.00 | | stop |

NOTE: The chromatographic conditions were developed with Shimadzu LC-20A series HPLC.

3.4 Reference Retention Times (MT-12-0912-01)

| Compound ID | C11030405-E | C11030405-F |
|---|---|---|
| RT (min) | 12.4 | 16.7 |

3.5 (IPC) Testing Item: E/F %

3.5.1 Preparation of solutions 3.5.1.1 Preparation of standard solution

For example: Weigh approximately 3 mg C11030405-E and 25 mg C11030405-F standard into a 50 mL volumetric flask, dissolve and dilute to the volume with diluent, mix well.

3.5.1.2 Preparation of sample solution

Dilute the reaction solution about 800 times with methanol and mix well. The dilution ratio may be adjusted to reach equivalent intensity of C11030405-F in the sample as it is in the standard.

3.5.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

3.5.3 Calculation

As per peak area of specified compound, calculate the value of E/F % as follows:

$$E/F\ \% = \frac{S_E}{S_F} \times 100\%$$

Where: $S_E$ represents the peak area of C11030405-E in sample solution $S_F$ represents the peak area of C11030405-F in sample solution 3.6 (IPC) Testing Item: Related substances and Assay of C11030405-F 3.6.1 Preparation of solutions 3.6.1.1 Preparation of marker standard solution for related substances determination For example: Weigh approximately 3 mg C11030405-E and 25 mg C11030405-F standard into a 50 mL volumetric flask, dissolve and dilute to the volume with diluent, mix well. Label it as 1# standard solution.

3.6.1.2 Preparation of standard solution for assay determination

Accurately weigh approximately 25 mg C11030405-F standard into a 50 mL volumetric flask, dissolve and dilute to volume with diluent, mix well. Label it as 2# standard solution.

3.6.1.3 Preparation of sample solution

For example: Accurately weigh approximately 25 mg sample into a 50 mL volumetric flask, dissolve and dilute to the volume with diluent, mix well. The weight of sample may be adjusted to reach equivalent intensity of C11030405-F in the sample as it is in the standard.

3.6.2 Sample analysis

Set up instrument condition, after baseline is stabilized, the following injection procedure should be followed:

For related substance determination:

| Serial No. | Sample Name | No. of Injection |
|---|---|---|
| 1. | Blank (sample diluent) | 1 or more |
| 2. | 1# standard solution | 1 |
| 3. | Sample solution | 1 |

For assay determination:

| Serial No. | Sample Name | No. of Injection |
|---|---|---|
| 1 | Blank (sample diluent) | 1 or more |
| 2 | 2# standard solution | 1 |
| 3 | Sample solution | 1 |

For related substance and assay determination:

| Serial No. | Sample Name | No. of Injection |
|---|---|---|
| 1 | Blank (sample diluent) | 1 or more |
| 2 | 1# standard solution | 1 |
| 3 | 2# standard solution | 1 |
| 4 | Sample solution | 1 |

3.6.3 Calculation 3.6.3.1 Label the known impurities in the sample chromatogram (refer to the 1# standard chromatogram).

3.6.3.2 If there have no require for impurities control, calculate the peak area percentage (HPLC Area %) of C11030405-F.

3.6.3.2 If there have requires for impurities control, calculate the relative retention time (RRT) and peak area percentage (area %) for each impurity.

Data report:

Report all impurities that are not less than 0.02%, reference to their RRT or name, and present to two decimal places.

For impurities that are less than 0.02% cannot be reported. But if all impurities are less than 0.02% report as "no single impurity is more than 0.02%".

For total impurities: Sum all individual impurities that are no less than 0.02% and present to two decimal places. Individual impurities which are lower than 0.02% are not included in the calculation of total impurities.

Purity of C11030405-F (HPLC Area %)=100%-total impurities.

3.6.3.3 As per external standard method, calculate the assay (%, w/w) of sample as follows:

$$\text{Assay}(\%,\ \text{w/w}) = \frac{W_{STD} \times P_w}{V_{STD} \times A_{STD}} \times \frac{V_s \times A_s}{W_s} \times 100\%$$

Or

-continued $$\text{Assay(g/L)} = \frac{W_{STD} \times P_w}{V_{STD} \times A_{STD}} \times A_s \times K$$

Where: $W_{STD}$ represents the weight of C11030405-F in 2# standard solution (mg)
$W_S$ represents the weight of sample (mg)
$V_{STD}$ represents the dilution volume of C11030405-F in 2# standard solution (mL)
$V_S$ represents the dilution volume of sample (mL)
$A_S$ represents the peak area of C11030405-F in sample solution
$A_{STD}$ represents the peak area of C11030405-F in 2# standard solution
$P_W$ represents the assay value of C11030405-F reference standard
K represents the dilution ratio 3.7 (IPC) Testing Item: Residual Compound C11030405-F 3.7.1 Preparation of solutions 3.7.1.1 Preparation of standard solution Accurately weigh approximately 25 mg C11030405-F standard into a 50 mL volumetric flask, dissolve and dilute to volume with diluent, mix well.

3.7.1.2 Preparation of sample solution

For liquid: Inject sample solution directly. If the concentration is too high, dilute to appropriate concentration with methanol to reach equivalent intensity of C11030405-F in the sample as it is in the standard.

For solid: weigh approximately 3 g sample into a 100 mL volumetric flask, dissolve and dilute to volume with methanol, sonicate for 5 minutes and mix well, then filter it with 0.45 μm syringe filters. If the concentration is too high, dilute to appropriate concentration with methanol to reach equivalent intensity of C11030405-F in the sample as it is in the standard.

3.7.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 1 |

3.7.3 Calculation

As per external standard method, calculate the residual compound C11030405-F as follows:

$$\text{Residual Compound F(\%, w/w)} = \frac{W_{STD} \times P_w}{V_{STD} \times A_{STD}} \times \frac{V_s \times A_s}{W_s} \times 100\%$$

$$\text{Residual Compound F(g/L)} = \frac{W_{STD} \times P_w}{V_{STD} \times A_{STD}} \times A_s \times K$$

Where: $W_{STD}$ represents the weight of C11030405-F in standard solution (mg)
$W_S$ represents the weight of sample (mg)
$V_{STD}$ represents the dilution volume of C11030405-F in standard solution (mL)
$V_S$ represents the dilution volume of sample (mL)
$A_S$ represents the peak area of C11030405-F in sample solution
$A_{STD}$ represents the peak area of C11030405-F in standard solution
$P_W$ represents the assay value of C11030405-F reference standard
K represents the dilution ratio 7.7.4. Method 4

4.1 Instrument
GC, equipped with FID detector
Electronic analytical balance 4.2 Reagent
DMI (HPLC Grade)

4.3 Chromatographic Conditions

| | |
|---|---|
| Column: | DB-624 (30 m*0.32 mm ID*1.8 μm) |
| FID Temperature: | 260° C. |
| $H_2$: | 40 mL/min |
| Air: | 400 mL/min |
| Make up ($N_2$) Flow: | SHIMADZU 2010: 30 mL/min; Agilent 7890: 25 mL/min |
| Temperature Program: | 45° C. (5 min) → 10° C./min → 220° C. (3 min) |
| Injector Temperature: | 120° C. |
| Split Ratio: | 20:1 |
| Carrier Gas: | $N_2$ |
| Control Mode: | SHIMADZU 2010: Linear Velocity; Agilent 7890: Constant Flow |
| Linear Velocity: | 30 cm/sec |
| Diluent: | DMI |

Headspace conditions:
Oven Temperature: 70° C.
Needle Temperature: 80° C.
Transfer Temperature: 120° C.
Inject time: 0.05 min
Pressurize time: 3.0 min
Withdraw time: 0.2 min
Thermo time: 10.0 min
GC Cycle time: 30.0 min
Hi psi inject Yes
Operation mode: Constant
Injection mode: Time
Column Pressure: 110 kPa
Hi Psi Injection Pressure: 130 kPa
Solution volume in HS vial: 2.0 mL
NOTE:

1. In order to elute strongly retained components from the GC column and ensure the reproducibility of continuous sample injections, the hold time at 220° C. can be extended according to the different characteristic of the sample.

2. In order to ensure proper recovery of the residual solvents in the sample, the Linear Velocity and oven temperature must be tightly controlled.

4.4 Reference Retention Times (MT-12-0844-01)

| Compound ID | Methanol | MTBE | THF |
|---|---|---|---|
| RT (min) | 2.7 | 5.3 | 7.4 |

4.5 (IPC) Testing Item: Residual Solvents (Methanol, MTBE, THF)

4.5.1 Preparation of solutions 4.5.1.1 Preparation of standard solution

Accurately weigh approximately 300 mg methanol, 500 mg MTBE and 72 mg THF into a 100 mL volumetric flask, dissolve and dilute to the volume with diluent. Accurately transfer 5.0 mL of this solution into a 50 mL volumetric flask, dilute to the volume with diluent, and mix well.

NOTE: The standard solution will be prepared on the basis of the solvents that are used in the process/step as per SP and EBR.

4.5.1.2 Preparation of sample solution (100 mg/mL

For example: accurately weigh approximately 200 mg sample into a 20 mL HS vial, dissolve with 2 mL diluent and seal, mix well.

4.5.2 Sample analysis

Set up instrument condition, after baseline is stabilized, the following injection procedure should be followed:

| Serial No. | Sample Name | No. of Injection |
|---|---|---|
| 1. | Blank (sample diluent) | 1 or more |
| 2. | Standard solution | 1 |
| 3. | Sample solution | 1 |

4.5.3 Calculation

The blank should not contain peaks that may interfere with the quantitation of the relevant solvents. If the signal to noise (S/N) of interference peak is ≥10, the peak area must be revised before it is used to calculate the relevant residual solvent in the sample.

As per external standard method, calculate the value of individual residual solvent as follows:

$$\text{Individual Residual Solvent}(\%, w/w) = \frac{W_{STD}}{V_{STD} \times A_{STD}} \times \frac{V_s \times A_s}{W_s} \times 100\%$$

Or $$\text{Individual Residual Solvent}(ppm) = \frac{W_{STD}}{V_{STD} \times A_{STD}} \times \frac{V_s \times A_s}{W_s} \times 10^6$$

Where: $W_{STD}$ represents the weight of specified solvent in standard solution (mg)
$W_S$ represents the weight of sample (mg)
$V_{STD}$ represents the dilution volume of specified solvent in standard solution (mL)
$V_S$ represents the dilution volume of sample (mL)
$A_S$ represents the revised peak area of specified solvent in sample solution
$A_{STD}$ represents the revised peak area of specified solvent in standard solutions Note: Revised peak area is obtained by subtracting the area of interfering peak in the blank chromatogram from the peak area of specified solvent in the sample chromatogram.

7.7.5. Method 5

5.1 Instrument
GC, equipped with FID detector
Electronic analytical balance 5.2 Reagent
THF (HPLC Grade)
Methanol (AR Grade)
MTBE (AR Grade)

5.3 Chromatographic Conditions

| Column: | DB-624 (30 m*0.32 mm ID*1.8 μm) |
|---|---|
| FID Temperature: | 250° C. |
| H₂: | 40 mL/min |
| Air: | 400 mL/min |
| Make up (N₂) Flow: | 30 mL/min |
| Temperature Program: | 45° C. (5min) → 20° C./min → 250° C. (3 min) |
| Injector Temperature: | 200° C. |
| Split Ratio: | 80:1 |
| Carrier Gas: | N₂ |

-continued

| Control Mode: | Linear Velocity |
|---|---|
| Column Flow: | 1.2 mL/min |
| Injection Volume: | 0.2 μL |
| Diluent: | THF |
| Needle Wash: | THF |

NOTE: 1. In order to elute strongly retained components from the GC column and ensure the reproducibility of continuous sample injections, the hold time at 250° C. can be extended according to the different characteristic of the sample.

5.4 Reference Retention Times (MT-13-1318-01)

| Compound ID | Methanol | MTBE | THF |
|---|---|---|---|
| RT (min) | 3.7 | 6.5 | 8.1 |

5.5 (IPC) Testing Item: Purity of recovery of THF 5.5.1 Preparation of solutions 5.5.1.1 Preparation of standard solution Weigh approximately 50 mg Methanol and 50 mg MTBE into a 100 mL volumetric flask, dissolve and dilute to the volume with diluent, and mix well.

5.5.1.2 Preparation of sample solution

Inject directly.

5.5.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Standard solution | 1 |
| 3 | Sample solution | 2 |

5.5.3 Calculation 5.5.3.1 Label the known impurities in the sample chromatogram (refer to the standard chromatogram).

5.5.3.2 Calculate the peak area percentage (HPLC Area %) of THF.

7.7.6. Method 6

6.1 Instrument: Dual-purpose burette 6.2 Reagents

10% KI solution: Weigh approximately 10 g KI, dissolve with 100 mL water, and mix well. Need to prepare freshly.

Acetic acid, Chloroform, KI, 0.1 N Sodium thiosulfate VS 6.3 (IPC) Testing item: Content of Peroxide (ppm)

6.3.1 Operate procedure:

6.3.1.1 Add freshly prepared of 10% KI solution into 10 mL THF, shake, if the color of solution show yellowish-brown, proved it has peroxide, keep on operating 6.3.1.2; if the color of solution is without change, then report N.D.

6.3.1.2 Add 6 mL Acetic acid, 4 mL Chloroform and 1 g KI into 50 mL THF, then add 5 mL water, place it in dark for 5 minutes. Titrate it with 0.1 N Sodium thiosulfate VS until the solution becomes colorless. Record the volume of Sodium thiosulfate VS in the end of the titration.

6.3.2 Calculation $$\text{Peroxide, ppm} = \frac{C \times V \times 0.104}{2 \times 0.889 \times 50} \times 10^6$$

Where: C represents the concentration of Sodium thiosulfate VS (mol/L)

V represents the volume of sample used Sodium thiosulfate VS (mL)

0.104 represents the mMW of THF peroxide (g/mmoL)

0.889 represents the density of THF (g/mL)

6.3.3 Data report

Report the calculation results 7.7.7. Method 7

7.1 Instrument

GC, equipped with FID detector

Electronic analytical balance 7.2 Reagent

DMF (HPLC Grade)

7.3 Chromatographic Conditions

| Column: | HP-5 (30 m*0.32 mm ID*1.0 µm) |
|---|---|
| FID Temperature: | 270° C. |
| $H_2$: | 40 mL/min |
| Air: | 400 mL/min |
| Make up ($N_2$) Flow: | 30 mL/min |
| Temperature Program: | 50° C. (5 min) → 10° C./min → 250° C. (5 min) |
| Injector Temperature: | 200° C. |
| Split Ratio: | 20:1 |
| Carrier Gas: | $N_2$ |
| Control Mode: | Linear Velocity |
| Linear Velocity: | 30 cm/sec |
| Injection Volume: | 1.0 µL |
| Diluent: | DMF |
| Needle Wash: | DMF |

NOTE: 1. In order to elute strongly retained components from the GC column and ensure the reproducibility of continuous sample injections, the hold time at 250° C. can be extended according to the different characteristic of the sample.

7.4 Reference Retention Times (MT-14-1929-01)

| Compound ID | Methanol | MTBE | THF |
|---|---|---|---|
| RT (min) | 2.0 | 3.2 | 4.3 |

7.5 (IPC) Testing Item: Purity and assay of recovery of Methanol 7.5.1 Preparation of solutions 7.5.1.1 Preparation of standard solution (20 mg/mL of Methanol)

Weigh approximately 200 mg Methanol into a 10 mL volumetric flask, dissolve and dilute to the volume with diluent, and mix well. Label it as STD solution.

7.5.1.2 Preparation of sensitivity solution (0.02 mg/mL of Methanol)

Transfer 1.0 mL of STD solution into a 100 mL volumetric flask, dilute to the volume with diluent, Then, accurately transfer 1.0 mL of this solution into a 10 mL volumetric flask, dilute to the volume with diluent, and mix well.

7.5.1.3 Preparation of ID standard solution (20 mg/mL of Methanol, 2 mg/mL of MTBE and 2 mg/mL of THF)

For example: Accurately weigh approximately 200 mg Methanol, 20 mg MTBE and 20 mg THF into a 10 mL volumetric flask, dissolve and dilute to the volume with diluent, and mix well. Label it as Marker solution.

7.5.1.4 Preparation of sample solution (40 mg/mL)

Weigh approximately 200 mg sample into a 5 mL volumetric flask, dissolve and dilute to the volume with diluent, mix well. Label it as SPL solution.

7.5.2 Sample analysis

Set up instrument condition, after baseline is stabilized, the following injection procedure should be followed:

| Serial No. | Sample Name | No. of Injection |
|---|---|---|
| 1 | Blank (sample diluent) | 1 or more |
| 2 | Sensitivity solution | 1 |
| 3 | Marker solution | 1 |
| 4 | STD solution | 3 |
| 5 | SPL solution | 1 |

7.5.3 System Suitability 7.5.3.1 The blank should not contain peaks that may interfere with the quantitation of methanol. If an interfering peak is present, that should be less than the peak in sensitivity solution of the nominal concentration of methanol peak.

7.5.3.2 The tailing factor of methanol in all standard solutions should be within 0.8-2.0.

7.5.3.3 The ratio of signal to noise (S/N) for the sensitivity solution should be ≥10:

7.5.3.4 RSD of peak area of methanol for first three injections of STD solution should be no more than 5.0% and RSD of retention time of methanol for first three injections of STD solution should be no more than 1.0%.

7.5.4 Calculation 7.5.4.1 Do not integrate the peaks that in blank, integrate the peaks that are no less than 0.1%, and label the peaks of methanol, MTBE, THF in the sample chromatogram.

7.5.4.2 Calculate the peak area percentage (HPLC Area %) of Methanol.

7.5.4.3 Calculate the Purity of (Methanol+MTBE+THF) in sample as follows:

$$\text{Purity of MeOH} + \text{MTBE} + \text{THF} = \frac{A_{MeOH} + A_{MTBE} + A_{THF}}{A_{Total}} \times 100\%$$

Where: $A_{MeOH}$ represents the peak area of methanol in sample solution $A_{MTBE}$ represents the peak area of MTBE in sample solution $A_{THF}$ represents the peak area of THF in sample solution $A_{Total}$ represents the sum of the peak areas of all of the peaks in sample solution 7.5.4.4 As per external standard method, calculate the assay (%, w/w) of methanol as follows:

$$\text{Assay}(\%, \text{w/w}) = \frac{W_{STD} \times P_w}{V_{STD} \times A_{STD}} \times \frac{V_s \times A_s}{W_s} \times 100\%$$

Or $$\text{Assay}(g/L) = \frac{W_{STD} \times P_w}{V_{STD} \times A_{STD}} \times A_s \times K$$

Where: $W_{STD}$ represents the weight of methanol in standard solution (mg)

$W_S$ represents the weight of sample (mg)

$V_{STD}$ represents the dilution volume of methanol in standard solution (mL)

$V_S$ represents the dilution volume of sample (mL)

$A_S$ represents the peak area of methanol in sample solution $A_{STD}$ represents the peak area of methanol in standard solution $P_W$ represents the assay value of methanol reference standard K represents the dilution ratio.

Example 8

XRPD Instrument and Procedure

A Bruker D8 diffractometer using Cu Kα radiation (40 kV, 40 mA), θ-2θ goniometer, and primary & secondary soller slits (2.5°), a Ge monochromator and Lynxeye detector (opening angle of) 2.948°) were utilized to collect X-ray Powder Diffraction Patterns. Certified Corundum standard (NIST 1976) was used to check the performance of the instrument. Data collection was performed by the Diffrac-.Suite Measurement Center v2.2.47.1 and the data was analyzed and presented using Diffrac.EVA v2.0 or v3.0.

Samples were tested under ambient conditions. Approximately 400 mg of each sample was grinded for 3 minutes in a mortar and pestle. The sample was prepared by back-loading the triturated material into the sample holder and supporting it with a zero background silicon wafer. Once tightly packed, a flat surface was formed. When the sample was carefully flipped over, the appearance of the API in the sample holder appeared very similar to the appearance of the Corundum sample from NIST used to verify the performance of the instrument. The details of the data collection are:

Scan type: Coupled TwoTheta/Theta
Angular range: 3 to 50° 2θ
Step size: 0.015° 2θ
Collection time: 1 s
Goniometer radius: 280 mm
Sample rotation speed: 15 rpm
Slit size: 0.6 mm.

8. EMBODIMENTS

1. Compound Int C having the structure:

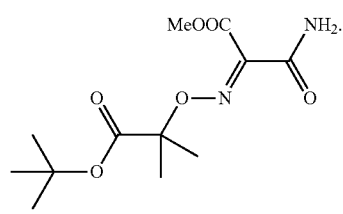

Int C

2. A method of making compound Int C:

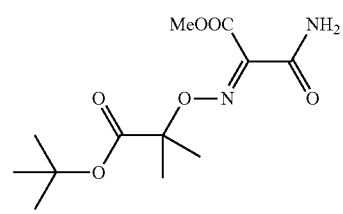

Int C comprising the step of reacting compound Int B with NH₃:

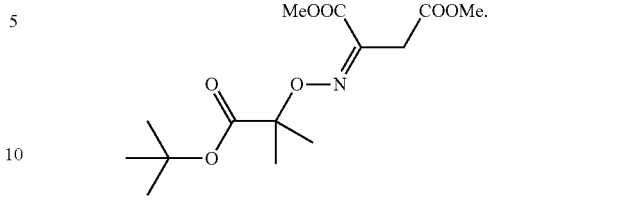

Int B

3. The method of Embodiment 2, wherein compound Int B is reacted with NH3 in the presence of H₂O and CH₃OH.

4. The method of Embodiment 2, wherein compound Int B is produced by a method comprising the steps of:
(a) converting compound SM1 into compound Int A:

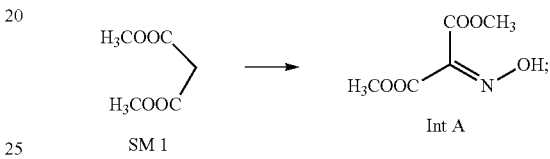

and
(b) converting compound Int A into compound Int B:

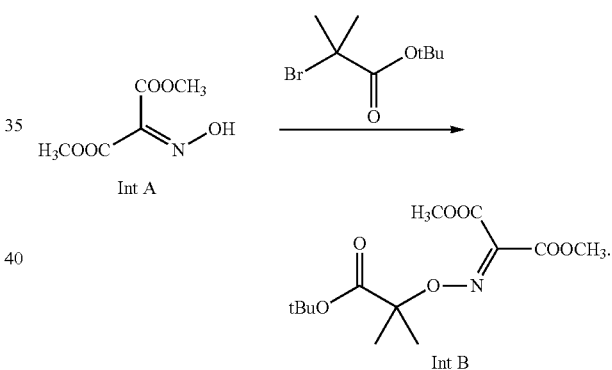

5. The method of Embodiment 2, wherein compound Int C is converted into compound (I) by a method comprising the steps of:
(a) converting compound Int C into compound Int D:

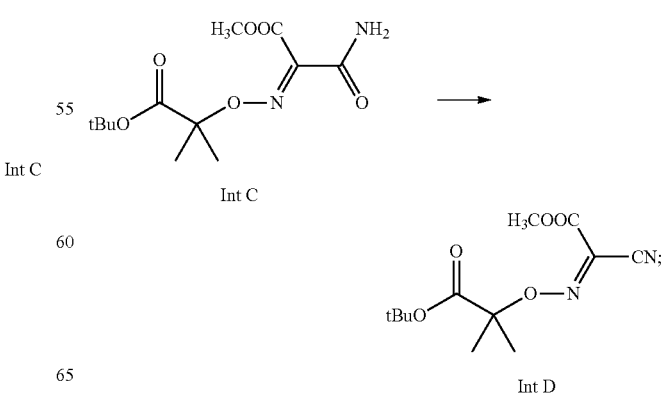

(b) converting compound Int D into compound Int E1:

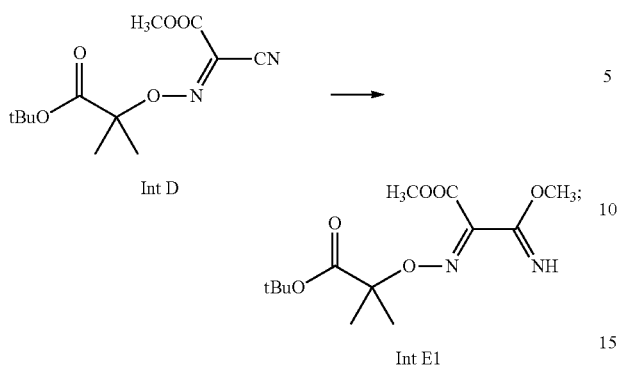

Int D

Int E1

(c) converting compound Int E1 into compound Int E2:

Int E1

Int E2

(d) converting compound Int E2 into compound Int E:

Int E2

Int E and
(e) converting compound Int E into compound (I):

Int E

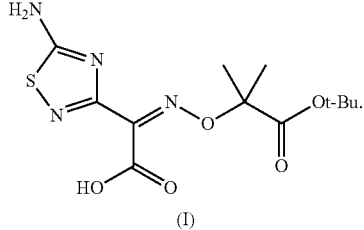

(I)

6. A method of making compound (I) comprising the steps of:
(a) converting compound Int E2 into compound Int E:

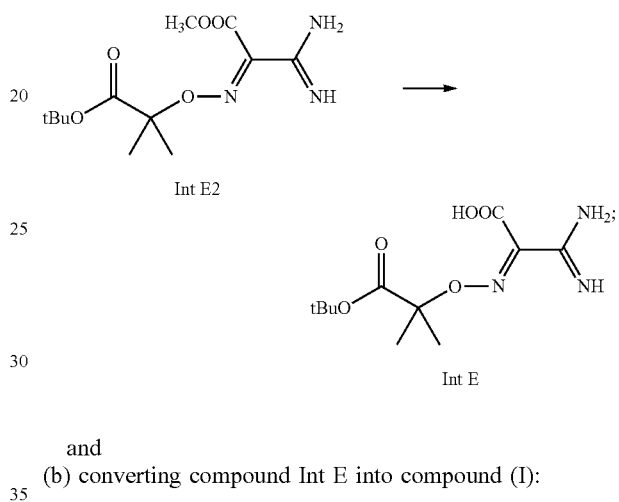

Int E2

Int E and
(b) converting compound Int E into compound (I):

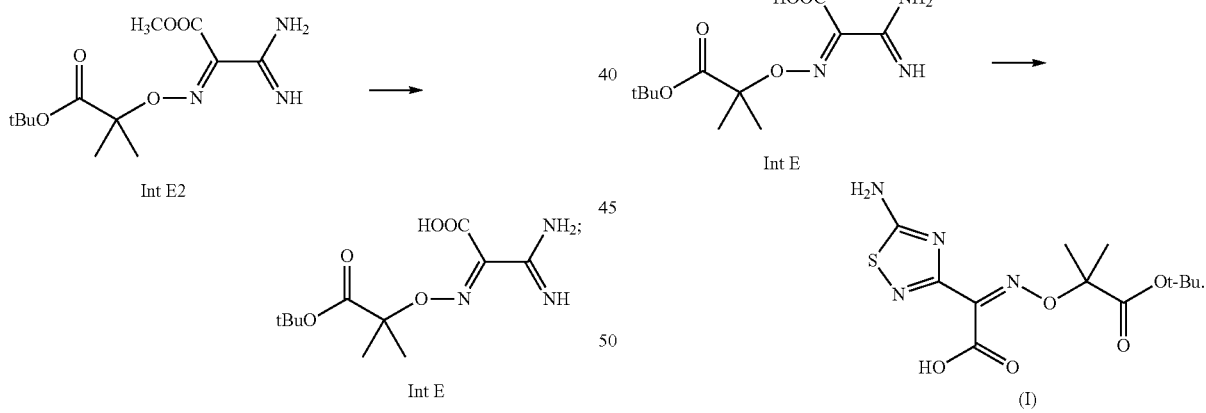

Int E (I)

7. The method of Embodiment 6, wherein compound Int E2 is produced by a method comprising the steps of:
(a) converting compound Int D into compound Int E1:

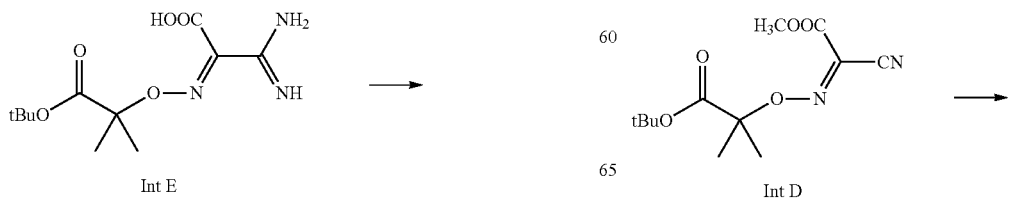

Int D

-continued

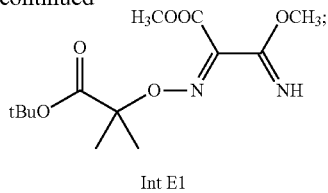

Int E1 and
(b) converting compound Int E1 into compound Int E2:

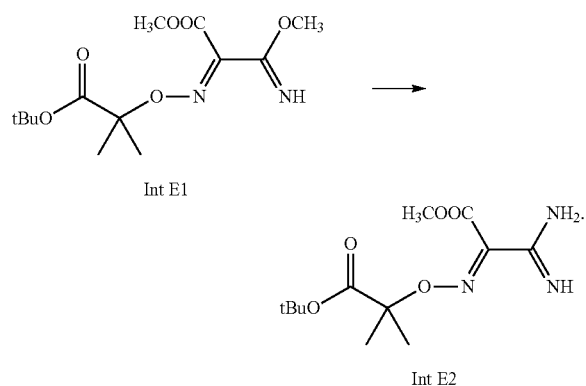

Int E1

Int E2

8. The method of Embodiment 7, wherein step (a) comprises converting compound Int D into compound Int E1 at a temperature between about 0° C. and 18° C., and step (b) comprises converting compound Int E1 into compound Int E2 at a temperature between about 15° C. and 18° C.

9. The method of Embodiment 7, wherein compound Int D is produced by a method comprising the steps of:
(a) converting compound Int B into compound Int C:

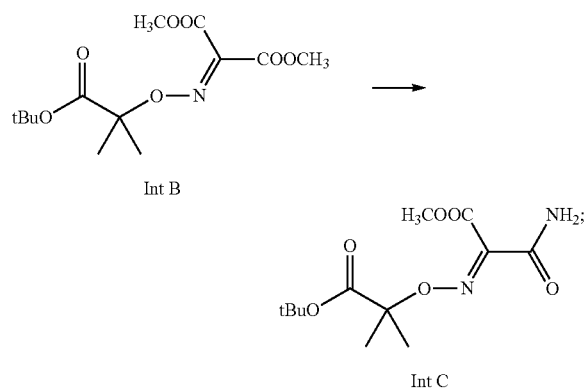

Int B

Int C and
(b) converting compound Int C into compound Int D:

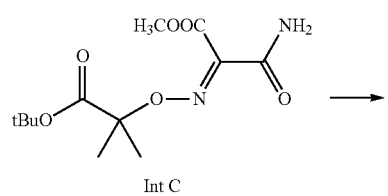

Int C

-continued

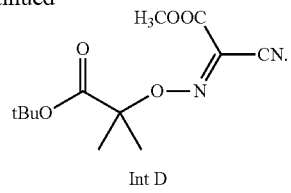

Int D

10. The method of Embodiment 9, wherein compound Int B is produced by a method comprising the steps of:
(a) converting compound SM1 into compound Int A:

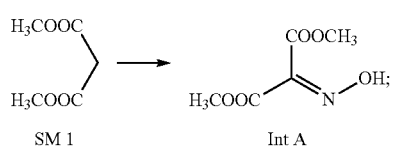

SM 1

Int A and
(b) converting compound Int A into compound Int B:

Int A

Int B

11. The method of Embodiment 6, wherein the step of converting compound Int E into compound (1) comprises the steps of:
(a) forming a mixture comprising methanol and compound Int E;
(b) adding triethylamine;
(c) adding bromine;
(d) adding a thiocyanate salt;
(e) adjusting the pH of the reaction mixture to 2.5 with an aqueous solution of hydrochloric acid; and
(f) obtaining compound (I).

12. The method of Embodiment 6, wherein the step of converting compound Int E2 into compound Int E comprises the steps of:
(a) combining compound Int E2 with a solution comprising an hydroxide salt;
(b) agitating the combination of step (a);
(c) addition of acid; and
(d) obtaining compound Int E.

13. The method of Embodiment 7, wherein the step of converting compound Int D into compound Int E2 comprises the steps of:
(a) forming a reaction mixture comprising methanol, sodium methoxide, and compound Int D, thereby forming compound Int E1;
(b) adjusting the pH of the reaction mixture to 6.5 with acetic acid and adding ammonium chloride, thereby converting compound Int E1 into compound Int E2.

14. The method of Embodiment 9, wherein the step of converting compound Int C into compound Int D comprises the steps of:
(a) forming a reaction mixture comprising methyl tert-butyl ether, phosphorus pentachloride and pyridine;
(b) combining compound Int C with the reaction mixture of step (a);
(b) adding an aqueous solution of methanol; and
(c) obtaining compound Int D.

15. The method of Embodiment 9, wherein the step of converting compound Int B into compound Ent C comprises the steps of:
(a) combining compound Int B with ammonia, water and methanol;
(b) adjusting the pH of the reaction mixture to a pH of about 5 with hydrochloric acid; and
(c) obtaining compound Int C.

16. The method of Embodiment 10, wherein the step of converting compound Int A into compound Int B comprises the steps of:
(a) combining compound Int A with compound SM 2, triethylamine and dimethylformamide; and
(b) obtaining compound Int B.

17. The method of Embodiment 10, wherein the step of converting compound SM1 into compound Int A comprises the steps of:
(a) forming a reaction mixture comprising water, sodium nitrite, acetic acid and compound SM 1;
(b) adjusting the pH of the reaction mixture to about 6.5 with acetic acid; and
(c) obtaining compound Int A.

18. A composition comprising compound Int B and compound Int C.

19. A composition comprising compound Int E2 and compound E.

20. A composition comprising compound Int E and compound (I).

21. Compound (I):

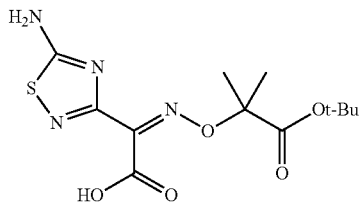

(I)

prepared by a method comprising the steps of:
(a) converting compound Int B into compound Int C:

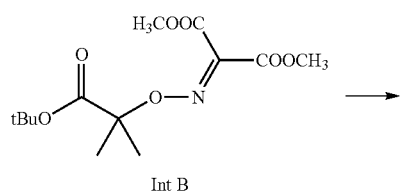

Int B

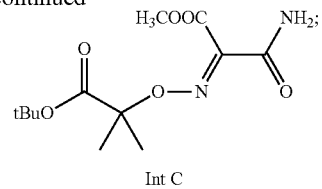

Int C and
(b) converting compound Int E2 into compound Int E:

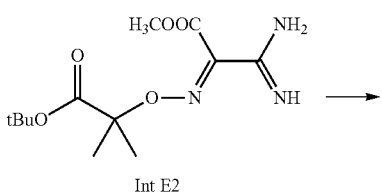

Int E2

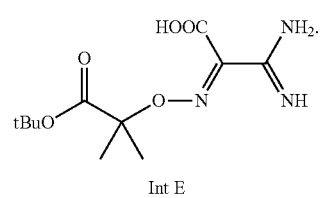

Int E

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:
1. A process of making a compound of formula (Z-I):

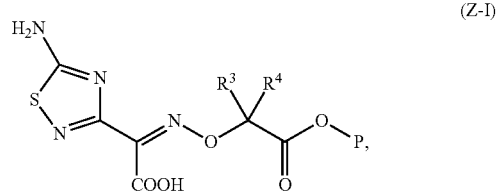

(Z-I)

wherein:
P is an acid-labile oxygen protecting group,
$R^3$ and $R^4$ are each independently $C_{1-6}$ alkyl;
the process comprising admixing a compound of formula Int Z-E:

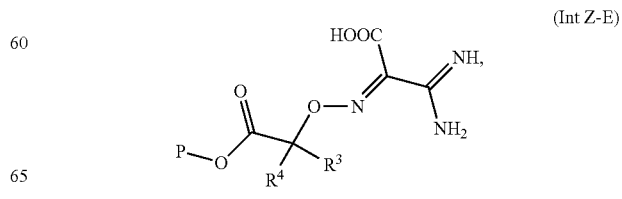

(Int Z-E)

a thiocyanate salt, and an oxidant,
to provide the compound of formula (Z-I).

2. The process of claim 1, wherein $R^3$ is methyl.

3. The process of claim 1, wherein $R^4$ is methyl.

4. The process of claim 1, wherein P is tert-butyl.

5. The process of claim 1, wherein the oxidant comprises bromine.

6. The process of claim 5, wherein the amount of bromine is from about 1.35 to about 1.42 equivalents compared with the molar amount of the compound of formula (Z-I).

7. The process of claim 1, wherein the thiocyanate salt comprises ammonium thiocyanate or potassium thiocyanate.

8. The process of claim 1, comprising admixing in an alcohol solvent.

9. The process of claim 8, wherein the alcohol solvent comprises methanol.

10. The process of claim 1, further comprising making the compound of formula Int Z-E from a compound of formula Int Z-E1:

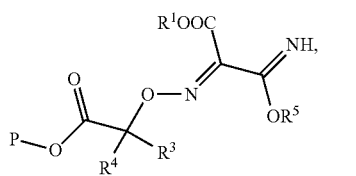
(Int Z-E1)

wherein $R^1$ and $R^5$ are each independently $C_{1-6}$ alkyl;
comprising the steps of:
(a1) admixing the compound of formula Int Z-E1 and an ammonia source, and
(b1) contacting the admixture with a base;
or
(a2) admixing the compound of formula Int Z-E1 and a base, and
(b2) contacting the admixture with an ammonia source,
to provide the compound of formula Int Z-E.

11. The process of claim 10, further comprising making the compound of formula Int Z-E1 from a compound of formula Int Z-C:

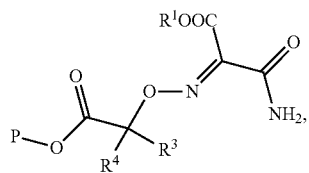
(Int Z-C)

comprising the steps of:
(a) dehydrating the compound of formula Int Z-C; and
(b) contacting the dehydrate with a compound of formula $MOR^5$,
wherein M is lithium, sodium, or potassium,
to provide the compound of formula Int Z-E1.

12. The process of claim 11, further comprising making the compound of formula Int Z-C comprising contacting ammonia with a compound of formula Int Z-B:

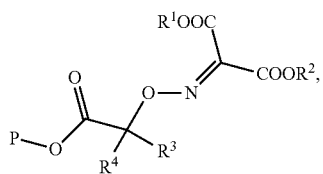
(Int Z-B)

wherein $R^2$ is $C_{1-6}$ alkyl,
to provide the compound of formula Int Z-C.

13. The process of claim 12, wherein the reaction temperature is from about −10° C. to about 5° C.

14. The process of claim 1, wherein the compound of formula (Z-I) has the structure of compound (I):

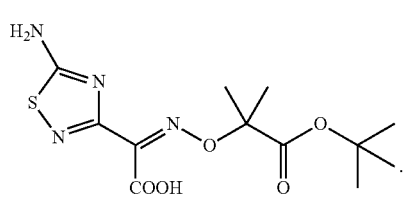
(I)

* * * * *